(12) United States Patent
Kawase et al.

(10) Patent No.: US 6,999,685 B1
(45) Date of Patent: Feb. 14, 2006

(54) POLARIZED LIGHT COMMUNICATION DEVICE, TRANSMITTER, LASER, POLARIZED LIGHT COMMUNICATION DEVICE FOR PHYSIOLOGICAL USE, REFLECTED LIGHT DETECTOR AND PULSE WAVE DETECTING DEVICE

(75) Inventors: Takeo Kawase, Suwa (JP); Kazuhiko Amano, Yokohama (JP); Shojiro Kitamura, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 09/214,140

(22) PCT Filed: Apr. 30, 1998

(86) PCT No.: PCT/JP98/01992

§ 371 (c)(1),
(2), (4) Date: Apr. 8, 1999

(87) PCT Pub. No.: WO98/51025

PCT Pub. Date: Nov. 12, 1998

(30) Foreign Application Priority Data

Jan. 31, 1997 (JP) .................................... 9-18883
Feb. 28, 1997 (JP) .................................... 9-46197
May 2, 1997 (JP) .................................... 9-114918

(51) Int. Cl.
 H04B 10/08 (2006.01)
 H04B 10/00 (2006.01)
 H04J 14/06 (2006.01)

(52) U.S. Cl. ........................ 398/129; 398/131; 398/65; 398/22

(58) Field of Classification Search ................ 359/156, 359/159, 170, 172, 173; 398/141, 152, 164, 398/170, 171
See application file for complete search history.

(56) References Cited

U.S. PATENT DOCUMENTS

| 3,566,126 | A | | 2/1971 | Lang et al. |
| 4,951,679 | A | | 8/1990 | Harada |
| 4,987,897 | A | * | 1/1991 | Funke ........................ 607/32 |
| 5,396,508 | A | | 3/1995 | Bour et al. ................... 372/27 |
| 5,416,626 | A | * | 5/1995 | Taylor ........................ 398/185 |

(Continued)

FOREIGN PATENT DOCUMENTS

EP  0 030 610 A1  6/1981

(Continued)

OTHER PUBLICATIONS

National Cardiovascular Center, Research Institute, *Transcutaneous Optical Telemetry System Using Laser Diode*, Katsushige Inoue, et al. pp. 23-27.

(Continued)

*Primary Examiner*—Leslie Pascal
*Assistant Examiner*—Dzung Tran
(74) *Attorney, Agent, or Firm*—Mark P. Watson

(57) ABSTRACT

A physiological function assisting device 1 is embedded in the body, and is provided with a transmitter 11 and receiver 12 for communicating with an external controller 2. External controller 2 controls embedded physiological function assisting device 1 from the outside. External controller 2 is provided with a transmitter 21 and receiver 22 for communicating with physiological function assisting device 1. Transmitters 11,21 modulate the plane of polarization of laser light, and emit the result as a transmission signal. Receivers 12,22 selectively receive light of a specific polarization state. Receivers 12,22 respectively output electric signals corresponding to the polarization state (polarization angle or ellipticity) of the received light. As a result, full duplex communications between a strongly dispersing medium like the human body and the outside is possible, while the power consumed by the internal device can be reduced.

2 Claims, 37 Drawing Sheets

U.S. PATENT DOCUMENTS

| | | | |
|---|---|---|---|
| 5,465,263 A | 11/1995 | Bour et al. | 372/23 |
| 5,680,241 A * | 10/1997 | Sakanaka et al. | 356/432 |
| 5,807,397 A * | 9/1998 | Barreras | 607/61 |
| 6,005,709 A * | 12/1999 | Silver | 359/368 |

FOREIGN PATENT DOCUMENTS

| | | |
|---|---|---|
| JP | 60-135029 | 7/1985 |
| JP | 2-60628 | 3/1990 |
| JP | 3-75037 | 3/1991 |
| JP | 04-064335 | 2/1992 |
| JP | 5-115448 | 5/1993 |
| JP | 6-190 | 1/1994 |
| JP | 6-302911 | 10/1994 |
| JP | 7-146305 | 6/1995 |
| JP | 7-148127 | 6/1995 |
| JP | 7-202162 | 8/1995 |
| JP | 7-273726 | 10/1995 |
| JP | 7-323014 | 12/1995 |
| JP | 7-326813 | 12/1995 |
| JP | 8-148715 | 6/1996 |
| JP | 8-186313 | 7/1996 |
| JP | 8-250812 | 9/1996 |
| JP | 8-304750 | 11/1996 |
| JP | 11-509748 | 8/1999 |
| WO | WO 96/39922 | 12/1996 |
| WO | WO 96/39925 | 12/1996 |

OTHER PUBLICATIONS

The Institute of Electronics, Information and Communication Engineers, Technical Report of IEICE, vol. 95, No. 291, Oct. 13, 1995, *A Study on Transcutaneuos Infrared Rays Communication and Energy Transmission for Totally Implantable Computer,* Okoji Hai, et al., pp. 1-68.

* cited by examiner

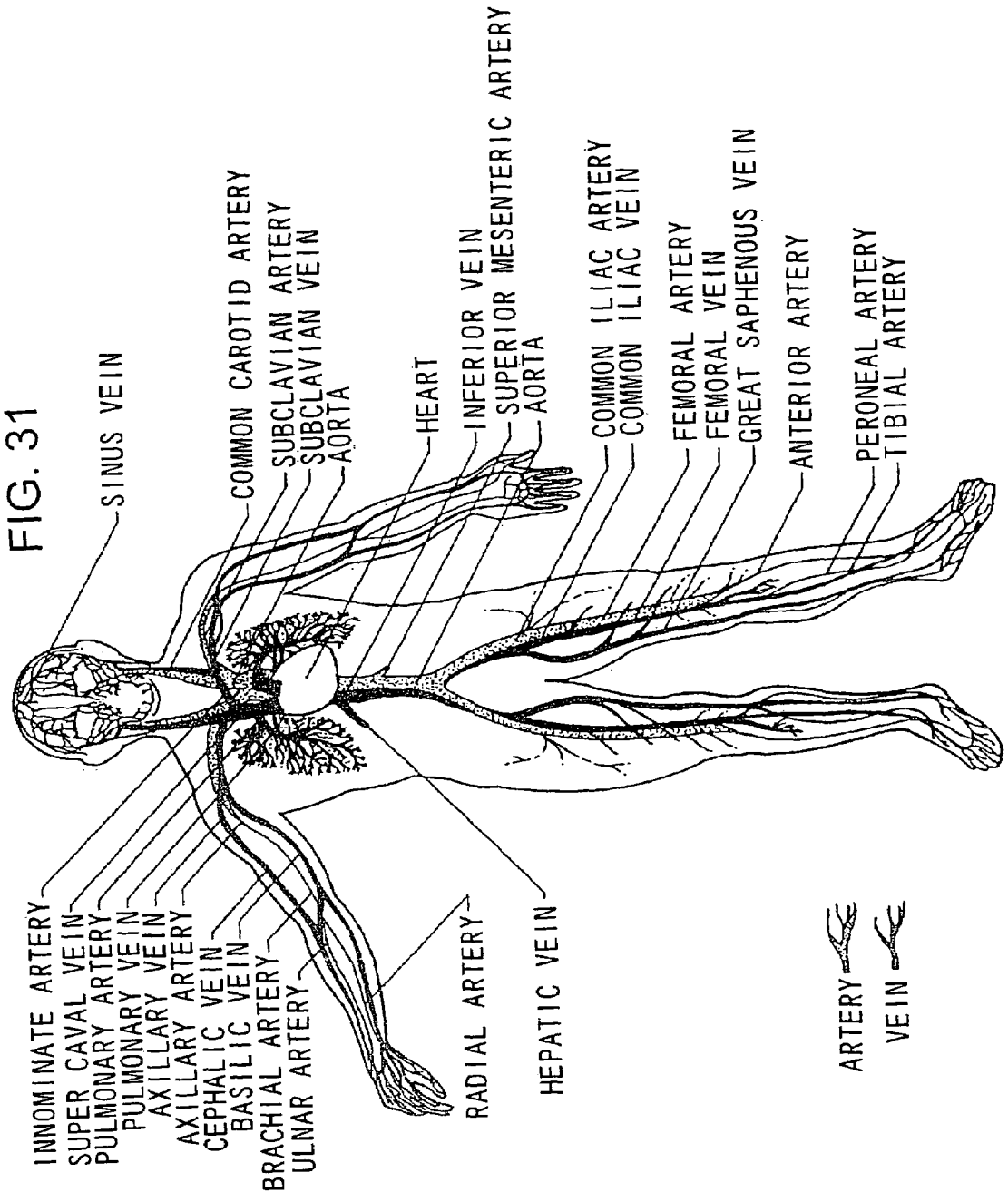

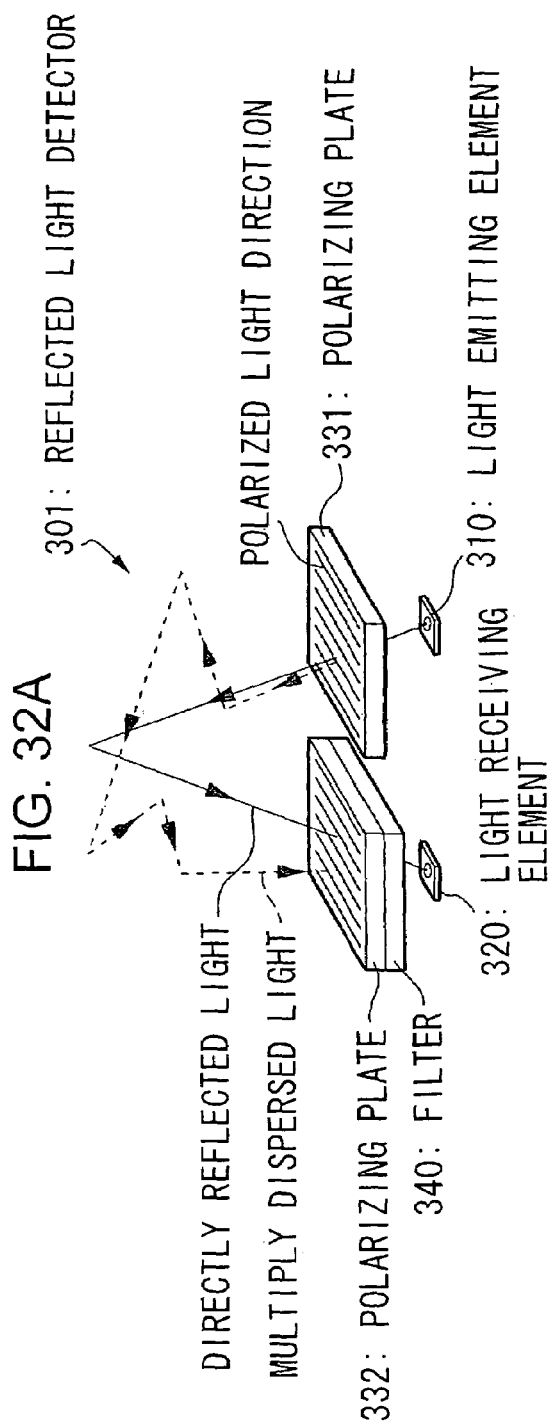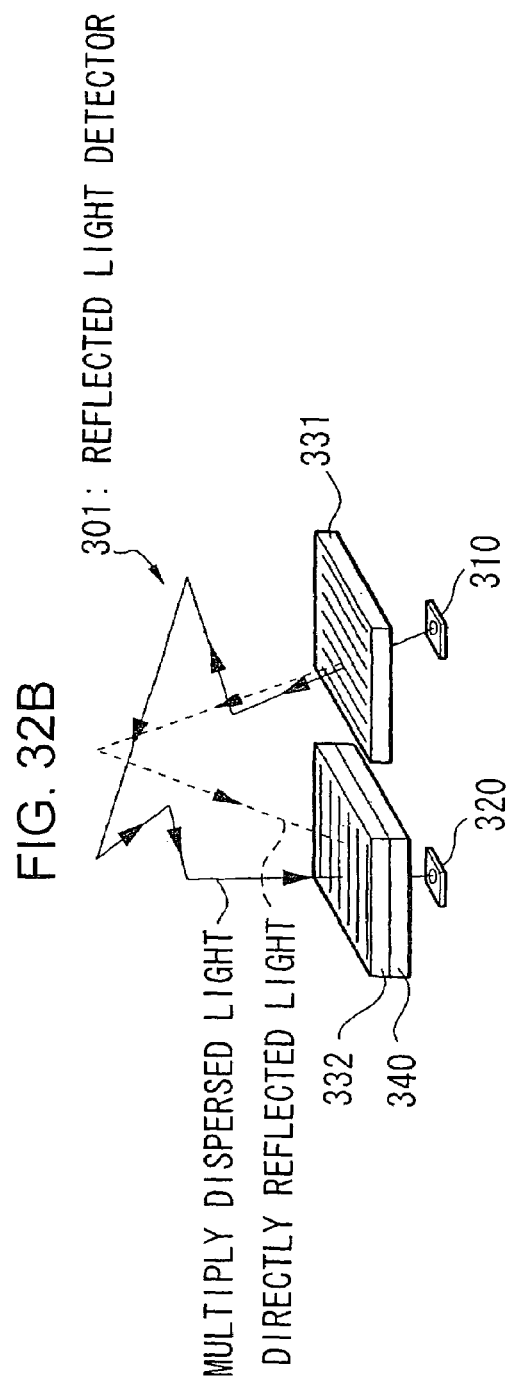

EXTERNAL LIGHT SPECTRUM

MIRROR REFLECTION COEFFICIENT

PD UNIT SENSITIVITY

FILTER CHARACTERISTICS

SENSITIVITY OF PD COMBINED WITH FILTER

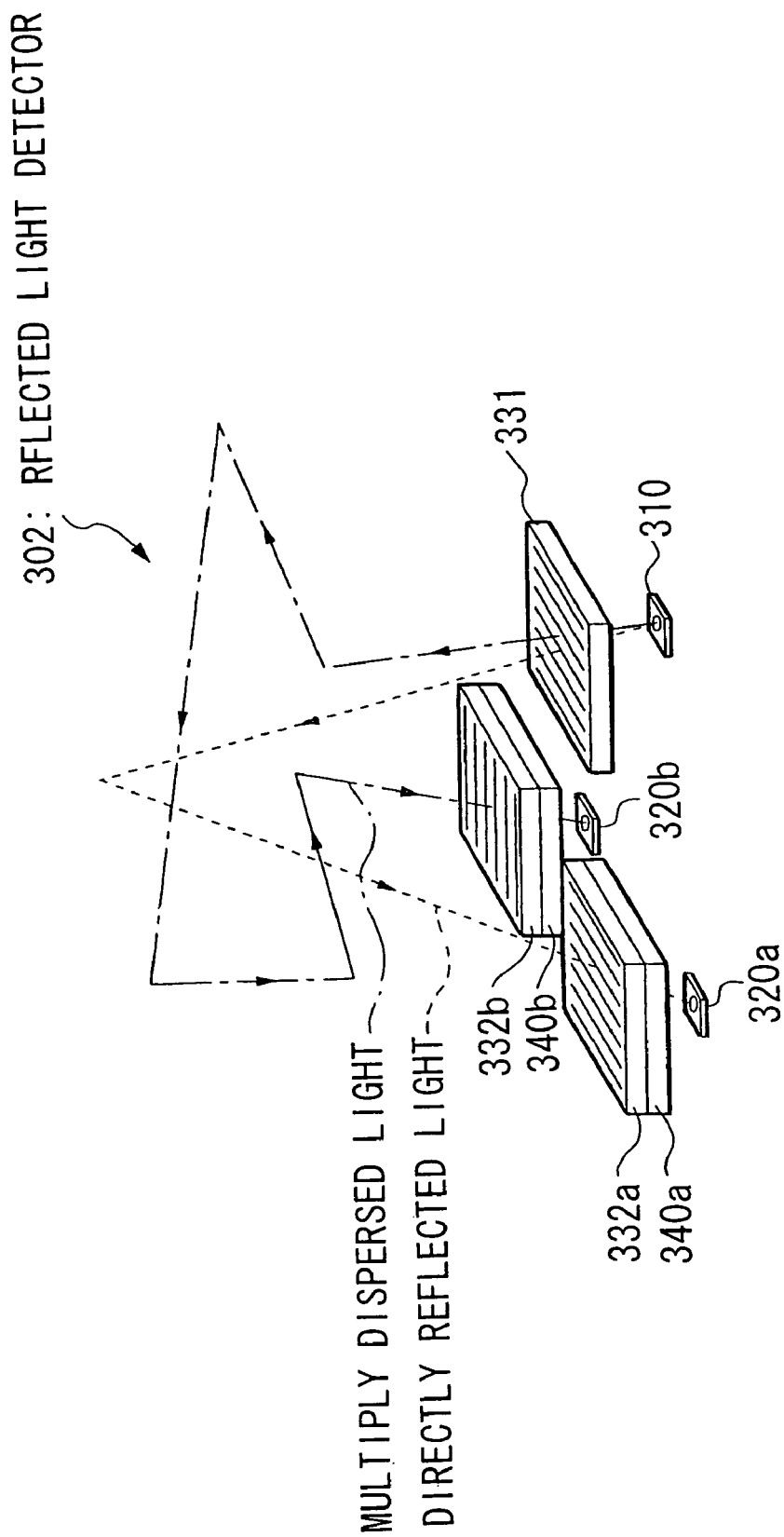

400: SENSOR UNIT

POLARIZED LIGHT COMMUNICATION DEVICE, TRANSMITTER, LASER, POLARIZED LIGHT COMMUNICATION DEVICE FOR PHYSIOLOGICAL USE, REFLECTED LIGHT DETECTOR AND PULSE WAVE DETECTING DEVICE

This application is a U.S. National phase application under 35 USC 371 of International Application PCT/JP98/01992 filed Apr. 30, 1998.

BACKGROUND OF THE INVENTION

1. Technical Field

The present invention relates to a polarized light communication device which employs polarized laser light as a transmission signal, and, in particular, to a polarized light communication device optimally employed for communication between a strongly dispersing medium, such as the human body, and the external environment. The present invention further relates to a reflected light detector optimally employed when obtaining information relating to the dispersing medium's flow, etc., and to a pulse wave detecting device which uses this detector to obtain the pulse wave in the body.

2. Background of the Invention

In conventional wireless communication, radio waves are typically employed to carry out communication. However, wireless data communications with faster forwarding rates are needed, and new frequencies must be developed. In addition, progress has been made in the radio wave field toward realizing the practical application of semi-millimeter and millimeter waves.

At the same time, light, which is not classified as radio waves under the law, has been increasingly used for wireless communications. In wireless data communications employing light, it is possible to offer high speed data communications using a broad band not regulated as radio waves. Since light characteristically does not pass through non-transparent objects such as walls, it is suitable for short-distance data communications, or wireless LAN systems confined to one room. Currently, the most representative methods from among wireless communication methods using infrared are the IrDA (Infrared Data Association) types of infrared data communication function. These consists of an infrared light emitting diode and a light receiving element, and can realize data conversion at a speed of from 115.2 kbps to 4 Mbps. Although this technology has a short communication distance of 1 m or less, its major feature is its ability to provide wireless data communications at low cost.

There is need to develop from now optical wireless data communications capable of a larger forwarding capacity and a longer communication distance. However, when using a light emitting diode as the light source, a problem arises with respect to the effective utilization of the band since the light emitted from the light emitting diode has a wavelength width of 100 nm or more. Furthermore, since the LED is limited by the carrier life, modulation above 100 MHz is difficult. In order to resolve these problems, it is effective to use a semiconductor laser as the light source. If a semiconductor laser is employed, it becomes easy to obtain a wavelength width of 1 nm or less, while modulation of 1 GHz or more is possible in principle. However, erroneous operations caused by crossing may be a problem.

Unlike radio waves, light used as wireless carrier waves is not legally regulated. Thus, while light can be freely employed, interference between optical wireless devices employing the same wavelength may occur. For example, the IrDA method, which is a known form of optical wireless data communications, employs wavelengths in the range of 850 to 900 nm for the peak wavelength. Thus, while a semiconductor laser may be used to realize a communication device for long-distance, high-speed communications, interference will occur with the IrDA method when any wavelength in this 850 to 900 nm range is employed. The IrDA method is widely employed in computers currently in use. Accordingly, even if interference with the IrDA method used in these computers does not present a problem from a legal perspective, it must be avoided from the perspective of practical application.

In the medical field, a variety of sensors are used to detect the body's internal status in order to continually monitor an afflicted area. The ability to record and analyze phenomena occurring inside the body is extremely important both for clarifying physiological functions and for diagnosing and treating a variety of illnesses. A number of methods have been investigated for this purpose. When invasive conventional methods are used to directly measure signals generated inside the body, then a problem arises in that the measurements must be conducted at the hospital bedside. Conversely, when an attempt is made to conduct measurements of physiological phenomena under a natural environment in which the user is engaging in daily activities, then an indirect method of measurement must be employed. Thus, the signals within the body cannot be taken directly. Accordingly, with the objective of directly measuring the signals generated inside the body under a natural environment, an arrangement may be conceived in which the entire component needed for directly measuring the signal inside the body for a computer and measuring circuit is embedded in the body, such that the device is autonomously completed within the body. In this case, however, the method of communication between the device within the body and a device outside the body becomes a problem.

For example, if communication is carried out using wires, then not only is infection a concern, but the device may hinder the user's daily activities. Furthermore, if radio waves are used, then there is a chance that radio waves generated by other communication devices may have an effect. Moreover, in addition to wireless communication devices, electromagnetic waves are emitted by electronic devices or thunder, raising the possibility of erroneous operations being cause by these electromagnetic waves. In addition, radio waves can maintain their SN ratio when propagating over long distances, raising the problem of interception of or interference from the radio waves from another person. This type of problem occurs not only in the case of devices which perform physiological measurements, but also in the case of such physiological assisting means as pacemakers, artificial kidneys, or insulin pumps. In other words, when sending a monitoring signal from a physiological assisting means embedded in the body to a device outside the body, or when sending a control signal from the device outside the body to the physiological assisting means, communication must be carried out between the two devices. The problems which may occur in this case are exactly the same as those discussed above.

Therefore, in order to avoid the above-described problems, an approach may be considered in which a light emitting diode is used to strongly modulate light (infrared light). This strongly modulated light is then employed to carry out communication between the inside and the outside of the body (see The Institute of Electronics, Information and Communication Engineers Shinshu University Technical Journal October 1995, MBE 95–89). Specifically, as shown in FIG. 46, an infrared transmitting and receiving circuit may be connected to a serial interface between computer systems 131,134, located within and outside the body respectively. At the infrared transmitting and receiving signal circuit, transmitting circuits 132,136 transmit digital data output from the serial interface as infrared light. The infrared light received by receiving circuits 133,135 is converted to digital data and relayed to the computers. A CPU, memory, real-time clock with calendar, A/D converter, or serial interface for communication with the outside may be employed for computer system 131 inside the body, and may be miniaturized to about the size of a business card through surface mounting technology. Using the above-described device, it is possible to eliminate the problems encountered when using radio waves.

However, it has not been possible to realize full duplex communication when employing light as the transmission signal for communicating between the inside and the outside of the body. This point will be explained below.

FIG. 45 is an example of a communication device for sending strongly modulated light as a transmission signal between the inside and the outside of the body. Physiological function assisting means 201 is embedded inside the body. Transmitter 211, provided to physiological function assisting means 201, emits strongly modulated light a by controlling the amount of light emitted by the light emitting diode. Receiver 202 of control means 222 which is outside the body receives light a emitted from transmitter 211 of physiological function assisting means 201. Meanwhile, receiver 212 of physiological function assisting means 201 receives strongly modulated light (not shown) emitted from transmitter 221 of external control means 202.

However, the body consists of a medium in which dispersion is extremely large (strongly dispersing medium), and is complexly formed of such sources of dispersion as body fluids, cells, and tissues. Therefore, light a preceding through the body is gradually dispersed in a variety of directions. As a result, as shown in FIG. 14, a portion of light a emitted by transmitter 211 of the internal assisting means reaches receiver 212 of internal assisting means 201. As a result, when internal transmitter 211 internal receiver 212 is sending a light signal, it is not able to receive light signals. In other words, only half duplex communication, in which only unidirectional communications can be performed simultaneously, is realized. Thus, it was not possible to realize full duplex communication in which communication in both the sending and receiving directions can be performed simultaneously.

Full duplex communication is the required method in the case where urgent controls or warnings may be required. For example, an environmental change may occur as a physiological function assisting means is sending data on physiological measurement data, such that urgent control of the physiological function assisting means must be provided from the outside. If full duplex communication cannot be carried out in this case, then even if an attempt is made to send commands or data to the device inside the body from the transmitter on the device outside the body, it is necessary to wait until transmission and receipt of the aforementioned measured data is completed. Since it may be urgent that control of the device inside the body be performed, the delay of the transmission or receipt operation constitutes a serious problem. Thus, full duplex communication are a necessity.

In addition, in a communications signal which passes through a strongly dispersing medium such as the body, the quantity of light which is received by the receiver is a very small proportion with respect to the quantity of light emitted by the transmitter. In order to compensate for this, it is necessary to sufficiently increase the amount of light emitted. Thus, a large amount of electrical power is required. When transmitting from outside to inside the body, the outside transmitter is able to use a large amount of electric power. In contrast, there is a limit to the amount of electric power which can be used by the device inside the body during transmitting from within to outside the body. Thus, in view of practical use, it is not desirable that the transmitter consume a large amount of power.

Moreover, it has been reported that when using a light emitting diode as the light source, considerable damping occurs upon passage through the skin (see The Institute of Electronics, Information and Communication Engineers, MBE-97-5 "Dermal optical telemetry system using laser diode", IJO, et al).

A device for detecting the radial arterial wave is available as one example of a conventional device for detecting pulse waves. In this type of device, changes in pressure at the skin surface in the vicinity of the radial artery are detected using a pressure sensor. The pulse wave is measured in this way. Since changes in the pressure applied to the sensor placed on the surface of the skin over the radial artery are detected, it is necessary to apply a pressing force of 30 to 80 mmHg in order to carry out a stable pulse wave detection. Accordingly, this has been problematic since the pressure felt by the test subject is large.

For example, in the invention disclosed in U.S. Pat. No. 4,951,679, a pressure sensor disposed near the redial artery is pressed against the arm, the pressing force is then sequentially varied, and the pressing force at which the amplitude of the detected signal is greatest is detected. The pulse wave detection is then carried out at this pressing force. In this case, the optimal pressing force can be detected so that the application of a greater than necessary force can be avoided. Nevertheless, however, it is still necessary to apply a specific amount of force on the arm, so that the subject still feels a strong pressure sensation.

In contrast, examples of pulse wave detecting devices which do not require the application of a strong pressing force include devices using ultrasonic waves or light (infrared, laser, etc.). In pulse wave detecting devices using ultrasonic wave reflection, the pulse wave is measured by bringing a probe emitting ultrasonic waves into contact with the user's arm from the outside, and then receiving the ultrasonic waves reflected by arterial vessels and the like at the probe.

In pulse wave detecting devices which detect the pulse wave using light, light is sent from a light emitting diode into the body, and the amount of light reflected (light reflected by subdermal tissues, etc.) is detected. A portion of the light emitted from the light emitting diode in this case is absorbed by the hemoglobin in the blood vessels. Thus, the amount of reflected light is related to the amount of blood in the blood vessels, and is detected as the pulse wave.

In conventional pulse wave detecting devices employing ultrasonic waves, the value detected for the reflected wave will vary according to the angle formed between the blood flow and the probe where the ultrasonic wave is sent and received. It is difficult to maintain the probe at a fixed angle with respect to blood flow during operation, however, so that a stable pulse wave measurement is difficult to achieve. For example, when the probe is in contact with the user's arm on the palm side, it becomes difficult to detect the pulse wave if the position of the probe is displaced by just a few millimeters with respect to the arterial vessels. Moreover, when the probe is placed in contact with the back of the user's arm, then it is not possible to maintain the S/N required for detecting the pulse wave.

In addition, even in a device which employs a laser or light emitting diode, it is difficult to discriminate between the attributes such as wavelength, phase, or degree of polarization which belong to the reflected light, and the attributes which belong to natural light or various illuminating lights. As a result, an impact from natural or illuminating light tends to be present, so that stable and accurate detection of the pulse wave becomes problematic.

For example, a method is conventionally known in which the dispersing medium is irradiated with light (electromagnetic waves), the reflected light is detected at the light receiving element, and temporal changes in the flow quantity of the dispersing medium are detected. Note that "dispersing medium" as used here means a substance having the property of dispersing iremitted light, and includes not only fluids and flows containing a mixture of microparticles, but also bodies such as the human body. In the case of the body, the body is irradiated with light, and a light receiving element then detects the light which is reflected. As a result, information, such as pulse wave information, relating to the body can be obtained. This method is particularly significant because detection of the pulse wave can be carried out in a non-invasive manner.

In a method in which a dispersing medium is irradiated with light, the reflected light is detected, and information relating to the dispersing medium is obtained, if the light receiving element detects not only the reflected light component, but also the external light component, then it is not possible to accurately obtain information relating to the dispersing medium. Accordingly, the important technique in this method is the reduction of the impact from external light. External light is typically of an extremely strong intensity such as sunlight, or light in which the intensity has been modulated to a commercial frequency, as in the case of florescent lights. Moreover, it should be noted that even if the intensity of the external light is constant, the intensity of the external light component detected by the light receiving element will change if the light receiving component is moved.

If the light quantity which is emitted on the dispersing medium is increased to an extent such that the influence of the external light can be ignored, then this problem can be resolved at once. However, increasing the light quantity is not practical when one takes into consideration the properties of the light emitting element which emits the light, the amount of power it consumes, and safety with respect to the body when obtaining information relating thereto. Accordingly, it will be necessary to consider this problem below, with the assumption that there is an upper limit to the amount of light emitted.

Based on this assumption, in order to reduce the influence of external light, one may first consider using a filter to remove unnecessary wavelengths components from the light detected by the light receiving element. If a semiconductor laser is used, then light in a narrow wavelength band can be emitted. Therefore, if a glass filter which transmits only light of this wavelength band is disposed in front of the light receiving component, it should be possible to reduce the influence of the external light.

In order to reduce the influence of the external light, a second method may be considered in which, after taking into consideration the properties of the dispersing medium, the wavelength of the light employed is selected to be in a band in which the effect of external light is not readily imparted. For example, light in the infrared region readily passes through the body, while light having a short wavelength, such as blue light, is readily absorbed. Therefore, when obtaining information related to the body, a blue light LED is used as the light source, while a photodiode using GaP or GaAs which is sensitive to the blue light region is used as the light receiving element. As a result, it is possible to decrease the impact of external light.

However, the first method, employing the glass filter, has the following problems. Namely, it is not possible to realize sharp characteristics such as those when transmitting only the wavelength band of the semiconductor laser. While such characteristics can be realized with an interference filter, the production cost thereof is typically high. The characteristics of the transmission wavelength band must be matched to the semiconductor laser used. Thus, costs rise considerably.

On the other hand, in the second method, in which the wavelength of the light is selected to be in a range which is not readily influenced by external light, a suitable light source and light receiving element may not necessarily be available depending on the wavelength of the selected band. For example, when obtaining information relating to the body, a blue LED and a photo diode sensitive to blue light are employed. However, in general, these devices are not only expensive, but they consume a large amount of power and are poorly efficient with respect to photoelectric conversion. In addition, the fact that blue light is readily absorbed by the body is a positive effect with respect to reducing the influence of external light, but a negative effect with respect to its difficulty in reaching deep areas in the skin. For this reason, when obtaining information relating to deep areas under the skin, a large amount of light is needed, contradicting the assumption stated above.

Particular problems exist when obtaining information related to the body. These include the superimposition of a motion component should the body move, so that the information obtained is not accurate, or a marked deterioration in detection sensitivity when the air temperature is low due to contraction of the capillary vessels at the skin surface.

DISCLOSURE OF THE INVENTION

The present invention was conceived in consideration of the above-described circumstances, and has as its objective the provision of a polarized light communication device, transmitter, planar emission laser, and polarized light communication device for physiological use, wherein full duplex communication can be carried out and there is little damping when communicating between the inside and the outside of a strongly dispersing medium such as a living body.

Accordingly, the polarized light communication device for resolving the aforementioned problems is provided with a transmitter for modulating the plane of polarization of the laser light, and then emitting the result as a transmission signal; and a receiver having a light receiving means which selectively receives light of a specific polarization state. It is preferable to communicate between the inside and the outside of a strongly dispersing medium like a living body by disposing one of either the transmitter or receiver inside the strongly dispersing medium. It is also acceptable to employ this polarized light communication device in unidirectional communication from the outside of the strongly dispersing medium to the inside the strongly dispersing medium, by disposing the receiver inside the strongly dispersing medium and the transmitter outside the strongly dispersing medium. It is preferable to dispose the internal transmitting/receiving device consisting of the aforementioned transmitter and receiver inside the strongly dispersing medium, and to dispose the external transmitting/receiving device consisting of the aforementioned transmitter and receiver outside the strongly dispersing medium. In this way, full duplex communication can be performed by disposing two sets of transmitters/receivers inside and outside the strongly dispersing medium.

As a result, the present invention uses a polarized light modulating method as the transmission signal, so that the two sets of transmission signals do not interfere with one another even when performing full duplex communication via a strongly dispersing medium. This is because it is a property of light which is strongly dispersed in a strongly dispersing medium that it does not maintain a state of polarization.

In the polarized light communication device according to the present invention, it is preferable to dispose an internal transmitting/receiving device in the strongly dispersing medium, the internal transmitting/receiving device consisting of the aforementioned transmitter and a light quantity receiver which has a received light quantity detecting means which outputs a signal in response to the received light quantity; and to dispose an external transmitting/receiving device outside the body, the external transmitting/receiving device consisting of the aforementioned receiver and a light intensity transmitter which modulates the amount of light emitted and emits it as a transmission signal; with full duplex communication being carried out between the internal transmitting/receiving device and the external transmitting/receiving device. The reason for making one communication a polarized light modulating type communication and making the other communication a light intensity modulating type communication is because this is effective in reducing the transmission power. In addition, full duplex communication between an internal transmitting/receiving device and an external transmitting/receiving device can be carried out by disposing in the strongly dispersing medium an internal transmitting/receiving device, consisting of the aforementioned receiver and a light intensity transmitter for modulating the quantity of emitted light and emitting this result as the transmission signal, and disposing outside the body an external transmitting/receiving device, consisting of the aforementioned transmitter and a light quantity receiver having a received light quantity detecting means for outputting a signal in response to the quantity of received light.

It is preferable that the transmitter in the present invention's polarized light communication device be provided with a light emitting means which generates a plurality of planar emission laser elements having different polarized light directions on the same semiconductor substrate, and a driving means for selectively supplying current to these planar emission laser elements. As a result, the transmitter embedded in the body can be made extremely small, and the amount of powder consumed can be reduced. For the same reason, it is preferable to use a planar emission laser as the light source for the light intensity transmitter.

In the polarized light communication device according to the present invention, it is preferable that the driving means drive only a portion of the planar emission lasers in the light emitting means during the regular operation of the transmitter. It is further preferable that when the planar emission lasers driven by the driving means are no longer in a specific state, that the driving means then drive planar emission lasers in the light emitting means which were not used during regular operation. In other words, a plurality of planar emission lasers which serve as the light source are provided on the same semiconductor substrate, with a portion of these designated as the reserve light source. As a result, the reliability of the transmitter/receiver embedded in the body is improved, reducing the need for repairs.

In the polarized light communication device according to the present invention, it is preferable that the light source be an arrangement in which a plurality of planar emission laser elements having different polarized light directions are formed on the same semiconductor substrate. As a result, it is possible to make a polarized light modulating type transmitter that is extremely small, thus reducing the power consumed by the transmitter. It is preferable to modulate the polarization plane of the laser light and use the result as the transmission signal, by associating the plurality of planar emission laser elements with transmission signals, and selectively supplying power thereto.

The present invention's polarized light communication device for physiological use is provided with a transmitter which is embedded in the body, this embedded transmitter provided inside the body and modulating the polarization plane of the laser light and emitting it as a transmission signal; and a receiver which may be attached to the body, the receiver provided outside the body and equipped with a light receiving means for selectively receiving light of a specific polarization state, a display for providing a display corresponding to the received signal of the light receiving means, and an attaching means for fixing the light receiving means to the body so that the light receiving means receives the light emitted from the transmitter embedded in the body.

It is preferable that the present invention's polarized light communication device for physiological use be equipped with a second light receiving means that is provided inside the embedded transmitter and selectively receives light in a specific polarization state, and a second transmitter that is provided inside the receiver attached to the body and modulates the polarization plane of the laser light and emits the result as a transmission signal to the second light receiving means, the polarized light communication device carrying out full duplex communication between the embedded transmitter and the receiver attached to the body.

As explained above, by means of the present invention, it is possible to avoid disturbance light or interference between light communications receivers, and enable full duplex communication to be carried out between the inside and the outside of a strongly dispersing medium. Because laser light is used in this embodiment, there is little damping of the light used in the measurements when it passes through the skin.

The present invention was conceived in consideration of the above-described circumstances, and has as its objective the provision of a pulse wave detecting device capable of accurate and stable detection of the pulse wave without being impacted by external light or the inexperience of the operator.

In order to resolve the above-described problems, the present invention's pulse wave detecting device is provided with a transmitting means for emitting a specific wave; a receiving means for receiving the wave emitted by the transmitting means and outputting it as a signal; a transmission path measuring means for measuring the positional relationship between the transmission path of the wave and the cross-section of the arterial vessel based on the state of the signal received by the receiving means; and a notifying means for notifying the user of the results of measurements by the transmission path measuring means; the pulse wave detecting device detecting the pulse wave based on the signal output by the receiving means. It is also preferable to provide a position changing means for changing the relative positional relationship of the receiving means and the transmitting means to a direction so that the receiving state improves, based on the results of measurements by the transmission path measuring means.

The present invention's pulse wave detecting device is provided with a transmitting means for emitting a specific wave; a receiving means for receiving a wave emitted by the transmitting means and outputting it as a signal; a transmission path measuring means for measuring the positional relationship between the transmission path of the wave and the cross-section of the arterial vessel based on the state of the signal received by the receiving means; and a position changing means for changing the relative positional relationship of the receiving means and the transmitting means to a direction so that the receiving state improves, based on the results of measurements by the transmission path measuring means; wherein the pulse wave detecting device detects the pulse wave based on the signal output from the receiving means. In addition, it is preferable that the pulse wave detecting device have a body motion component detecting means for detecting body motion components in the body where the pulse wave is being measured, and that the pulse wave be detected after removing the body motion component detected by the body motion component detecting means from the pulse wave received by the receiving means. In addition, it is preferable that the wave be light, laser light, or polarized laser light.

It is preferable a ring-shaped attaching member be provided that attaches to the body in which detection is being performed, and that that the transmitting means and the receiving means attach to the attaching member. It is preferable that this attaching member wrap around the arm, with the position of the transmitting means and the receiving means and the direction of emission of the wave being set so that the transmission path passes between the radius and ulna bones in a cross section of the arm.

As a result, it is possible to perform a stable and highly accurate pulse wave detection which is not influenced by movements of the user's body, the degree of training of the operator, or disturbance light.

The present invention was conceived in consideration of the above-described circumstances, and has as its objective the provision of a reflected light detector in which the impact of external light is reduced by employing polarized light and a light receiving element using an optical resonator, and to the provision of a pulse wave detecting device using this detector.

In order to resolve the above-described problems, the present invention's reflected light detector is provided with a light emitting means for emitting light (electromagnetic wave) onto a dispersing medium; a first polarizing means for polarizing light generated by the light emitting means; a second polarizing means for incidenting the light reflected by the dispersing medium and permitting passage of light components polarized in a specific direction; and a light receiving means for receiving light which has passed through the second light polarizing means. The light receiving means consists of a light resonating means for resonating the incidented light, and an outputting means for outputting a signal proportional to the light resonated by the light resonating means.

As a result of this design, the light generated by the light emitting means is polarized by the first light polarizing means and emitted onto the dispersing medium. Of this reflected light, only light having components polarized in a specific direction pass through the second polarizing means and incident on the light receiving means. Of the light falling on the light receiving means, only light in a specific wavelength region is selected by the light resonating means, and a signal corresponding to this light only is output by the outputting means. The wavelength of the light emitted by the light emitting means and the wavelength of the light resonated by the light resonating means are selected after taking into consideration the properties of the dispersing medium, so as to be in a range which is not readily effected by external light, and so that the impact of external light is reduced when the wavelengths are made to coincide.

A semiconductor laser consisting of light reflecting layers and an active layer inserted therebetween is employed as the light emitting means, while a photo diode consisting of light reflecting layers and a depletion layer inserted therebetween is employed for the light receiving means. The light resonating means is formed of two light reflecting layers. The outputting means is designed such that a current is generated in response to the amount of light absorbed by the depletion layer, while the light emitting means and the light receiving means are formed onto the same semiconductor substrate. As a result, it is possible to easily bring together the light emitting wavelength and the resonating wavelength. In addition, by controlling the thickness of the light reflecting layer, it is possible to optionally set both wavelengths.

By optionally setting the polarization direction on the light emitting side and the polarization direction on the polarizing side of the light receiving side, it is possible to optimally select the component of the reflected light which is received. For example, if both polarization directions are the same, then it is possible to detect components due to directly reflected light even in a strongly dispersing medium. Conversely, even if the polarization directions are perpendicular to one another (or reversed), it is possible to detect the components due to dispersed light.

As explained above, due to the design of the present invention in which light is emitted on a dispersing medium and the light reflected by the medium is detected, information related to the dispersing medium can be obtained with little impact from external light.

BRIEF DESCRIPTION OF THE FIGURES

FIG. 31 is a diagram of the human body showing arteries and veins.

FIG. 32($a$) is a rough structural diagram of the reflected light detector according to an eighth embodiment of the present invention, showing the design in the case where the directly reflected light component is detected; FIG. 32 ($b$) is a rough structural diagram in the case where the scattered light component is detected.

FIG. 33($b$) is an electrical circuit for sending out an output.

FIG. 38 is a rough structural diagram showing the structure of the reflected light detector according to the ninth embodiment of the present invention.

PREFERRED EMBODIMENTS OF THE PRESENT INVENTION

Preferred embodiments of the present invention will now be explained with reference to the accompanying figures.

A: Embodiment 1

(1) Structure

Figure 1:
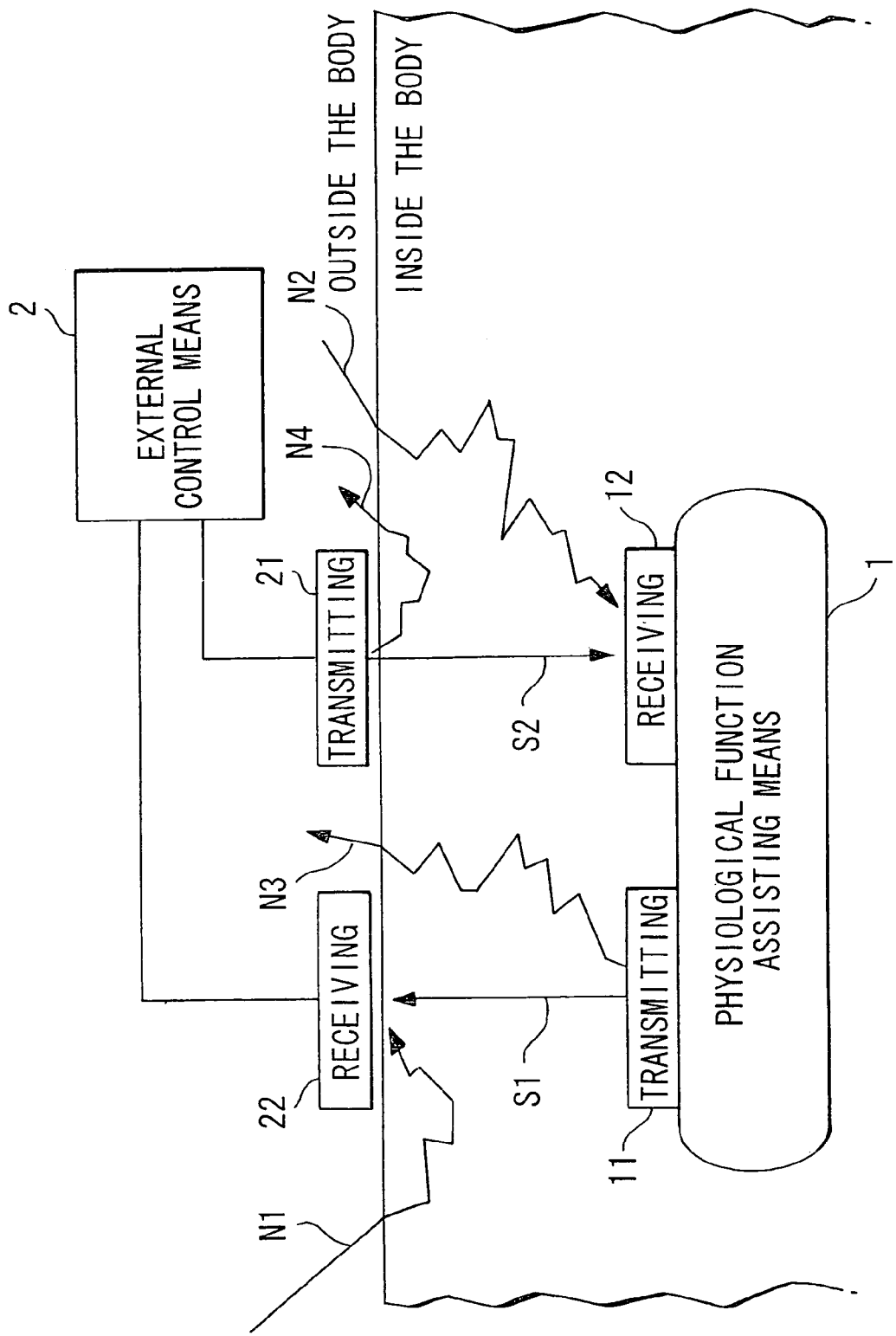
FIG. 1 is a block diagram showing the entire structure of the polarized light communication device according to the first embodiment of the present invention.

FIG. 1 is a block diagram showing the overall structure of the polarized light communication device according to the first embodiment. Physiological function assisting means 1 is a device, such as an artificial kidney or insulin pump, for augmenting a physiological function, and is embedded in the body. Physiological function assisting means 1, which is embedded in the body and continuously monitors a morbid area, may employ a variety of sensors to detect the body's internal state. Physiological function assisting means 1 is provided with a transmitter 11 and receiver 12 for communicating with external control means 2. While the term "internal" as used here refers to the inside of the human body, it may also encompass the inside of an animal's body, or the inside of a strongly dispersing medium which strongly disperses light.

External control means 2 controls physiological function assisting means 1, which is embedded in the body, from the outside, and may, for example, be a computer. Outside the body, external control means 2 receives internal body information detected by physiological function assisting means 1, and displays and stores this internal-information. External control means 2 is provided with a transmitter 21 and receiver 22 for communicating with physiological function assisting means 1.

Transmitters 11 and 21 modulate the polarization plane of the laser light, and emit it as a transmission signal. Receivers 12, 22 are provided with a light receiving means for selectively receiving light which is in a specific polarization state. Receivers 12, 22 output electrical signals corresponding to the polarization state (polarization angle and ellipticity) of the light which they each receive.

Modulation of the polarization plane will now be explained. Polarized light contains linearly polarized light, as well as circular or elliptical light polarized in the clockwise or counterclockwise direction, for example. When modulating the polarization plane, the polarized light state is changed in response to a modulation signal. For example, in the case of linearly polarized light, linearly polarized light rays perpendicular to one another are assigned a signal of "1" or "0", and modulation is carried out by switching the polarization planes. When clockwise and counterclockwise circularly polarized light is used, then signals "1" and "0" are assigned, and modulation is carried out by switching the polarization direction. At the receiver, demodulation is carried out by detecting the direction in which the light is polarized.

The typical semiconductor laser can only emit linearly polarized light. If, however, a ¼ wavelength plate is used, then linearly polarized light can be converted to circularly polarized light. In other words, if a ¼ wavelength plate is disposed in a position inclined at a 45 degree angle with respect to the light axis of the linearly polarized light, then, by switching the direction of the linearly polarized light, it is possible to generate light which is circularly polarized in the clockwise or counterclockwise direction. In a vertical resonator planar light emitting semiconductor laser (hereinafter, planar emission laser), the polarization plane can be modulated without employing a ¼ wavelength plate. This planar emission laser will be explained below.

When receiving a signal, the process is the reverse of that when transmitting a signal. Namely, a ¼ wavelength plate is used to convert circularly polarized light into linearly polarized light having two axes. Demodulation can then be carried out by detecting the size of the polarized light components of each axis. For example, the x and y axes are determined at positions which is inclined ±45° from the optical axis of a ¼ wavelength plate, and a polarized light beam splitter may be placed so as to reflect polarized light components which are parallel to the x-axis and to transmit polarized light components which are parallel to the y-axis. A light detector may then be provided for detecting the polarized light components which are separated as a result. If the output from the light detector is input to a differential amplifier, then it is possible to amplify only the component in which the polarized light has been modulated, thereby removing same-phase components effected by non-polarized light disturbances. As a result, it is possible to obtain a signal having a good SN ratio.

(2) Operation

The main operations of this polarized light communication device will now be explained with reference to FIG. 1. Laser lights S1, S2 emitted by transmitter 11 and transmitter 21 are both laser lights in which the polarization plane has been modulated, so that the light intensity is constant. Disturbance light N1 is light emitted by communication devices or florescent lights disposed in the vicinity of the polarized light communication device. Disturbance light N1 contains linearly polarized light such as sunlight, and light which has been strongly modulated by an existing technique. Receiver 22 receives laser light S1 emitted by transmitter 11 and disturbance light N1. In this case, disturbance light N1 is strongly modulated non-polarized light. Thus, even if this non-polarized disturbance light falls on receiver 22, it has no effect on the alternating components of the polarized light state in the plane of the light received at receiver 22. Namely, even if non-polarized disturbance light falls on receiver 22, there is no effect on the polarization state of the plane of the light received at receiver 22. This operation is the same when receiver 12 receives laser light S2 and disturbance light N2.

Effect of Embodiment

As a result of the above operation, this polarized light communication device uses light in which the polarization plane has been modulated as the transmission signal. Thus, it is not readily effected by strongly modulated light generated by existing optical communication devices or the like. As a result, it is possible to realize safer communication between the inside and the outside of the body. Conversely, even if existing communication devices which strongly modulate light are present near this polarized light communication device, the light generated by the polarized light communication device does not effect these communication devices.

The preceding example explained the case where two-way communications are carried out between an external control means 2 located outside the body and a physiological function assisting means 1 located inside the body. However, the present invention is not limited thereto. For example, the present invention's polarized light communication device may be employed for one-way communication from the external control means 2 located outside the body to the internal physiological function assisting means 1.

As one example of this type of application, a heart pacemaker may be employed as physiological function assisting means 1. In this case, the heart pacemaker used as physiological function assisting means 1 in this embodiment is designed to receive a specific signal from transmitter 21 of external control means 2. As a result, control for precisely adjusting the timing at which regulating pulses are generated can be performed from the outside. When carrying out feedback control, for example, the user's respiration state, state of transfer of blood within the arteries, heart rate and electrocardiogram may all be monitored by separate sensors, and the control state of the heart pacemaker changed based on the results of this observation.

By using light having a modified polarization state as the transmission signal for a physiological function assisting means such as a heart pacemaker, radio waves, various illuminated lights and natural light have almost no impact. Thus, a higher degree of safety and reliability can be achieved.

B. Embodiment 2

(1) Structure

Figure 2:
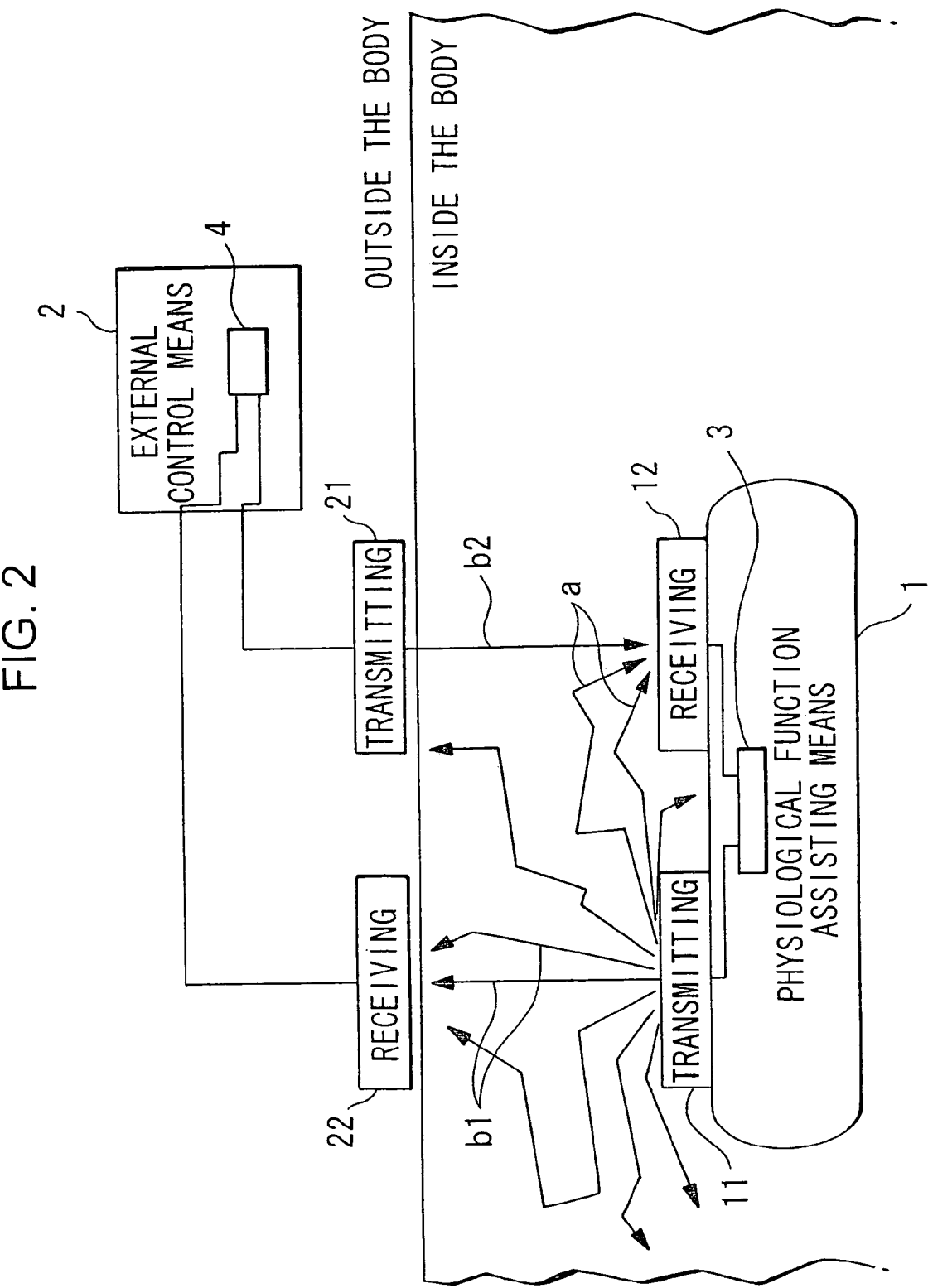
FIG. 2 is a block diagram showing the operation and structure of the polarized light communication device according to the same embodiment.

FIG. 2 is a block diagram showing the operation and structure of the polarized light communication device according to this embodiment. As in the polarized light communication device according to the first embodiment, this polarized light communication device employs light having a modified polarization state as the transmission signal. However, this polarized light communication device differs from that of the first embodiment in that it carries out full duplex communication between physiological function assisting means 1 and external control means 2. This polarized light communication device differs from that shown in FIG. 1 in that the physiological function assisting means 1 is equipped with an internal transmission/reception control means 3, and external control means 2 is equipped with an external transmission/reception control means 4. Other structures of the device are the same as those shown in FIG. 1. Internal transmission/reception control means 3 controls the operation of transmitter 11 and receiver 12. External transmitter/receiver control means 4 controls the operation of transmitter 21 and receiver 22.

Full duplex communication is realized by coordinating operation of internal transmitter/receiver control means 3 and external transmitter/receiver control means 4, simultaneously employing transmitter 11 and receiver 22, and transmitter 21 and receiver 12.

(2) Operation

The specific operations of this polarized light communication device will now be explained with reference to FIG. 2. Transmitters 11,21 emit laser light in which the polarization plane has been modulated. Of the laser light emitted by transmitter 11,12, light b1,b2 which was not dispersed inside the body or which has a small dispersion angle (i.e., the degree of dispersion is small) respectively, reaches receivers 22,12 with the polarization state thereof maintained. Light which progresses directly in this way is referred to as quasi-rectilinear propagation light.

On the other hand, of the laser light emitted by transmitter 11,21, light a, which has been strongly dispersed by strongly dispersing substances inside the body, also reaches receivers 12,22. For this reason, when attempting full duplex communication using a signal in which the light has been strongly modulated for the transmission signal, a portion of the light signal emitted from within the body to the outside is added to the light signal emitted from outside the body to the inside. Note that the same applies in the case of a light signal output from the inside to the outside of the body.

It is a property of a strongly dispersed light a that it does not maintain its polarization state. Namely, of the laser light emitted by transmitter 11 in this polarized light communication device, strongly dispersed light a is non-polarized light which does not maintain its polarization state. Accordingly, even if this non-polarized light falls on receiver 12, its impact on the state of reception and demodulation functions at receiver 12 is small. On the other hand, of the laser light emitted by transmitter 11, light b1 which was not dispersed in the body or which has a small dispersion angle reaches receiver 22 with the polarization state maintained. This phenomenon is the same in the case of laser light b2 emitted from transmitter 21 to receiver 12.

As a result, even if transmitter 11 and transmitter 21 simultaneously emit a transmission signal between the inside and the outside of the body in this polarized light communication device, the emitted light and the dispersed light do not effect the receiver on the emitting side. Thus, it is possible to realize full duplex communication in which transmission and reception are carried out simultaneously over two sets of communications paths between the inside and the outside of the body.

Accordingly, full duplex communication between the inside and the outside of the body can be carried out by means of this polarized light communication device. Thus, should a change in the environment of physiological function assisting means 1 occur while transmitter 11 is transmitting physiological measurement data, such that urgent control of physiological function assisting means 1 by external control means 2 becomes necessary, this control can be rapidly realized using transmitter 21 and receiver 12. In other words, since full duplex communication can be performed using this polarized light communication device, it is not necessary to wait for transmission or receipt of the measurement data currently being executed in order to send data or commands from transmitter 21 of external control means 2 to physiological function assisting means 1. Thus, the present invention's polarized light communication device can be applied to communication outside the body which must be conducted without the loss of any time.

Moreover, since the transmission signals of the two sets of communications paths do not interfere with one another in this polarized light communication device, the distance at which transmitter 11 and receiver 12 are disposed can be made extremely small, thus avoiding an enlargement in the external shape of physiological function assisting means 1 embedded inside the body.

B-1: Modification

In order to carry out full duplex communication between the inside and the outside of a strongly dispersing medium like the body, it is most ideal to employ a polarized light modulating method for both directions of two sets of communications paths. However, full duplex communication may also be realized by using modulation of the polarization plane on one communications path only, while light intensity modulation, in which the intensity of the light is modulated, is performed on the communications path in the other direction.

(1) Structure

Figure 3:
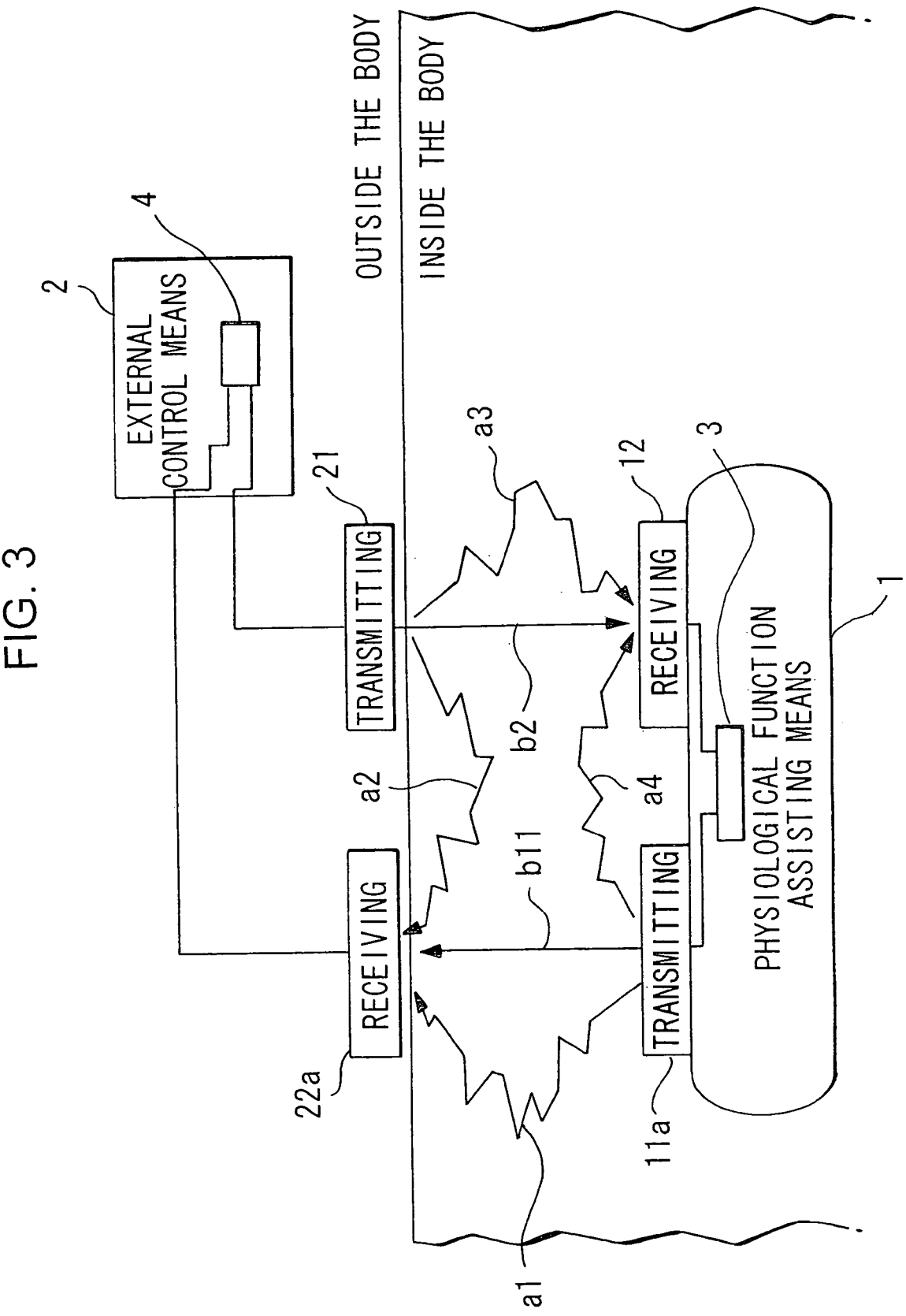
FIG. 3 is a block diagram showing the operation and structure of the polarized light communication device according to a modification of the first embodiment.

FIG. 3 is a block diagram showing the polarized light communication device according to this embodiment. The structure of this device differs from that shown in FIG. 2 in that transmitter 11a, which corresponds to transmitter 11, modulates the intensity of the light (emitted light quantity) and emits a transmission signal, and in that receiver 22a employs the received light's intensity (received light quantity) as the receiving signal. The other structures are the same as that of the polarized light communication device shown in FIG. 2.

(2) Operation

The operation of this polarized light communication device will now be explained with reference to FIG. 3. In summary, laser light b2, in which the polarization plane has been modified, is employed in communication from the outside to the inside of the body, while light b11, in which the light intensity has been modified, is employed in communication from the inside to the outside of the body.

Quasi-rectilinear propagation light b2 in the laser light emitted from transmitter 21 after modification of the polarization plane reaches receiver 12 with its polarization plane at the time of emission maintained. Of the laser light emitted from transmitter 21 after modulation of the polarization plane, component light a2,a3, which were strongly dispersed in the body, form non-polarized light. Light a3 falls on receiver 12. Of the light output by transmitter 11a, strongly modulated non-polarized light a4 which was dispersed inside the body also falls on receiver 12. However, light a3,a4 is non-polarized light, so that its effect on the reception state and demodulation function at receiver 12 is small. Thus, receiver 12 is able to carry out excellent demodulation based on light b2. In other words, in receiver 12, by detecting the difference in the polarization state of the received light, disturbance light a3,a4 can be removed as same phase components.

At the same time, of the light emitted from receiver 11a after being strongly modulated, quasi-rectilinear propagation light b11 and dispersed light a1 both reach receiver 22a. Since both quasi-rectilinear propagation light b11 and dispersed component light a1 almost simultaneously reach receiver 22a after the light intensity has been modulated by the same signal, it is possible for both to contribute as received signal components at receiver 22a. Of the light emitted from transmitter 21, component light a2 dispersed inside the body reaches receiver 22a. However, since this light is not modulated, it acts only as a simple direct current component with respect to receiver 22a. Thus, it can be easily removed.

As a result of the above actions, full duplex communication can be realized in the two transmission paths in this polarized light communication device by using polarization plane modulation on one communications path only, and light intensity modulation, in which the intensity of the light is modulated, for the other communications path.

In this polarized light communication device, of the light received by receiver 22a, light a1 dispersed inside the body and quasi-rectilinear propagation light b11 both become received signal components. Thus, the transmission signal can be effectively transmitted, and the power consumed by transmitter 11a reduced. This contrasts to the case where modulating the polarization plane, wherein the light strongly dispersed in the body does not maintain its polarization state, so that, even if it falls on receiver 12, it is removed as a non-polarized light component as in the case of light a3 for example, and does not become a signal component. In other words, this embodiment which employs light intensity modulation in communication from the inside to the outside of the body is considerably effective in making good use of the limited electrical power possessed by physiological function assisting means 1 embedded in the body, for full duplex communication between the inside and the outside of the body.

C: Specific Example of Transmitter

Transmitters 11, 21, and 11b employed in the present and preceding first embodiment will now be explained. In general, the output of a light emitting element can be modulated, while it is not typically the case that the polarization state can be modulated. However, this type of polarization modulating light emitting element can be realized with a single element, or with a combination of multiple elements. In this case, the polarization planes of two semiconductor lasers must be directed so as to be perpendicular to one another, and the light axes adjusted so that the illumination ranges of the respective semiconductor lasers match one another.

For example, if multiple elements are combined, then the direction of the polarization plane of the light emitted from the laser light source can be modulated with a rotary element employing a nematic liquid crystal. By combining a light source such as a regular semiconductor laser and another polarized light modulating element, it is possible to realize a transmitter according to the present invention. A Faraday rotator, liquid crystal or electro-optical element may be used as the polarization modulating element.

It is also possible to realize an element capable of modulating polarized light by using two semiconductor lasers, disposing them so that their respective polarization planes are perpendicular to one another, and then alternately driving them. In this case, the two semiconductor lasers must be accurately placed perpendicular to one another, and the light axes thereof adjusted so that the illumination ranges of the semiconductor lasers coincide.

However, when a plurality of elements are combined in this way, the transmitter becomes complicated and larger in size, and is therefore not suitable for insertion in the body as a component of physiological function assisting means 1. In this case, the response speed of the crystal is also not fast enough for use in communications.

At the same time, in a typical semiconductor laser, the polarization plane emits a constant linearly polarized light. If the design is modified, however, the laser can modulate the polarization plane. As an example of this, a vertical resonator planar emission semiconductor laser will now be explained.

Figure 4:
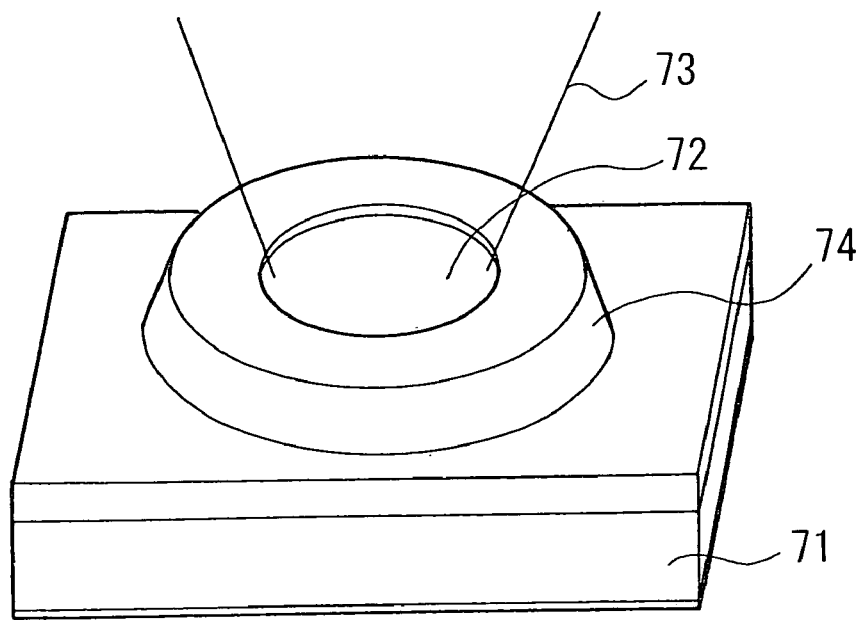
FIG. 4 is a perspective view showing the outer appearance of the planar emission laser used in the present invention's polarized light communication device.

FIG. 4 is a perspective view showing the outer appearance of a vertical resonator planar emission semiconductor laser (hereinafter referred to as a planar emission laser) which serves as respective light emitting means in transmitters 11, 21, and 11b. The characteristic of the planar emission laser is that laser light 73 is emitted from opening 72 perpendicular to substrate 71. The planar emission laser is formed by employing a photolithography technique to a semiconductor layer which has been formed to substrate 71 using an epitaxile technique.

Figure 5:
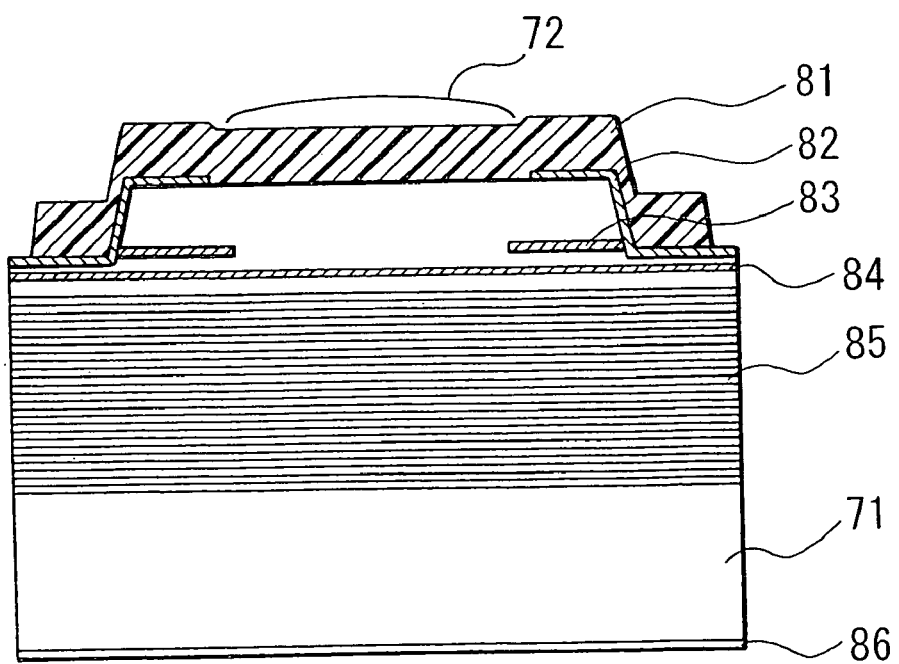
FIG. 5 is a cross-sectional diagram of the planar emission laser shown in FIG. 4.

FIG. 5 is a cross-sectional view of a planar emission laser. When an electron or hole carrier is injected from bottom substrate 86 or upper substrate 82, these carriers continue dispersing to reach active layer 84. A design in which the carrier injected from upper electrode 82 is squeezed by a current construction layer and collected in the active layer 84 directly below opening 72 is preferred. Electrons or holes reaching active layer 84 bond again, to emit light. This light passes through a resonator formed by lower semiconductor mirror 85 and upper semiconductor mirror 81. The cycling light is amplified when it passes through active layer 84 due to conductive emission, with light which has a large output shut inside the resonator. A portion of this light passes through upper mirror 81 and is emitted to the outside as laser light 73.

Figure 6:
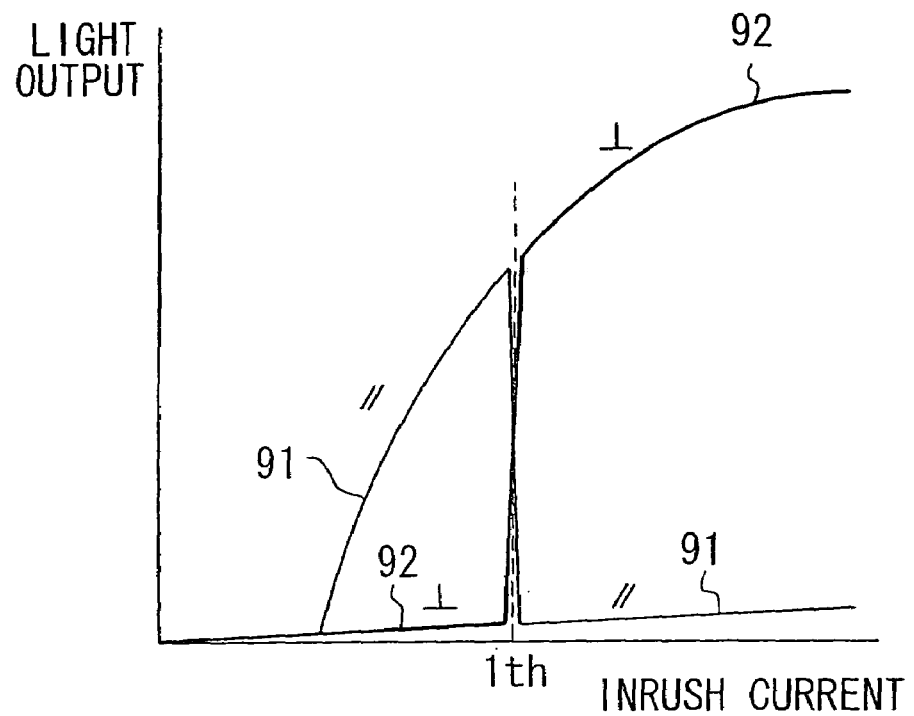
FIG. 6 is a characteristics diagram showing the relationship between the inrush current and the light output in the polarized light direction in the planar emission laser shown in FIG. 4.

A planar emission laser operates in this way. However, as may be understood from FIG. 4, the shape of resonator 74 can be freely designed using photolithography. Thus, it is possible to control the polarized light. For example, if resonator 74 is formed so as to have a circular shape in cross-section as shown in FIG. 4, then the degree of freedom for the polarization plane of laser light 73 is large because a specific direction is not possible. For this reason, the polarization plane can be switched by varying the inrush current quantity as shown in FIG. 6. FIG. 6 shows the dependence on the inrush current of polarized light component 91, in which the light output is in the parallel direction (where "parallel" is a direction selected for convenience), and polarized light component 92, in which the light output is in the perpendicular direction (i.e., perpendicular to the parallel direction). If the inrush current is less than Ith, then light which is linearly polarized in the parallel direction is mainly emitted. If the inrush current exceeds Ith, then the output is switched to light which is linearly polarized in the perpendicular direction. In other words, by modulating the inrush current around Ith, it is possible to modulate the polarization plane of the linearly polarized light. An example of modulating the inrush current is shown here. In addition, however, it is also possible to modulate the polarization plane using the impression of an electric or magnetic field, the application of strain, or the inrush of polarized light. The transmitter according to this embodiment can be realized using this type of planar emission laser as a linearly polarized light modulating light emitting element.

The above-described planar emission laser can be employed as a light source for light intensity modulation in transmitter 11a.

As a result, this polarized light communication device generates the following new effects by employing a planar emission laser as the light source for the transmitter. First, it is possible to decrease the power consumed by the transmitter. As compared to a terminal emission laser, which is the semiconductor laser which has been employed conventionally, the threshold current required for the planar emission laser to emit light is small. In other words, by supplying just a small amount of current, the planar emission laser emits light. Thus, it is possible to constrain the amount of power consumed.

Second, because the planar emission laser emits a conical or cylindrical beam having extremely strong directivity, it is possible to reduce wasted emitted light which does not reach the receiver, and to realize high speed or long distance communications at low power. When an LED is employed as the light source, the light emission angle is large, while the light emitting plane is big, making it difficult to collimate at the lens. In contrast, because the planar emission laser emits a conical or cylindrical beam, it is possible to concentrate the light intensity in one direction. While it is certainly the case that light is dispersed and diffused in a strongly dispersing medium like the body, receiving a narrowly squeezed parallel light is much more effective with respect to the proportion of light reaching the receiver, than is receiving a light which has been spreading from its start. As a result, this polarized light communication device employing the planar emission laser can carry out communications at low power, thus constraining the amount of power consumed.

There is a relationship between the transmission power, i.e., the light quantity or intensity, and the communications speed. Namely, the more the transmission power is increased, the faster communications can be carried out. Accordingly, this polarized light communication device is capable of even faster communications.

As a third effect, by using a planar emission laser, the SN ratio during communications can be improved. In contrast to an LED, in which the wavelength spreads over 100 nm, the light from a planar emission laser spreads over 1 nm or less. If a narrow band filter, such as an interference filter, is used on the receiving side, then the SN ratio can be improved.

D: Embodiment 3

Figure 7:
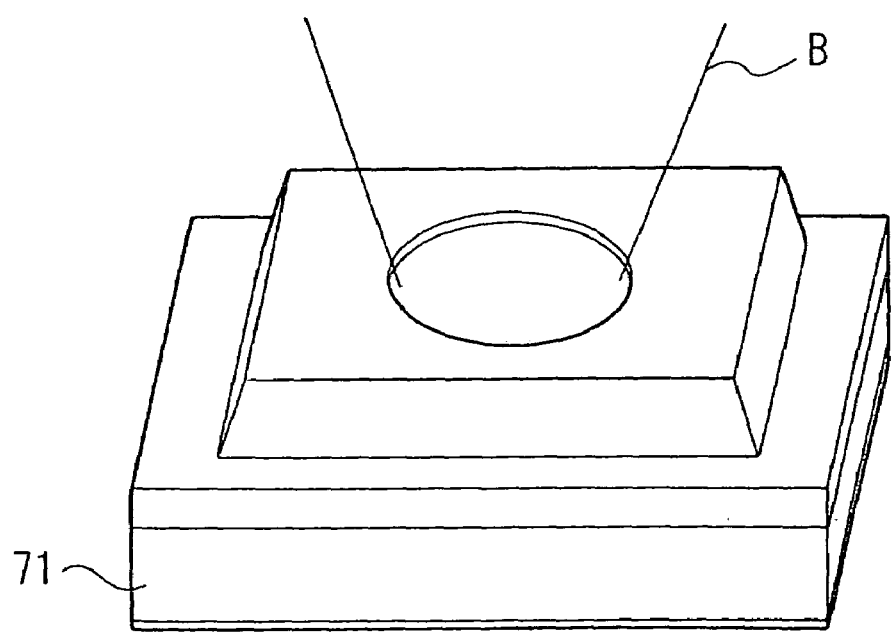
FIG. 7 is a perspective view showing an overview of a planar light emitting semiconductor laser in which the shape of the optical resonator is rectangular.
Figure 8:
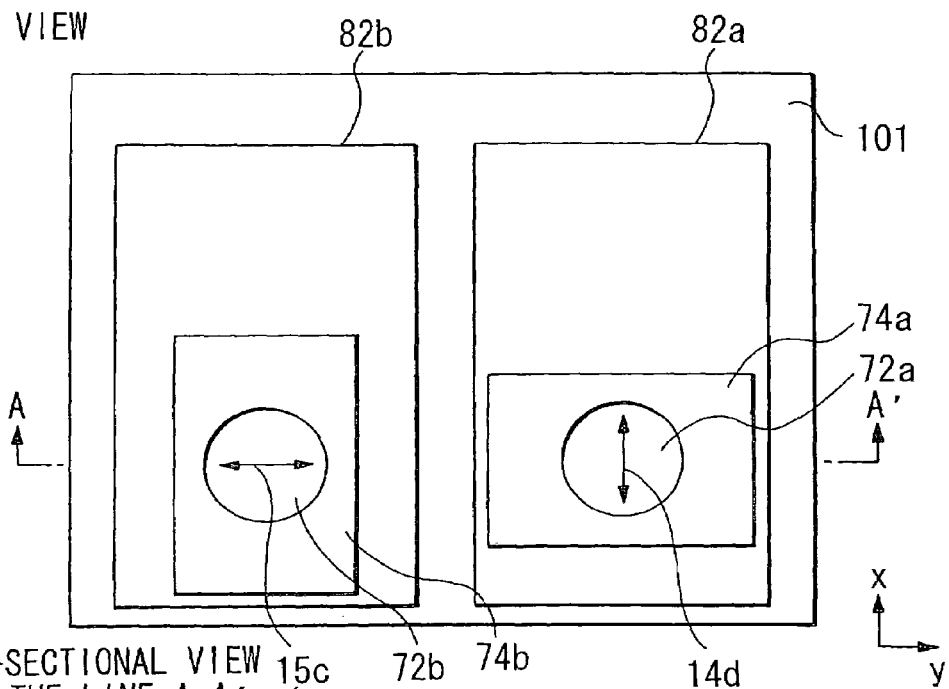
FIGS. 8A and 8B are planar and cross-sectional diagrams, respectively showing a perspective view of another planar emission laser used in the present invention's polarized light communication device.

Next, the case where the resonator is rectangular in shape as shown in FIG. 7 will be explained. In this case the direction of polarization of emitted light B is fixed to be in the direction of the short arm of the rectangle. For this reason, the polarized light modulating light emitting element can be realized by the following structure. In other words, as shown in FIGS. 8A and 8B, this polarized light modulating light emitting element is a planar emission laser having a plurality of holes in which two unit planar emission laser elements are provided onto a semiconductor substrate. These two planar emission laser elements emit laser light having different polarization planes. By associating one of the two planar emission laser elements with the transmission signal, and then selectively driving it, laser light in which the polarization plane is modulated is emitted.

Specifically, because the cross-section shown in FIG. 8A forms the rectangular-shaped resonators 74a, 74b, it is possible to control the polarization plane so as to be directed in a specific fixed direction. By forming rectangular resonators 74a, 74b, the polarization plane is fixed in a direction parallel to the short leg of the rectangle. In other words, rectangular resonator 74a in which the short leg is parallel to the x-axis and rectangular resonator 74b in which the short leg is parallel to the y-axis are formed to be adjacent to one another on a single substrate 71. As a result, it is possible to obtain a linearly polarized light 14d parallel to the x-axis and a linearly polarized light 15c parallel to the y-axis. Perpendicular linearly polarized light is not modulated and emitted from a single opening, but rather, linearly polarized light rays perpendicular to one another are emitted respectively from extremely close openings 72a,72b. The current may inrush from upper electrode 82a when linearly polarized light which is parallel to the x-axis is emitted, while the current may inrush from upper electrode 82b when linearly polarized light which is parallel to the y-axis is emitted.

Figure 9:
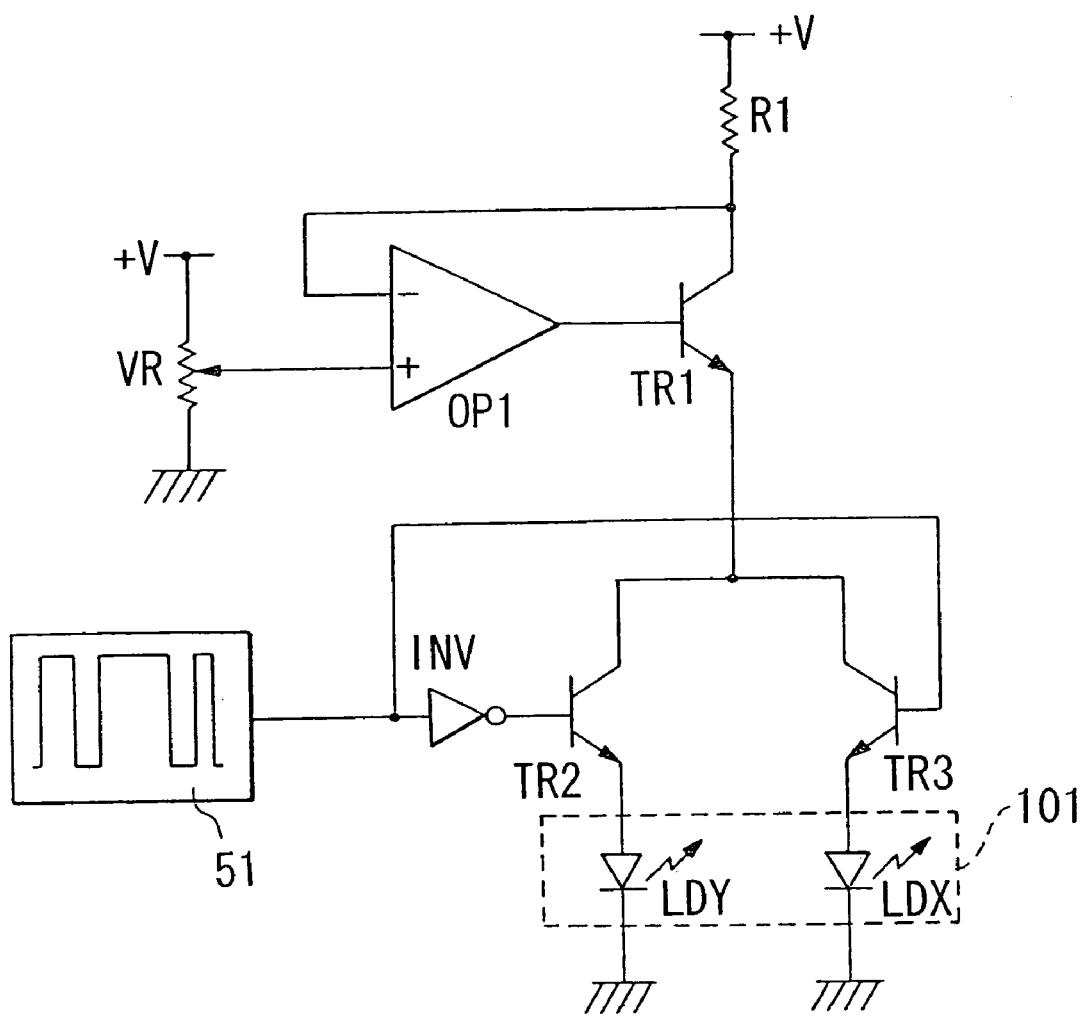
FIG. 9 is a circuit diagram showing the drive circuit of the planar emission laser shown in FIG. 8.

FIG. 9 is a circuit diagram showing the circuit for operating compound opening planar emission laser 10 having two planar emission laser elements shown in FIGS. 8A and 8B. In FIG. 9, OP amp OP1, transistor TR1, and resistor R1 form a fixed current source which supplies current corresponding to the voltage set by variable resistor VR from the emitter for transistor TR1. When the + terminal of OP amp OP1 is set in voltage V1 at variable resistance VR, a current Ie=(V−V1)/R1 is supplied from transistor TR1.

Transistors TR2 and TR3 employ a switching transistor to switch current Ie to planar emission laser element LDX or LDY. The base for transistor TR2, TR3 is driven according to transmission binary data 51 or to a reflected signal which has passed through inverter INV. In other words, TR2 and TR3 are complementarily switched on and off, and operate so that when one is ON, the other is OFF. Thus, at any given time, current le flows through just one of planar emission laser elements LDX or LDY. These planar emission elements LDX,LDY are themselves the compound opening planar emission laser 101 formed on a single substrate 71. When planar emission laser element LDX emits linearly polarized light parallel to the x-axis and planar emission laser element LDY emits linearly polarized light parallel to the y-axis, then, when transmission binary data 51 is "1" and linearly polarized light parallel to the x-axis is "0", linearly polarized light which is parallel to the y-axis is emitted from compound opening planar emission laser 101.

By employing a compound opening planar emission laser 101 of this type as a linearly polarized light modulating light emitting element, it is possible to realize transmitters 11, 21, and 11a by driving the circuit in FIG. 9. A constant current flows through transistor TR1 shown in FIG. This type of circuit structure, in which the current path can be changed by transistors TR2, TR3, is characterized in the ability to perform rapid modulation.

The embodiments shown in FIGS. 7 8A and 8B were employed to explain a transistor in which two planar emission laser elements are equipped to the same semiconductor substrate. Similarly, however, these embodiments may also be employed to realize a transmitter in which a plurality of planar emission lasers are equipped to the same semiconductor substrate.

The above-described polarized light communication devices employ polarized light as the transmission signal. Thus, it is possible to avoid interference between two transmission signals in the case of full duplex communication. This is shown by the fact that transmitter 11 and receiver 12, which are provided to the physiological function assisting means shown in FIG. 1, can be disposed extremely close to one another. In other words, a plurality of planar emission laser elements such as shown in FIGS. 8A and 8B and the planar emission laser drive circuit such as shown in FIG. 9 can be formed to the same semiconductor substrate, so that the outer shape of the polarized light communication device according to the present invention can be made extremely compact.

E: Embodiment 4

(1) Structure

The fourth embodiment employs an array-type planar emission laser (compound opening planar emission laser), in which a plurality of planar emission laser elements are formed to the same semiconductor substrate, for transmitters 11, 21, and 11a shown in FIGS. 1 and 2. The polarized light communication device according to this embodiment employs an arrangement in which a plurality of planar emission laser elements shown in FIGS. 4 and 5 are formed to the same semiconductor substrate for the light sources for transmitters 11, 21 and 11b.

Laser light having a modulated polarization plane is emitted by selecting several planar emission laser elements from among the plurality of planar emission laser elements, and then selectively driving these planar emission laser elements after associating them with a transmission signal.

On the other hand, when the planar emission lasers usually driven are no longer in the desired state (as in the case of a break-down, for example), then the other planar emission laser (reserve lasers) are driven. As a result, communication is continuously maintained.

(2) Operation

The operation of this polarized light communication device will now be explained with reference to FIG. 1. It is preferable that physiological function assisting means 1, which is embedded in the body, is capable of continuous use in a semi-permanent manner while remaining embedded in the body. This is also required of transmitter 11 and receiver 12, which are components of physiological function assisting means 1.

A plurality of the planar emission lasers shown in FIG. 4 and elsewhere can be formed on one semiconductor substrate chip, with the interval of spacing between each of these planar emission lasers made extremely small (40–50 micrometers, for example). A portion of this plurality of semiconductor lasers is designated as a reserve light source. When the output for the planar emission lasers employed in communication falls or is disrupted, communication can still continue without repair, since a switch can be made to the reserve planar emission lasers.

In addition, when an increase in the speed of communications is desired, a larger emitted light quantity is demanded of the transmitter. A plurality of planar emission lasers can therefore be modulated and driven simultaneously to increase the emitted light quantity and enable an increase in the communication speed.

Figure 11:
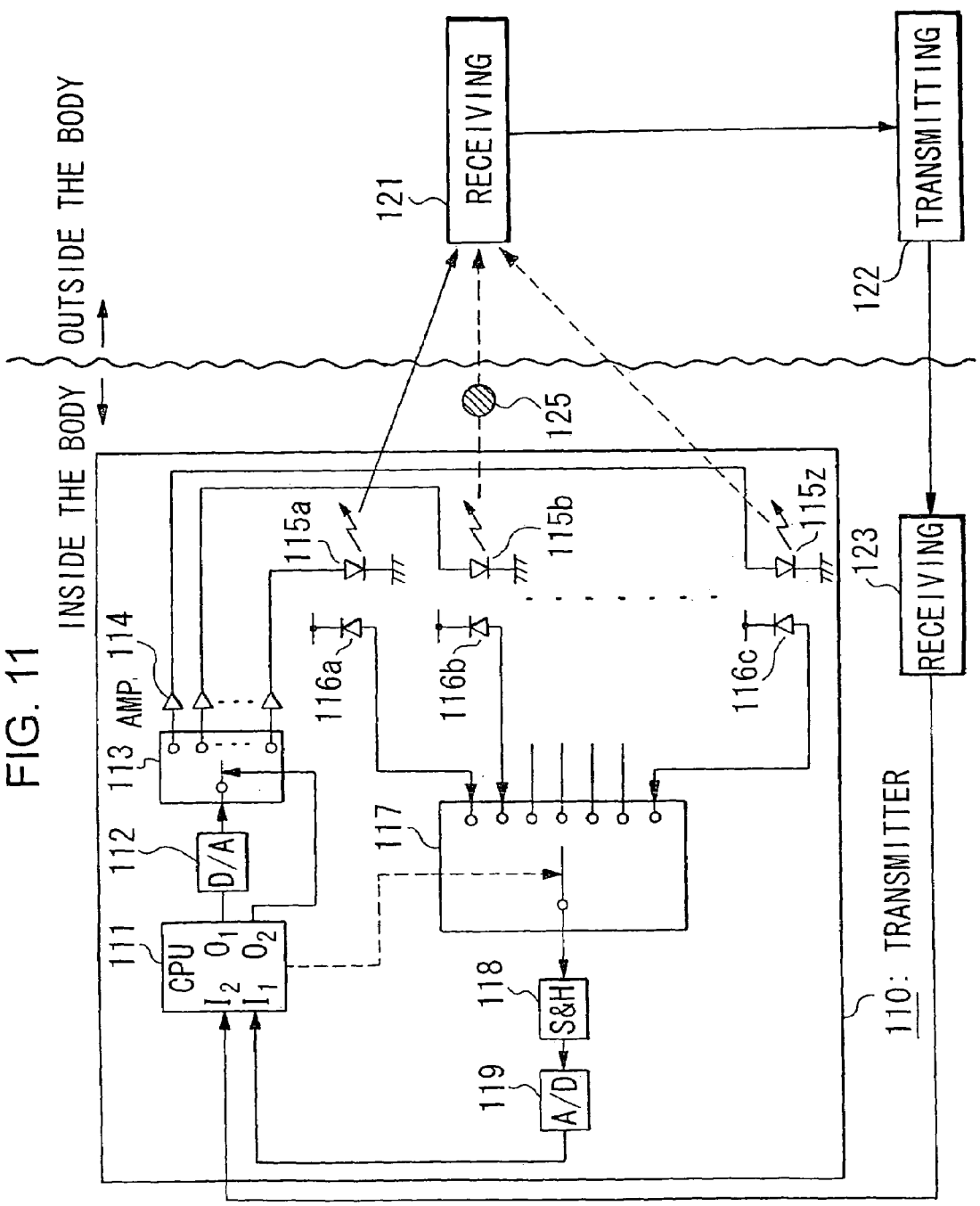
FIG. 11 is a circuit diagram showing a specific example of the transmitter used in the present invention's polarized light communication device.

FIG. 11 is a block diagram showing an example of the structure of transmitter 110 in the polarized light communication device according to this embodiment. A plurality of planar emission laser elements 115a, 115b, through 115z are driven based on output signals 01,02 from CPU 111. Output signal 01 is a signal for controlling the amount of current supplied. Output signal 02 is a signal for selecting the planar emission laser element to be driven. Output signal 01 is converted to an analog quantity by D/A converter 112. The output signal from D/A converter 112 is input at multiplexer 113, and output signal 02 is output to the planar light emitting element which is specified. The output signal from multiplexor 113 is amplified by amplifier 114, to become the drive current for the planar emission laser element.

Photo diodes 116a, 116b, through 162 are provided near each planar emission laser element 115a, 115b, through 115z, respectively These photo diodes detect the amount of light emitted by the planar emission lasers which are driven as the light sources in optical communications. This emitted light quantity is input to CPU 111 via multiplexor 117, sample and hold circuit 118, and A/D converter 119. An input to CPU 111 is the amplitude value of the received signal at receiver 121, which is outside the body and is the partner in the communications, via transmitter 122 and receiver 123.

CPU 111 determines whether or not there is an abnormality in the operation of the planar emission laser currently in use based on the value of output signal 01, the emitted light quantity from the planar emission laser elements currently in operation, and the amplitude value of the signal received from the communications partner. For example, when the quantity of emitted light or the amplitude of the signal received is smaller than the value of output signal 01, then CPU 111 makes a determination that a break-down has occurred in the planar emission laser. CPU 111 then changes output signal 02, stops the supply of power to the planar emission laser currently operating, and switches the planar emission laser element which will serve as the light source by supplying power to another planar emission laser element.

It is preferable if all of the electronic components which form the compositional elements of the above-described transmitter 110 are provided on the same semiconductor substrate. As a result, it is then possible to form an extremely compact transmitter 110.

Since it is possible to limit break-downs in transmitters 11 and 21 in this polarized light communication device, a device for communicating between the inside and the outside of the body can be provided which can be continuously used safely over a long period of time. In addition, the speed of communications can also be improved by providing a plurality of planar emission lasers for the light source.

(Modifications)

Figure 10:
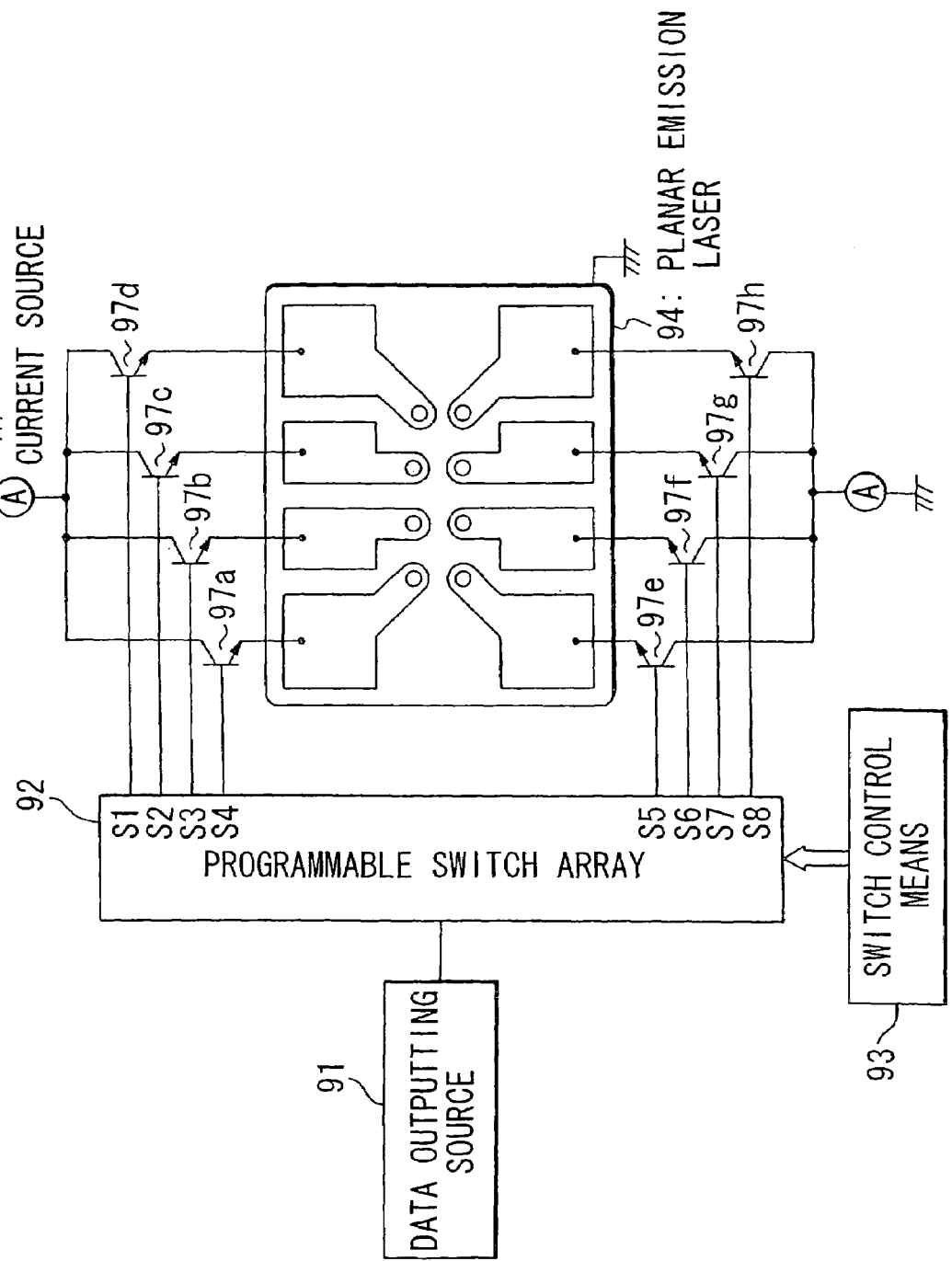
FIG. 10 is a circuit diagram showing another drive circuit for the planar emission laser used in the present invention's polarized light communication device.

FIG. 10 is a circuit diagram showing one example of the circuit for driving a compound opening planar emission laser having a plurality of planar emission laser elements. Data output source 91 outputs a signal which serves as a standard for the transmission signals sent from a transmitter 11 or the like. Switch control means 93 outputs a signal for selecting which output terminal from among output terminals S1~S8 in programmable switch array 92 will be placed in the active state. Programmable switch array 92 outputs the signal received from data output source 91 from the output terminal selected by switch control means 93. Planar emission laser 94 consists of a plurality of planar emission laser elements 94a~94h. Transistors 97a~97h are turned on and off according to the current output from programmable switch array output terminals S1~S8, thereby supplying current to respective planar emission laser elements 94a~94h.

As a result, it is possible to supply a drive current to only the planar emission laser element selected by switch control means 93, so that it is possible to optionally select the planar emission laser element which serves as the light source from among the plurality of planar emission laser elements. The operation of switch control means 93 can be controlled by a transmission signal from transmitter 21 which is located outside the body. Thus, it is possible from outside the body to optionally select the planar emission element which serves as the light source for the internal transmitter.

F: Other Embodiments

Embodiments in which the present invention's polarized light communication device is incorporated into a portable device will now be explained. However, the present invention is not limited to the embodiments which follow, but rather may be combined with a variety of everyday objects worn on the body.

Figure 12:
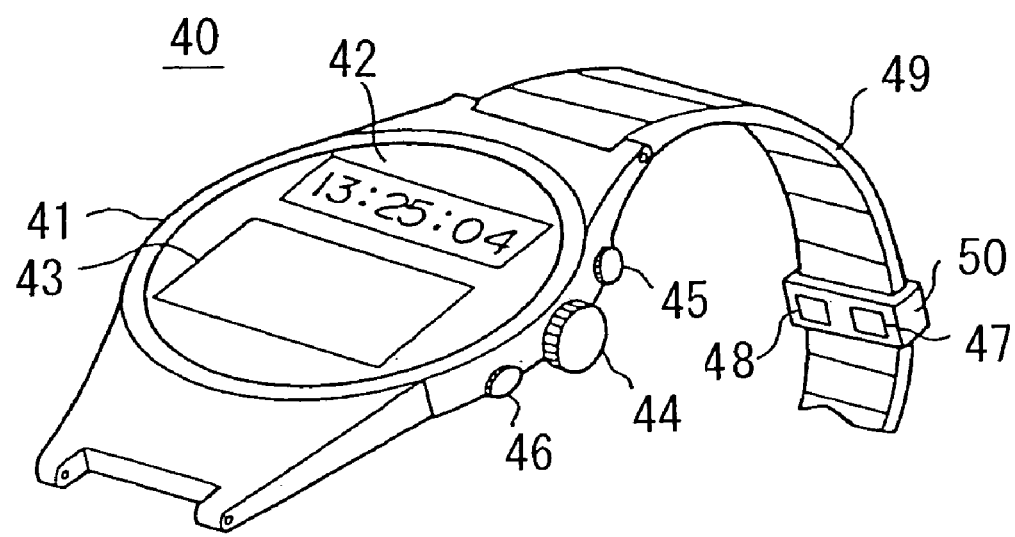
FIG. 12 is a perspective view showing the arrangement when the present invention's polarized light communication device is incorporated in a wristwatch.

FIG. 12 is a perspective view showing an embodiment in which the external control means for the present invention's polarized light communication device is incorporated into a wristwatch. In this figure, the numeral 40 indicates a wristwatch, 41 is the main body of the wristwatch, and 42~43 are displays for carrying out a variety of displays. Numerals 44~46 are buttons which are manipulated to change the contents of the display on displays 42~43, or the planar emission laser element which serves as the light source. Numerals 47 and 48 are a transmitter and receiver respectively, which communicate mutually with the physiological function assisting means (not shown) which is embedded in the arm of the user. Note that transmitter 47 and receiver 48 may also be provided on the back of main body 41 of the wristwatch.

Transmitter 47 and receiver 48 are attached to the back of attaching member 50. Attaching member 50 is attached in a freely sliding manner to watch band 49. Wristwatch 40 is attached to the wrist so that button 44 lies on a line through the center of the back of the hand. Receiver 48 and the transmitter for the physiological function assisting means located inside the body face each other, while transmitter 47 and the receiver for the physiological function assisting means located inside the body face each other.

The user can finely adjust the positional relationship between the transmitter and receiver for the internal physiological function assisting means, and transmitter 47 and receiver 48 located outside the body, by adjusting the position of attaching member 50 while observing the reception state at receiver 48 as it is displayed on display 43. The user can also carry out this fine adjustment by manipulating buttons 46, etc. to change the selection of the planar emission laser element which serves as the light source for the transmitter for the physiological function assisting means.

Figure 13:
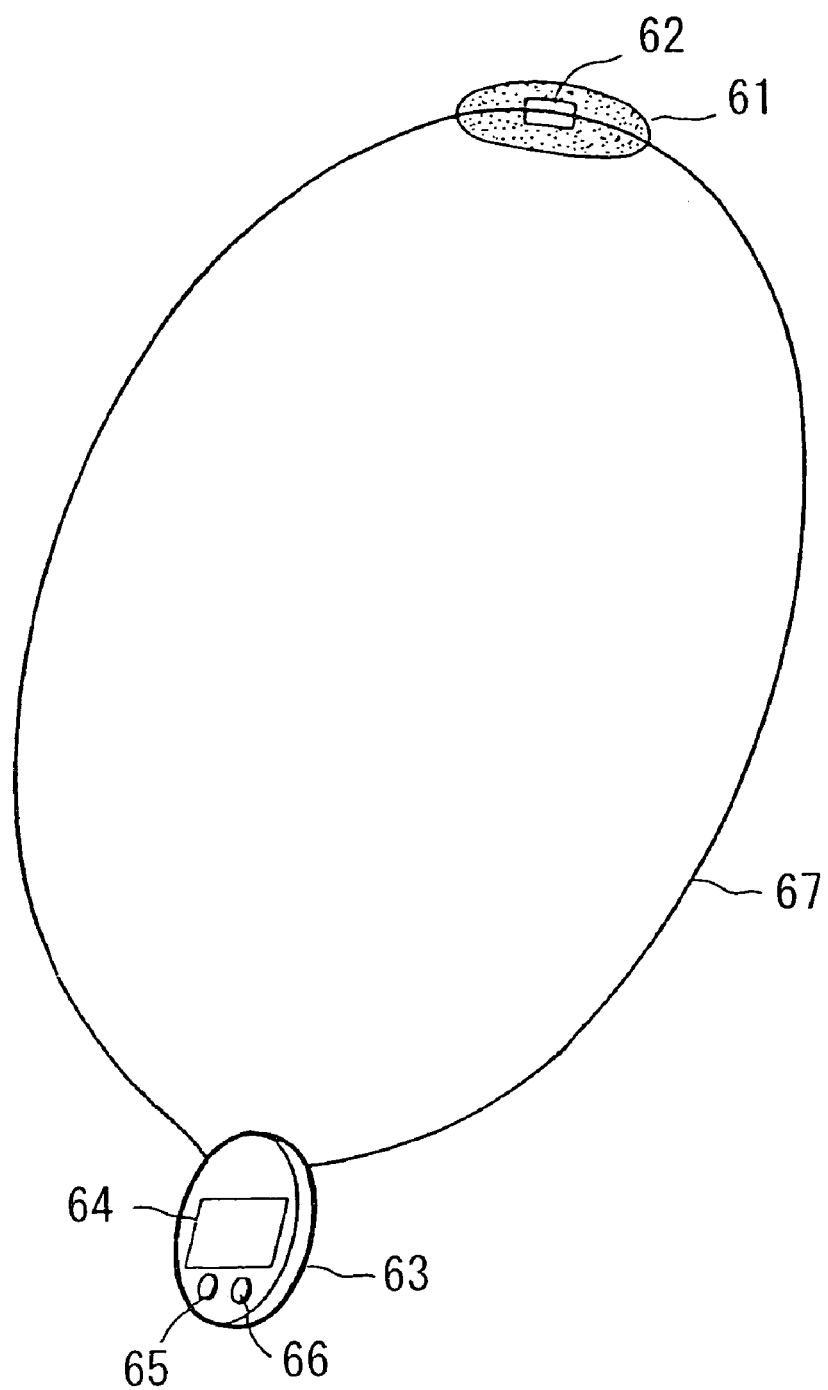
FIG. 13 is a perspective view showing the arrangement when the present invention's polarized light communication device is incorporated in a necklace.

FIG. 13 is a perspective view showing an embodiment in which the external control means for the present invention's polarized light communication device is incorporated in a necklace. In this figure, numeral 61 is a sensor pad, formed of a spongy shock-absorbent material, for example. Transmission/receiving device 62, consisting of a transmitter and receiver, is attached in the middle of sensor pad 61 so as to come in contact with the skin surface. As a result, when this necklace is worn around the neck, transmission/receiving device 62 comes in contact with the skin at the back of the neck, enabling mutual communication with a physiological function assisting means which is embedded in the neck.

The control function portion of this polarized light communication device is incorporated inside main body 63 which is hollow. This main body 63 is a broach-shaped case, and is provided on the front surface thereof with a graphic display and buttons, for example. Transmission/reception device 62 and main body 63 are attached respectively to a chain 67, and are electrically connected via a lead wire (not shown) embedded inside chain 67.

Figure 14:
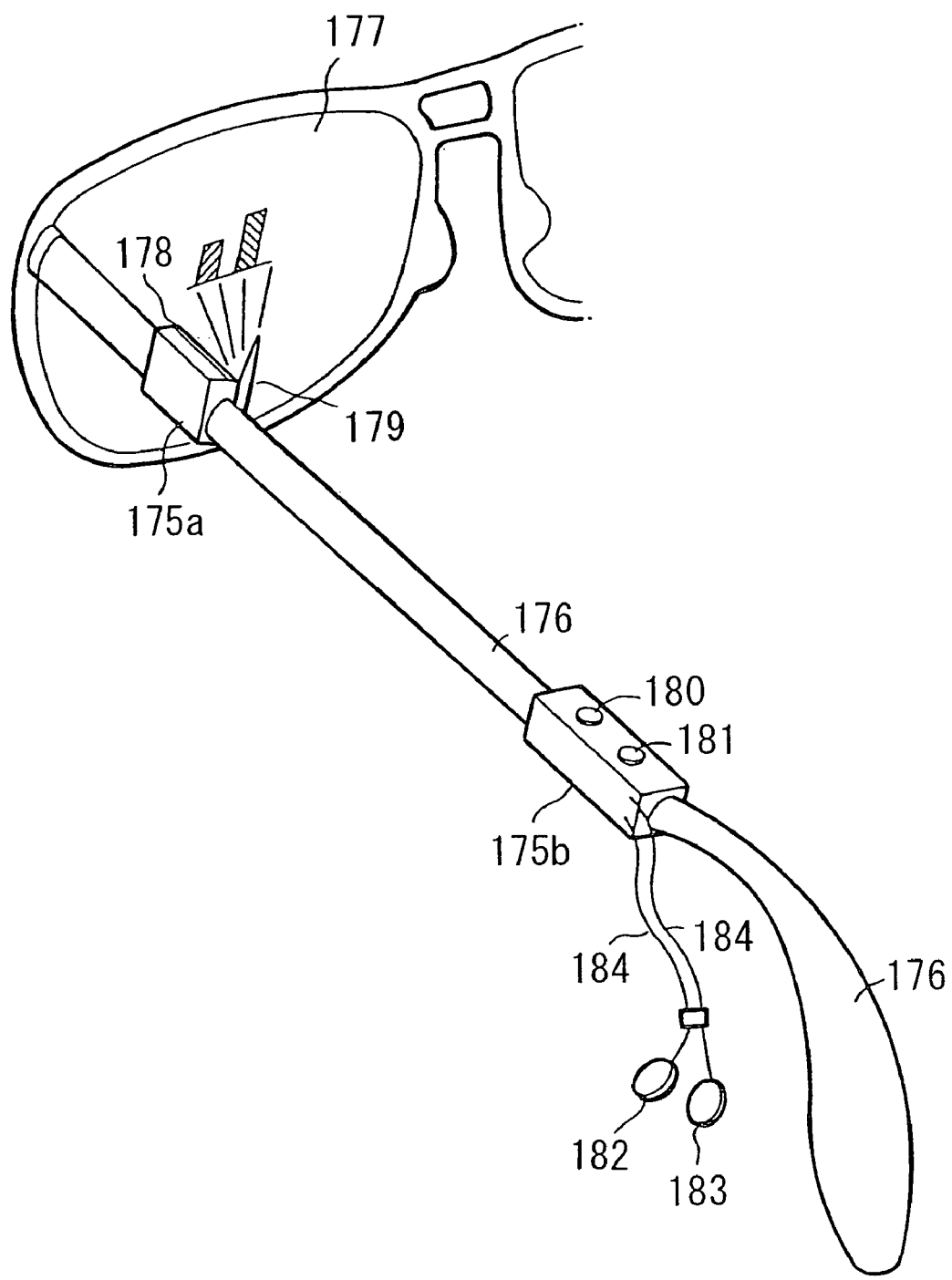
FIG. 14 is a perspective view showing the arrangement when the present invention's polarized light communication device is incorporated in a pair of eyeglasses.

FIG. 14 is a perspective view showing an embodiment in which the external control means for the present invention's polarized light communication device is incorporated into a pair of eyeglasses. Note that a display device for notifying the user is also incorporated together in this eyeglass arrangement.

As shown in the figure, the main body of the device is divided into main body 175*a* and main body 175*b*, which are attached to the respective stems 176 of the eyeglasses. These main bodies are electrically attached via a lead wire embedded inside stems 176.

Main body 175*a* houses a display control circuit. A liquid crystal panel 178 is provided across the entire lateral surface of the lens 177 side of main body 175*a*. A mirror 179 is fixed at a specific angle at one edge of this lateral surface. A drive circuit for liquid crystal panel 178 which includes a light source (not shown) and a circuit for creating display data are incorporated in main body 175*a*. The light emitted from this light source passes via liquid crystal panel 178, and is reflected at mirror 179 to fall on lens 177 of the eyeglasses. Further, the main portion of the device is incorporated in main body 175*b*, with a variety of buttons provided on the top surface thereof. The functions of these buttons 180,181 differ according to each device.

The transmitter and receiver for sending and receiving the laser light are housed in pads 182,183, with pads 182,183 fixed to the ear lobes of the user. These pads 182,183 are electrically connected by lead wires 184,184 which extend from main body 175*b*. By fastening pads 182,183 to the earlobes, the transmitter and receiver inside the pads come to face the transmitter and receiver for the internal control means which is embedded in the earlobe, thereby enabling mutual communication.

G: Embodiment 5

An explanation will now be made of an embodiment in which the pulse wave is detected using the above-described planar emission laser.

(1) Structure

Figure 15:
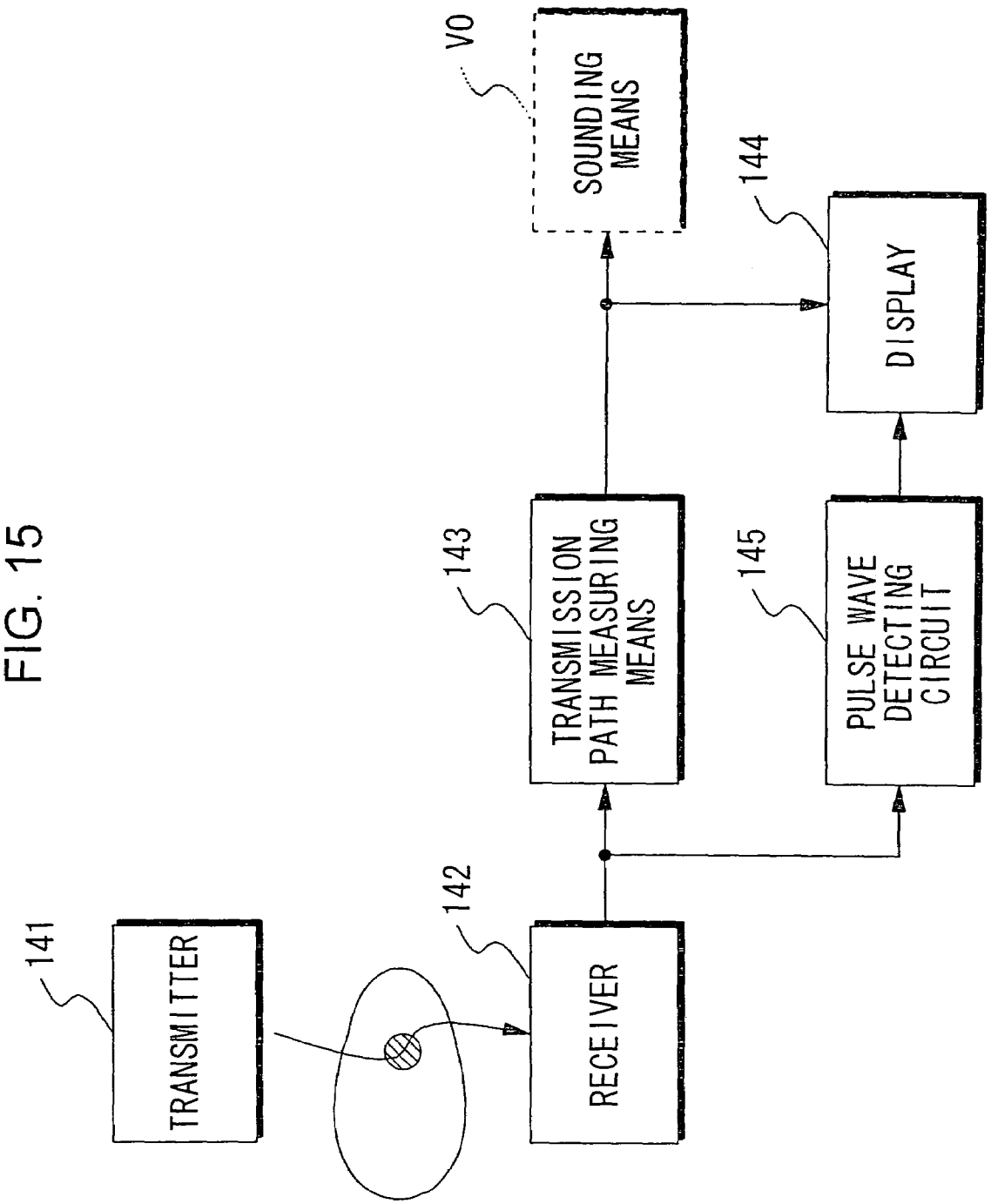
FIG. 15 is a block diagram showing the basic structure of the fifth embodiment of the present invention.

FIG. 15 is a functional block diagram showing the basic structure of the fifth embodiment of the present invention. In this figure, 141 is a transmitter for illuminating laser light, and employs as the light source a device which modulates the polarization plane of the laser light, and outputs the result. 142 is a receiver. Receiver 142 is provided with a light receiving element and polarized light filter for selectively receiving light which is in a specific polarization state. Receiver 142 outputs electrical signals corresponding to the polarization state (polarization angle and ellipticity) of the received light.

Modulation of the polarization plane will now be explained briefly. Polarized light contains linearly polarized light, as well as clockwise or counterclockwise circular and elliptical polarized light, for example. When modulating the polarization plane, the polarized light state is changed in response to a modulation signal. For example, when linearly polarized light is used, then perpendicular linearly polarized light is assigned a signal of "1" or "0", and modulation is carried out by switching the polarization plane. When a clockwise and counterclockwise circularly polarized light set is used, then signals "1" and "0" are assigned, and modulation is carried out by switching the polarization direction. At the receiver, demodulation is carried out by using a polarized light filter to discern which direction the light is polarized in.

The typical semiconductor laser can only emit linearly polarized light. If, however, a ¼ wavelength plate is used, then linearly polarized light can be converted to circularly polarized light. In other words, if a ¼ wavelength plate is disposed in a position inclined at a 45° angle with respect to the light axis of the linearly polarized light, then, by switching the direction of the linearly polarized light, it is possible to generate light which is circularly polarized in the clockwise or counterclockwise direction. In a vertical resonator planar emission semiconductor laser, the polarization plane can be modulated without employing a ¼ wavelength plate. This planar emission laser will be explained below.

When receiving a signal, the process is the opposite of that when transmitting a signal. Namely, a ¼ wavelength plate is used to convert circularly polarized light to linearly polarized light with two axes. Demodulation can then be carried out by detecting the size of the polarized light components of each axis. As an example, the x and y axes are set at a position which is inclined ±45° from the optical axis of a ¼ wavelength plate, and a polarized light beam splitter may be placed so as to reflect polarized light components which are parallel to the x-axis and to transmit polarized light components which are parallel to the y-axis. A light detector may then be provided for detecting the polarized light components which are separated by the beam splitter. If the output from the light detector is input to a differential amplifier, then it is possible to amplify only the component in which the polarized light has been modulated, thereby removing same-phase components influenced by the disturbance of non-polarized light. It is therefore possible to obtain a signal having a good SN ratio as a result.

Numeral 143 in FIG. 15 indicates a transmission path measuring means, for detecting the strength (amplitude) of the signal received by receiver 142, and outputting the detected result to display (notifying means) 144. Display 144, which is formed of a liquid crystal dot display, performs a variety of displays, as well as displaying the results of detection by transmission path measuring means 143. In this embodiment, display 144 displays the measured results from transmission path measuring means 143 as a numerical value. In addition, however, a variety of other graphical displays are also possible, including a circular graph or a bar graph in which the length of the bars varies. In summary, any form of display is acceptable, provided that it can notify the operator of the results detected by transmission path measuring means 143.

Symbol 145 in FIG. 15 is a pulse wave detecting circuit which extracts the pulse wave component from the signal output from receiver 142, and outputs this result as the pulse wave signal. By extracting the pulse wave via a specific filter circuit, pulse wave detecting circuit 145 removes noise components, thus improving the S/N ratio. The pulse wave signal output by pulse wave detecting circuit 145 is supplied to display 144, where the pulse wave is displayed. Note that in the case where the spectrum of the pulse wave signal is calculated by performing a fast Fourier transform at pulse wave detecting circuit 145, then this spectrum may also be displayed on display 144.

Figure 16:
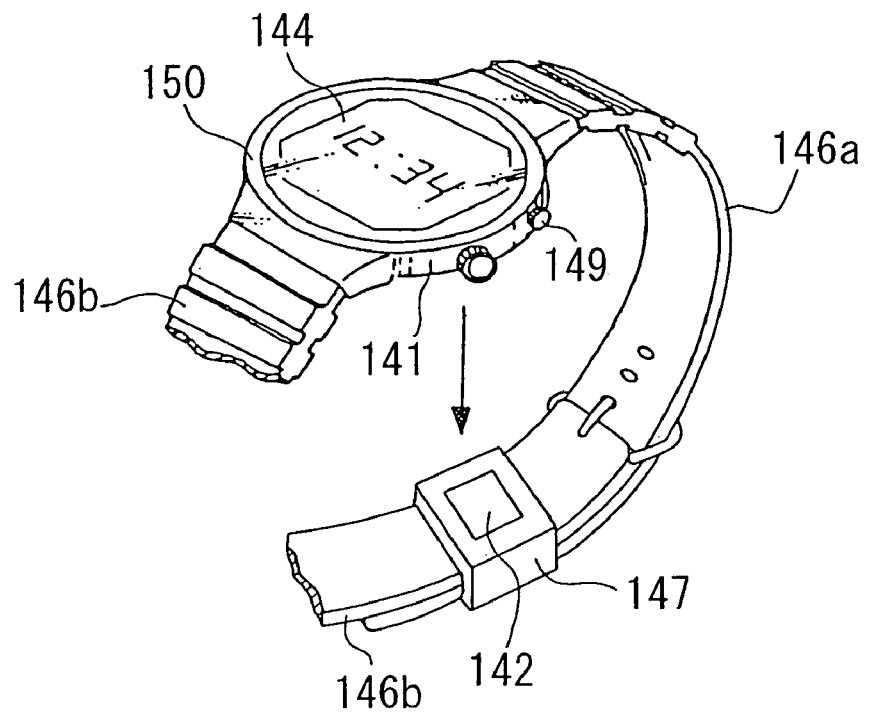
FIG. 16 is a perspective view showing the outer appearance of the fifth embodiment.

FIG. 16 is a perspective view showing the outer appearance of this embodiment. As shown in this figure, this embodiment is in the form of a wristwatch. Numeral 150 in FIG. 16 is the main body, which houses transmitter 141, transmission path measuring means 143, display 144 and pulse wave detecting circuit 145. In addition, a watch IC, not shown in the figure, is also provided in main body 150. As shown in FIG. 16, display 144 displays time information output by the watch IC. The numeral 149 is an operational button for carrying out a variety of operations, such as, for example, switching between a measuring mode, in which the pulse wave is measured, and a clock mode, in which the time is displayed.

Figure 17:
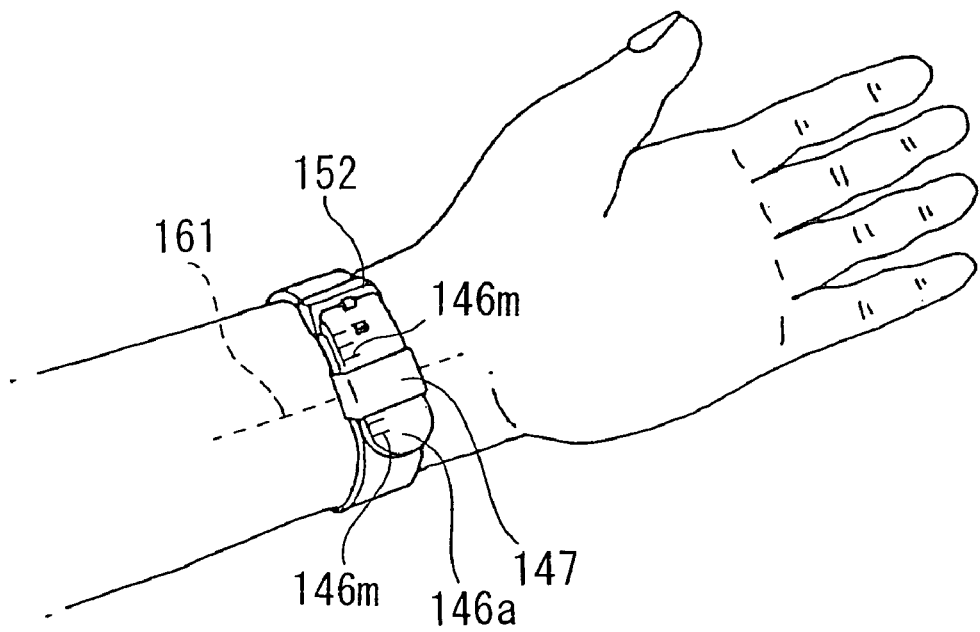
FIG. 17 is a perspective view showing the state of attachment in the fifth embodiment.

The emitting surface of transmitter 141 is exposed on the back surface of main body 150, and emits laser light in the direction indicated by the arrow in the figure. A pair of bands 146a,146b are attached to main body 150. The bands are attached by wrapping around the arm as shown in FIG. 17 and then being held in place by a specific fastening member 152. The numeral 147 indicates a cylindrical sliding member which is rectangular in cross-section and which is capable of freely moving along bands 146a,146b. Receiver 142 is provided inside this sliding member 147. Receiver 142 is provided so that its receiving surface faces the emitting surface of transmitter 141, and is designed to receive the laser light emitted from transmitter 141. A cable, not shown in the figures, is provided between receiver 142 and main body 150. As a result of this cable, reception signals are sent to transmission path measuring means 143 and pulse wave detecting circuit 145.

Figure 18:
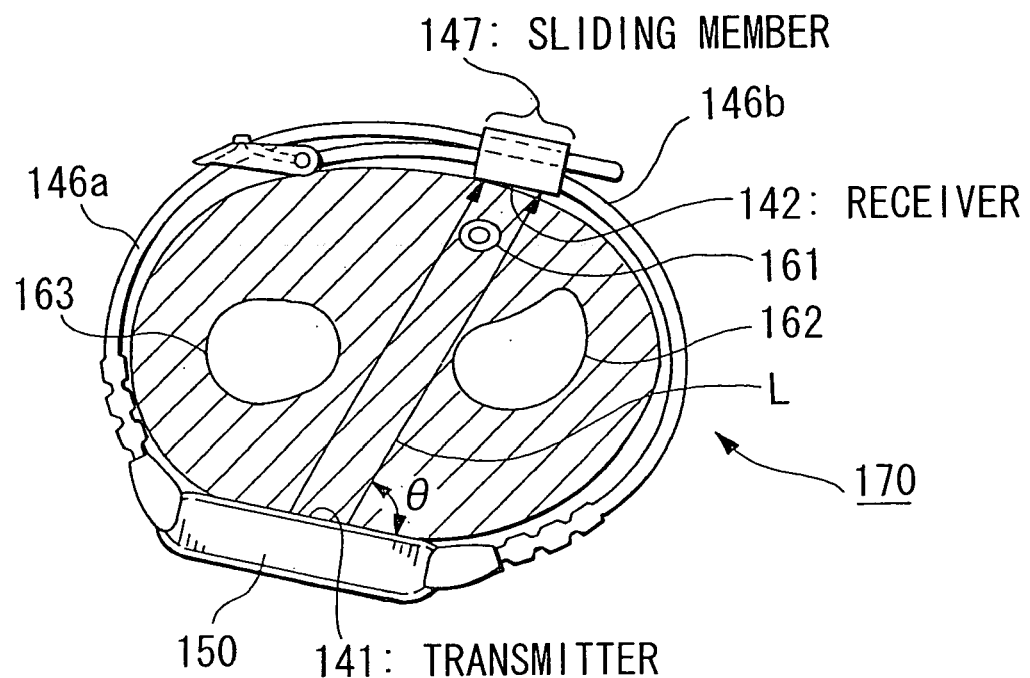
FIG. 18 is a cross-sectional diagram of the state of attachment in the fifth embodiment.

FIG. 18 is a cross-sectional diagram of an arrangement in which this embodiment is attached to the left arm. As shown in this figure, laser light emitted from transmitter 141 reaches receiver 142 via radius artery vessel 161. In other words, radial artery vessel 161 is positioned on transmission path L for the laser light which travels from transmitter 141 to receiver 142. This positional relationship is the most suitable for detecting the pulse wave.

When viewing the arm in cross-section, radial artery blood vessel 161 is positioned to the side of radial bone 162. Transmission path L must be set at a position which avoids the radial bone 162. Taking into consideration the positional relationship described above, the inclination of transmission path L in this embodiment is set to be in the range of 60°≦θ≦85°, when the bottom surface of main body 150 is taken as the base. By providing this type of inclination, transmission path L is set at a position which avoids the radial bone 162 and the ulna 163 when the device is worn in the typical manner. In summary, the position of transmitter 141 and receiver 142, and the direction of emission of the laser light (wave), are set acceptably so that transmission path L avoids the radial bone 162 and the ulna 163.

In addition, this embodiment is designed so that transmission path L can be adjusted to even more accurately pass through the center of the radial artery 161.

(2) Operation

The operation of this embodiment will now be explained. Bands 146a,146b are wrapped around the arm and held in place by fastening member 152. The device is then set in the measuring mode by manipulating operator buttons 149. As a result, laser light is emitted from transmitter 141, and is received by receiver 142.

The blood flowing through the blood vessels has absorption characteristics with respect to the absorption of light. The quantity of laser light received by receiver 142 is damped by the blood flowing through radial artery vessel 161. This damping is due to absorption of a portion of the laser light by the hemoglobin in the blood. The amount of damping is a function of the blood capacity at the area of the blood vessel through which the laser light passes. In other words, the quantity of damping is associated with the pulse wave of the blood which is flowing through radial artery vessel 161. Pulse wave detecting circuit 145 detects the pulse wave from the signal output from receiver 142, and outputs this result on display 144. As a result, the operator is able to observe his own pulse wave displayed on display 144.

As the same time, the amplitude value of the received signal is detected at transmission path measuring means 143, with this value then displayed on display 144. Adjustments can be performed by the operator by sliding sliding member 147 while observing the display on display 144, so that the amplitude becomes a maximum value. As a result, transmission path L is set at a position where it passes through the center of artery vessel 161. Thus, the S/N value of the pulse wave received at receiver 142 is maximized, providing an excellent pulse wave measurement.

In this embodiment, light emitted by transmitter 141 passing through the cross-section of radial vessel 161 is received at receiver 142. As a result, the proportion of natural or florescent light received inside or outside the body is smaller as compared to an arrangement in which light reflected by the radial artery 161 is employed as the pulse wave detecting signal. Accordingly, this enables a more accurate and stable pulse wave detection.

This is because light which is reflected inside the body does not have the characteristics of emitted light (i.e., wavelength, phase, degree of polarization), so that it is difficult to distinguish this reflected light from the external natural or illuminated light. However, since light passing through the body does have the characteristics of emitted light, it is easily distinguished from other light.

This embodiment employs polarized laser light. As a result, the effect of disturbance light is extremely reduced. This point will now be explained below.

Figure 19:
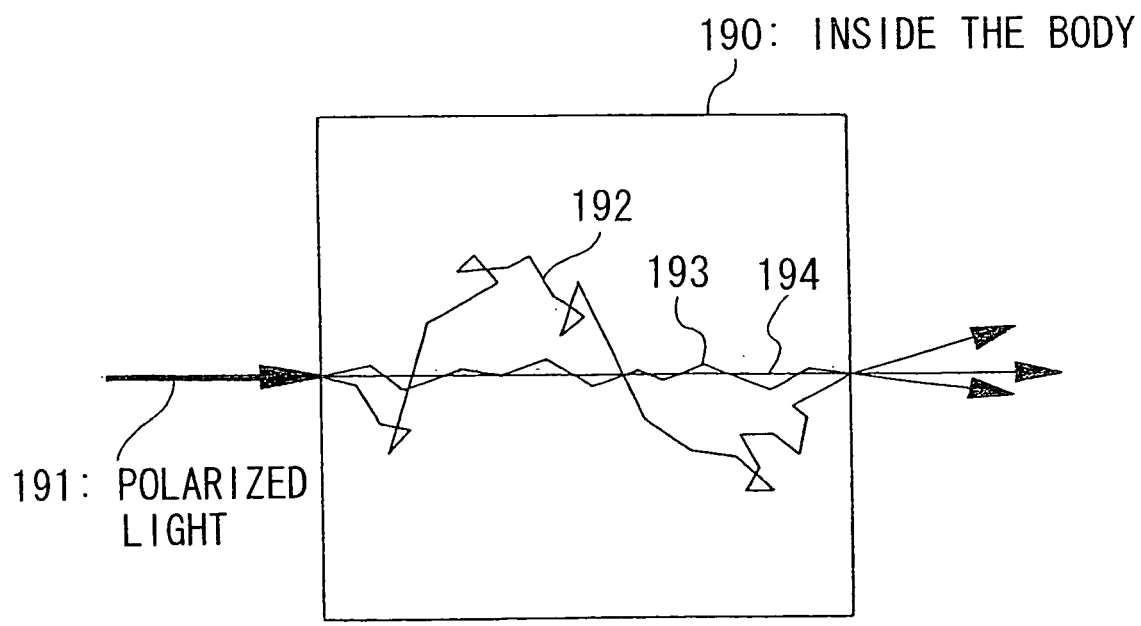
FIG. 19 is an explanatory figure for explaining the state of the polarized laser light progressing inside the body.

The polarized laser light emitted by transmitter 141 reaches receiver 142 after passing through radial artery 161. Receiver 142 receives only light of a specific polarization state. As shown in FIG. 19, of the polarized light 191 emitted by transmitter 141, some becomes dispersing light component 192 which has undergone strong multiple dispersion in the subject's arm (hereinafter, internal body 190) and has spread in random directions inside the body. This dispersing light component 192 cannot maintain its polarization state at the time of emission, and therefore becomes non-polarized. Conversely, the polarized light emitted by transmitting means 141 includes paraxial forward multiply scattering light component 193 which is propagating in the forward direction while maintaining a relatively small dispersing angle, and a forward multiply scattering directly advancing light component 194, which is directly advancing over an extremely short distance (time) as it gradually disperses in the forward direction. Paraxial forward multiply scattering light component 193 and forward multiply scattering directly advancing light component 194 maintain their polarization states at the time of emission.

This paraxial forward multiply scattering light component 193 and forward multiply scattering directly advancing light component 194 advance almost directly, to reach receiver 142 after passing through radius artery vessel 161. A portion of dispersed light component 192, which was dispersed within the limits of the body, reaches receiver 142, however, since non-polarized light is blocked by the filter for receiver 142, it does not become a detection signal. Natural light and various illuminated light from outside the body reaches receiver 142. However, this non-polarized light is also blocked by the filter for receiver 142, so that it does not become a detection signal.

In this embodiment, scattered light diffused over a broad range within the body and light entering the body from the outside can be discerned from the detection signal. As a result, it is possible to carry out a stable and accurate detection of the pulse wave.

G-1: Modification of Embodiment 5

(1) Example of Laser

The vertical resonator planar emission semiconductor laser explained above with reference to FIGS. 4 through 6 is employed as an optimal light source for transmitter 141 in the above-described embodiment. However, a planar emission laser may also be used as the light source for the transmitter, with the same effects obtained as in the preceding embodiment.

(2) Example of Notifying Means

As explained above, this embodiment was designed to use a display to notify the user of the positional relationship between transmission path L and radial artery 161. However, a design is also acceptable in which a sound is used in place of the display. Namely, as shown by the dashed line in FIG. 15, a sounding means VO may be provided which emits a sounds based on the output signal from transmission path measuring means 143. In addition, the device may be designed to notify the user of the positional relationship between the transmission path L and the arterial vessel by changing such sound characteristics as the tone, pitch, or volume in response to the amplitude of the received signal, for example. The sounding interval, for example the interval at which an electronic beep is sounded, may also be varied as a means of notification to the user.

(3) Determination of Position of Transmission Path L

The positional relationship between the transmission path L and the arterial vessel was determined in this embodiment based on the amplitude of the received signal. However, the determination may also be made by using other characteristics of the wave, such as frequency or phase, instead.

(4) Example Method for Determining Position of Receiver 142

As explained above, the user can set the position of transmission path L while observing the display on display 144. However, it is optimal if the user tries to position the transmission path L to pass as nearly as possible through radial artery 161 when initially positioning the device on the arm. Therefore, to provide some initial guide, a mark may be made on band 146a. In other words, as shown in FIG. 17, a scale 146m, 146m may be made at fixed intervals on band 146a, so that the user will come to remember where sliding member 147 is on the scale when transmission path L is at a good position. Immediately after attaching bands 146a, 146b on the arm, the position of sliding member 147 is adjusted to that position on the scale. In this way, the amount of adjustment required for sliding member 147 after shifting to the measuring mode is reduced. Thus, measurements can be carried out quickly.

H: Embodiment 6

(1) Structure

Figure 20:
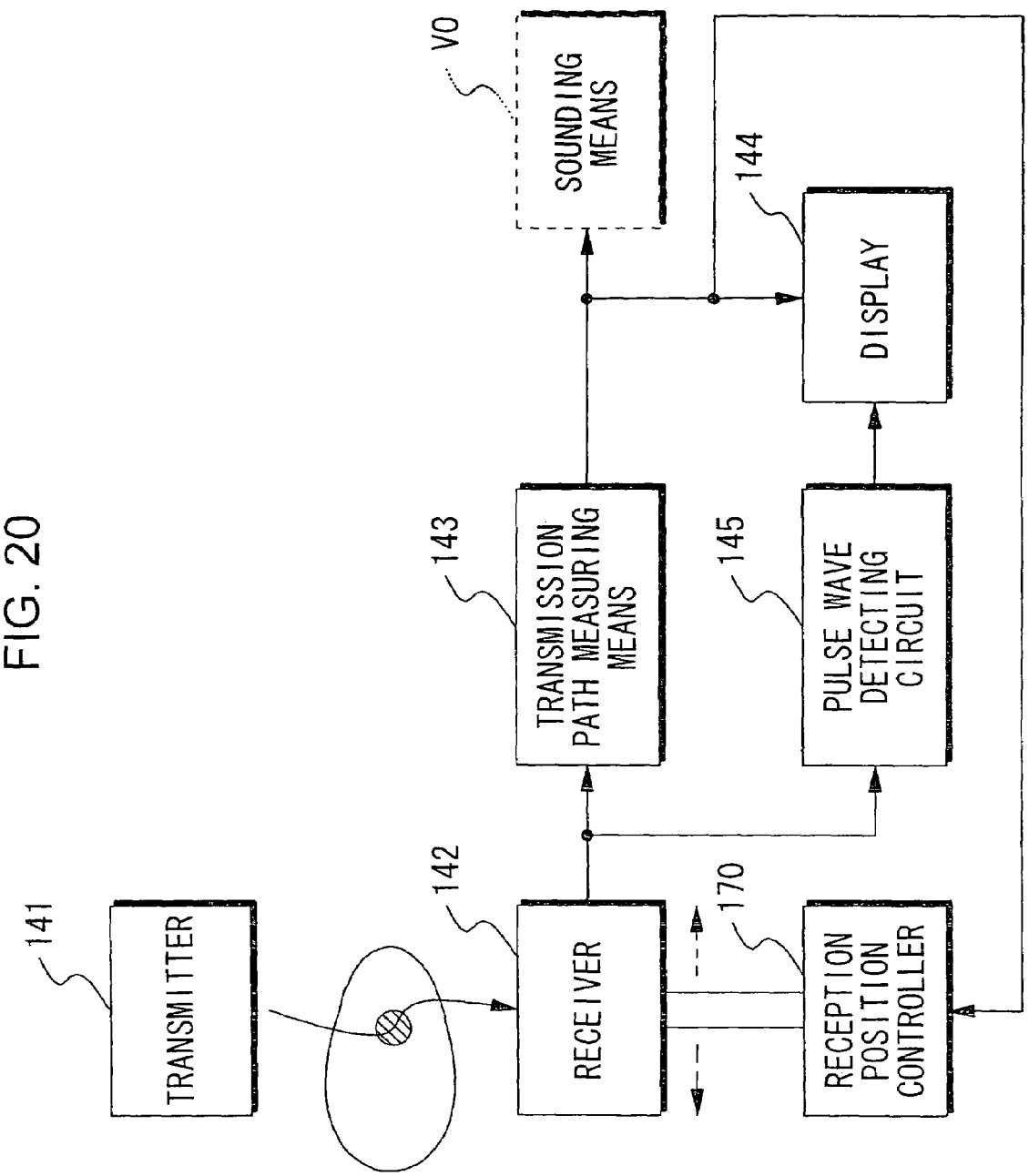
FIG. 20 is a block diagram showing the electrical structure of the sixth embodiment of the present invention.
Figure 21:
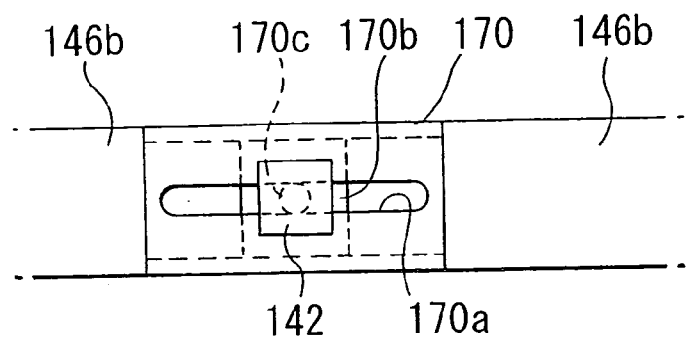
FIG. 21 is a planar view showing the outer appearance of reception position controller 10 employed in the sixth embodiment.
Figure 22:
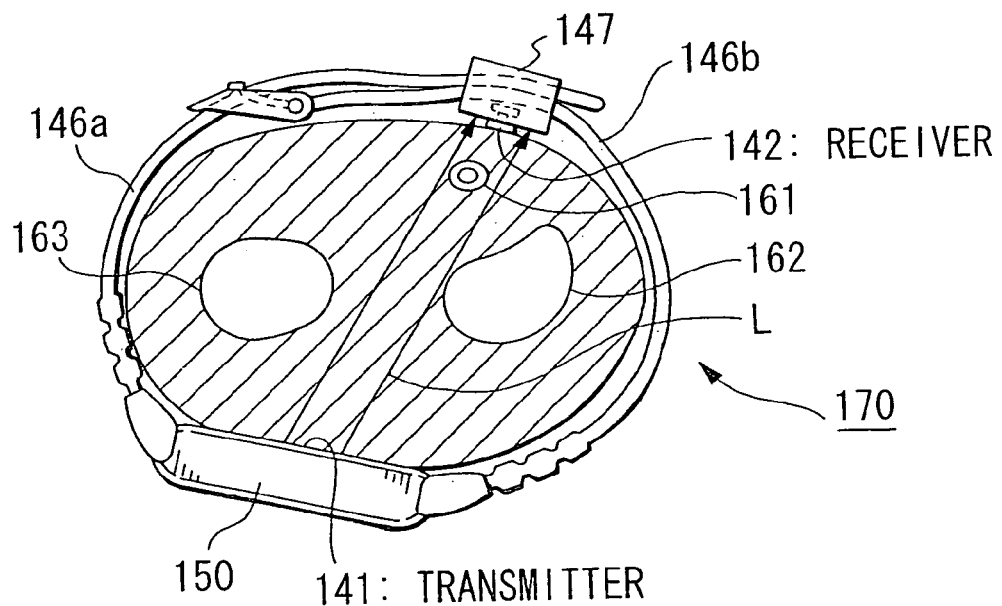
FIG. 22 is a cross-sectional diagram of the state of attachment of the sixth embodiment.

FIG. 20 is a block diagram showing the structure of the sixth embodiment. A reception position controller 170 is employed in this embodiment in place of sliding member 147 used in the design of the fifth embodiment. Reception position controller 170 drives receiver 142 about the circumference of the arm (i.e., in a direction which is perpendicular with respect to the radial artery), controlling the position of receiver 142 so that the amplitude value of the received signal output by transmission path measuring means 143 is maximized. FIG. 21 is a planar view (from the skin side) showing the outer appearance of reception position controller 170. As shown in the figure, band 146b passes through reception position controller 170. The inside of reception position controller 170 is designed as a linear motor, with 170b in the figure indicating the slider therefor. Slider 170b is provided with a projecting member 170c which projects out toward the skin. A receiver 142 is attached to projecting member 170c. Projecting member 170c can move freely along groove 170a at roughly 1 cm strokes in the direction from left to right in the figure. FIG. 22 is an explanatory figure showing an overview of the positional relationships between each of the elements when this embodiment is attached to the arm. As shown in the figure, receiver 142 comes in contact with the surface skin of the arm.

(2) Operation

When the device is set to the measuring mode in the preceding design, then transmission path measuring means 143 outputs the amplitude value of the received signal. Reception position controller 170 moves receiver 142 to the right by one pitch, and determines whether or not the amplitude of the received signal has increased. If the signal has increased, then reception position controller 170 moves receiver 142 to the right by one pitch again, and determines whether or not the signal has increased. Reception position controller 170 continues moving receiver 142 to the right by one pitch, until the amplitude value decreases, at which time reception position controller 170 moves receiver 142 back one pitch to the left and concludes movement of receiver 142. In the case where the amplitude decreases the first time reception position controller 170 moves receiver 142 to the right by one pitch, the direction of movement is immediately switched to the left, and the operation as described above is carried out.

As a result of the preceding operation, receiver 142 is controlled so that it is located at the position where the reception amplitude is maximal. In other words, transmission path L is set to be at a position where it passes through the arterial vessel. This embodiment differs from a device employing a pressure sensor (U.S. patent application No. 4,951,679, for example) in this case. Namely, because receiver 142 is not pressed against the skin, the force with which receiver 142 is moved along the surface skin of the arm is limited to a small value. Accordingly, sufficient servo-actuated control is possible using the torque of a typical linear motor. Further, given the relationship between the width of transmission path L and the diameter of the arterial vessel, the optimal position for transmission path L can be found by moving receiver 142 about 1 cm.

Figure 23:
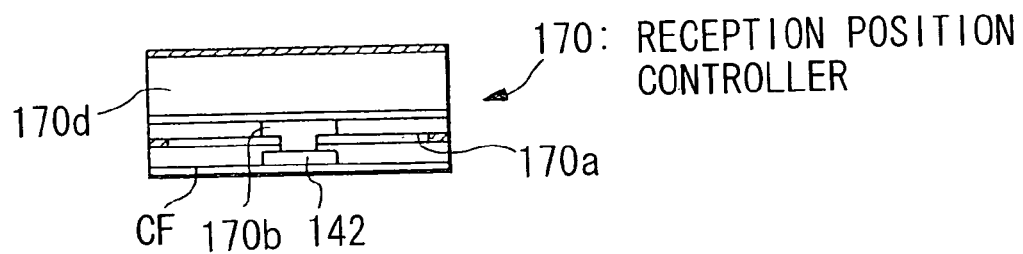
FIG. 23 is a cross-sectional diagram showing another structural example of reception position controller 10.

H-1: Modification of Sixth Embodiment (1) If a film CF, which transmits laser light, is attached to the boundary surface between reception position driver 170 and the skin as shown in FIG. 23, the resistance when sliding receiver 142 can be reduced. Thus, it becomes even easier to move receiver 142.

(2) The display of the amplitude on display 144 may be omitted in the second embodiment. The device automatically locates transmission path L at the optimal position using a servo-actuated mechanism, so that the user need not monitor the amplitude values. However, if amplitude values are shown on display 144, then the user is made aware of the operational status of the servo-actuated mechanism. Thus, if there is a malfunction in the mechanism, the user is still able to optimize the position of receiver 142 manually.

Figure 24:
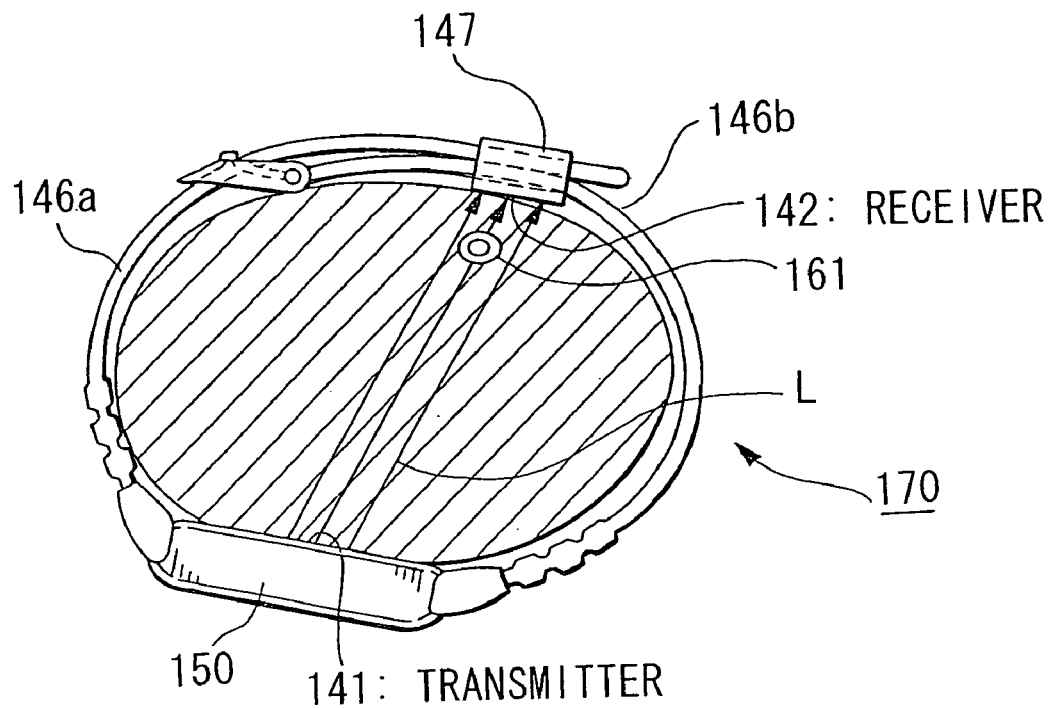
FIG. 24 is a cross-sectional diagram showing the structure of a modification of the sixth embodiment.

(3) In this embodiment, the position of receiver 142 was mechanically moved. In place of this arrangement, however, a design is also acceptable as shown in FIG. 24, in which a plurality of transmitters 141 are provided along the circumferential direction of the arm. These transmitters 141 are selectively operated so as to be scanned in sequence, and the transmitter 141 at which a maximum amplitude for the received signal is detected is selected.

(4) The position of receiver 142 was shifted in the preceding embodiments and modifications. However, it is also acceptable to move transmitter 141 (or to provide a plurality of transmitters 141, and selectively operate these). In summary, a design is acceptable provided that the relative positioning of transmitter 141 and receiver 142 changes, so that the position of transmission path L moves as a result.

I: Embodiment 7

(1) Structure, Action

The seventh embodiment of the present invention will now be explained. The electrical structure of this seventh embodiment is the same as that of the sixth embodiment described above, but the mechanical structure differs.

Figure 25:
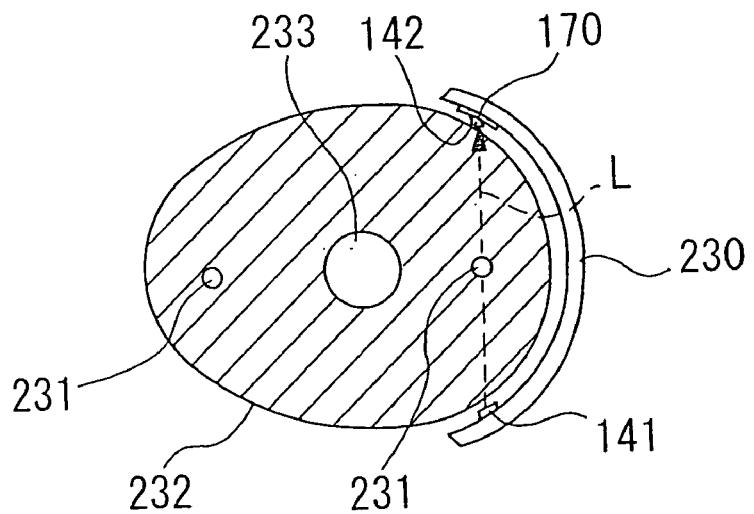
FIG. 25 is a planar view showing the overall structure of the seventh embodiment.

FIG. 25 is a planar view showing the structure of the seventh embodiment. In this figure, 230 is an arch-shaped attaching member designed to be attached around the neck 232. Transmitter 141 is located inside one end of attaching member 230, while reception position controller 170 is located inside the other end of attaching member 230. Receiver 142 is attached to reception position controller 170. In the state shown in the figure, transmission path L, which extends from transmitter 141 to receiver 142, passes through the right carotid artery 231. The numeral 233 in the figure indicates the bones of the neck.

Figure 26:
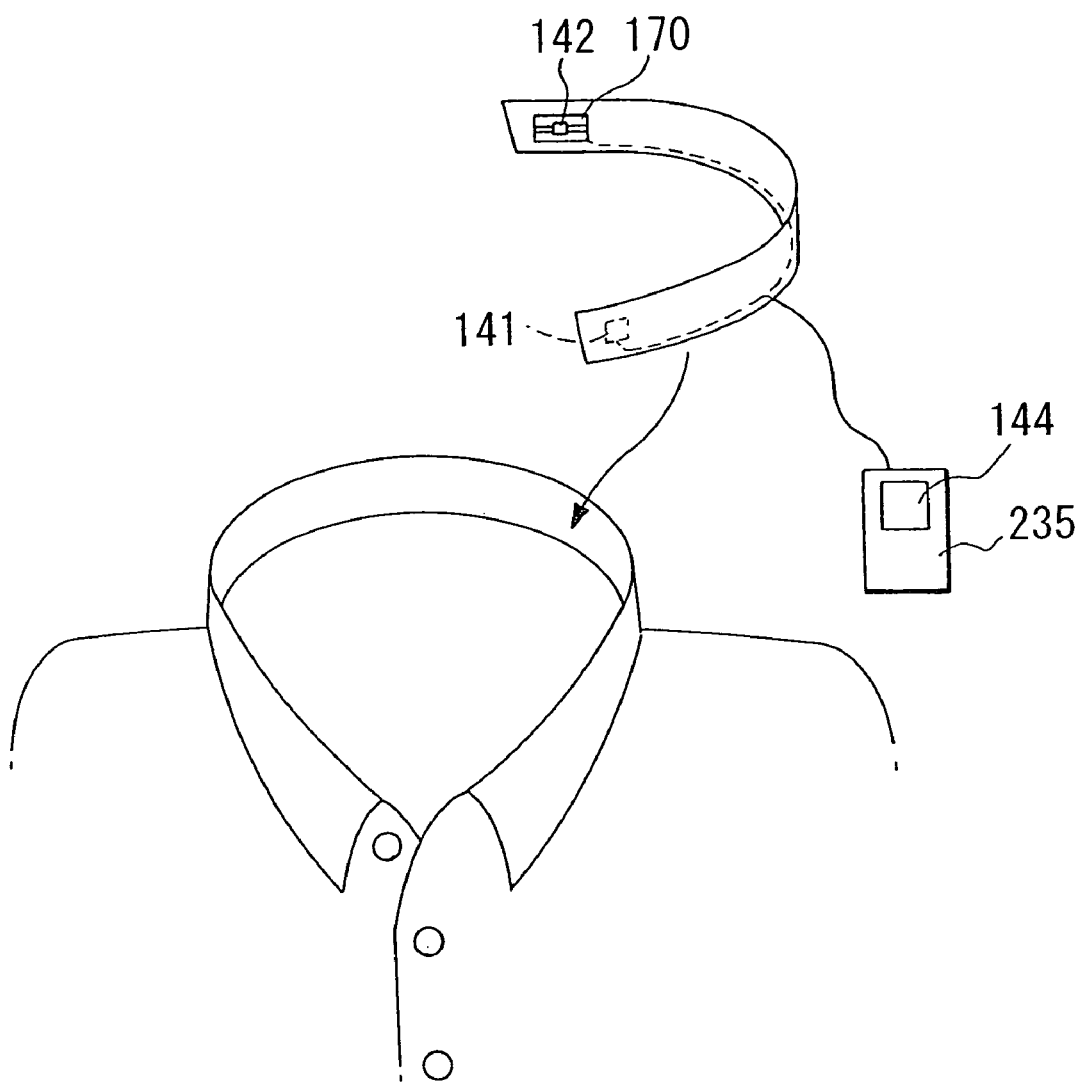
FIG. 26 is a perspective view for explaining the state of attachment of the seventh embodiment.

As shown in FIG. 26, attaching member 230 is designed to be attached to the inside of a shirt collar. A wire runs from receiver 142 and reception position controller 170, and attaches to control box 235. Control box 235 is provided with a transmission path measuring means 143, display 144, and pulse wave detecting circuit 145. The size of control box 235 is such that it can be placed inside a shirt pocket, for example.

The action of an embodiment having the above-described design is the same as that of the sixth embodiment.

I-1: Modification of Embodiment 7

(1) In place of reception position controller 170, it is also acceptable to employ a design in which receiver 142 is manually moved, as in the fifth-embodiment. Moreover, the device may be designed so that either receiver 142 or transmitter 141 can be moved, or so that both can be moved.

(2) Attaching member 230 for detecting the pulse wave in the carotid artery is not limited to the design described above. It may also be in the form of a necklace, the loop portion of a necktie, or of a shape which encircles the neck, for example. In summary, any design is acceptable provided that it holds transmitter 141 and receiver 142 in place so that the transmission path L linking transmitter 141 and receiver 142 passes through the carotid artery.

Figure 27:
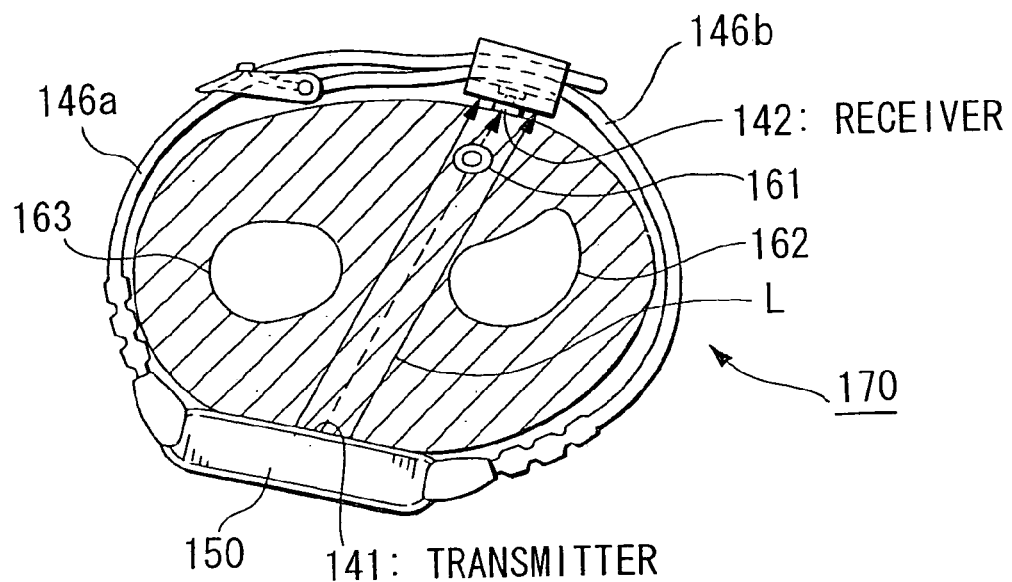
FIG. 27 is a cross-sectional diagram showing a modification in the case where ultrasonic waves are employed as the wave.

J: Other Embodiments, Effects (1) The preceding embodiments employed examples in which measurements were carried out using a planar polarized light laser. However, the waves used for measurements are not limited thereto. Light emitted from an LED may also be used, for example, as may ultrasonic waves. An example employing ultrasonic waves is shown in FIG. 27. In this example, an ultrasonic wave vibrating element is used for transmitter 141 and receiver 142, respectively. In this example, the amplitude of the ultrasonic wave which is propagated to receiver 142 changes in response to the pulsation of the blood (because the damping quantity of the ultrasonic wave changes in response to the blood capacity of the vessels). Thus, the pulse wave can be measured by detecting this change. The positional matching of transmission path L is carried out in the same manner as in the sixth embodiment. In addition, sliding member 147 may be used in place of reception position controller 170.

(2) Because the preceding embodiments and modifications are attached to the body, it is also acceptable to provide a design in which the component accompanying movement of the body (body motion component) is removed. For example, an acceleration sensor or the like may be disposed so that the body motion is communicated thereto, and the body motion component detected based on the signal from the acceleration sensor. The body motion component is removed from the received signal output by receiver 142, and then detection of the pulse wave and the amplitude of the reception signal is performed based on the signal which results after removal of the body motion component. As a result of this design, the noise due to body motion can be removed, enabling accurate setting of the transmission path and measurement of the pulse wave.

(3) When a propagating medium other than another laser is employed, then the transparent film shown in FIG. 23 may be made of a material which does not damp that medium.

(4) Transmitter 141 and receiver 142 do not need to press against the body, nor it is necessary to control the pressing force at a constant level, in the preceding embodiments and modifications. Rather, it is sufficient if transmitter 141 and receiver 142 contact the body in a natural state as in the case where a watch or accessory is worn on the body. Further, this invention detects the pulse wave based on the amplitude of the received wave. Thus, even if the state of attachment or pressing force of transmitter 141 and receiver 142 on the body changes, so that the distance between the two changes, this change in distance has absolutely no effect. Accordingly, measurements can still be made while maintaining a high SN.

Figure 28:
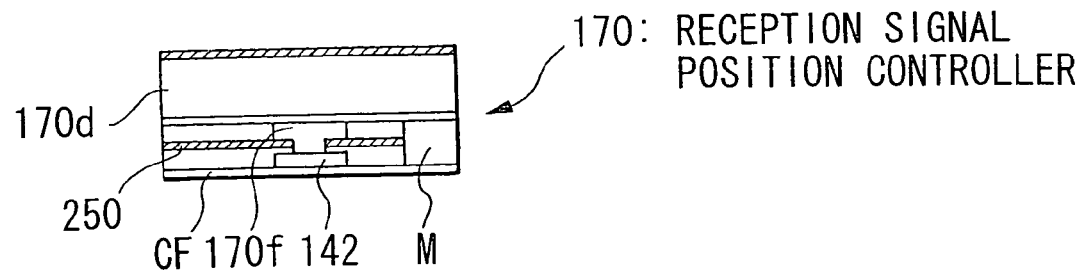
FIG. 28 is a block diagram showing another example of reception position controller 10.

(5) The reception position controller 170 used in the sixth and seventh embodiments employed a linear motor design. In place thereof, however, it is also acceptable to drive the receiver using a mechanical design. An example of this case is shown in FIG. 28. Note that the same numerical symbols have been applied to components which are common to those shown in FIG. 23.

The symbol M indicates a motor in FIG. 28. 250 is a ball screw attached to the axis of motor M, sharing an axial center therewith. 170f is a base member to which receiver 142 is attached, base member 170f engaging with ball screw 250. As the ball screw is rotated, base member 170f moves from left to right in the figure in response to the direction of that rotation. The amount of movement is proportional to the amount of rotation of ball screw 250. As a result of the above structure, reception position controller 170 drives receiver 142 about the circumferential direction of the arm (i.e., in a direction perpendicular to the radial artery).

Figure 29:
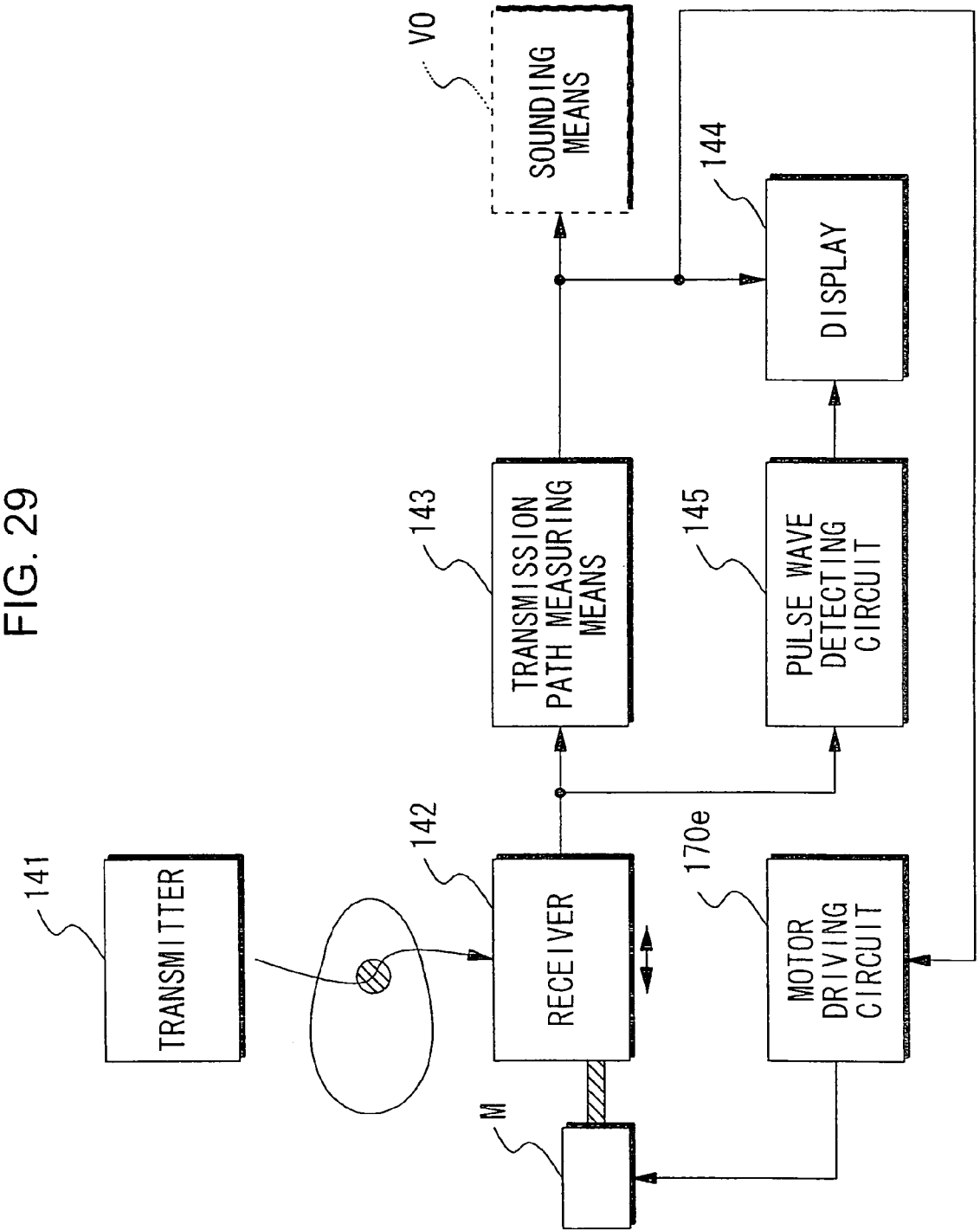
FIG. 29 is a block diagram showing the control circuit for reception position controller 10 shown in FIG. 17.

FIG. 29 shows the structure of a circuit for carrying out rotational control of motor M. The structure shown in this figure is roughly equivalent to the electrical structure of the fifth and sixth embodiments.

When the measuring mode is set in the above-described design, transmission path measuring means 143 begins to output the amplitude of the received signal. Motor driving circuit 170e rotates motor M, which is to move receiver 142 to the right by one pitch, in a specific direction (clockwise, for example). A determination is then made as to whether or not the amplitude of the received signal has increased. If the amplitude is larger, then receiver 142 is moved one pitch further to the right, and a determination is then made again as to whether or not the amplitude has increased. The operation is repeated subsequently with receiver 142 moved to the right, until the amplitude value decreases, at which time receiver 142 is moved back one pitch to the left (i.e., the motor M is rotated in a specific direction (counterclockwise, for example)), and movement of receiver 142 is concluded. In the case where the amplitude decreases the first time receiver 142 is moved to the right by one pitch, then the direction of movement is immediately switched to the left, and the operation as described above is carried out.

As a result of the preceding operation, receiver 142 is controlled so that it is located at the position where the reception amplitude is maximal. In other words, transmission path L is set to be at a position where it passes through the arterial vessel. As in the case of the sixth embodiment, since receiver 142 does not press against the skin in this case, the force with which receiver 142 is moved along the surface skin of the arm is limited. Accordingly, sufficient servo-actuated control is possible by means of the torque of a typical micro-motor. Further, given the relationship between the width of transmission path L and the diameter of the arterial vessel, the optimal position for transmission path L can be found by moving receiver 142 about 1 cm.

Note that in the example shown in FIG. 28, a film CF, which transmits laser light, is attached to the boundary surface between reception position driver 170 and the skin. However, provided that there is no problem with sliding receiver 142, this film CF may be omitted. In addition, it is of course acceptable to drive the transmitter using a structure equivalent to reception position controller 170.

(6) When taking into consideration the supply from the power source in the above-described embodiments and modifications, transmitter 141 was provided in the main body 150 of the wristwatch, while receiver 142 was provided in sliding member 147. However, the present invention is not limited thereto. Rather, transmitter 141 may be provided in sliding member 147, and receiver 142 may be provided in main-body 150.

Figure 30:
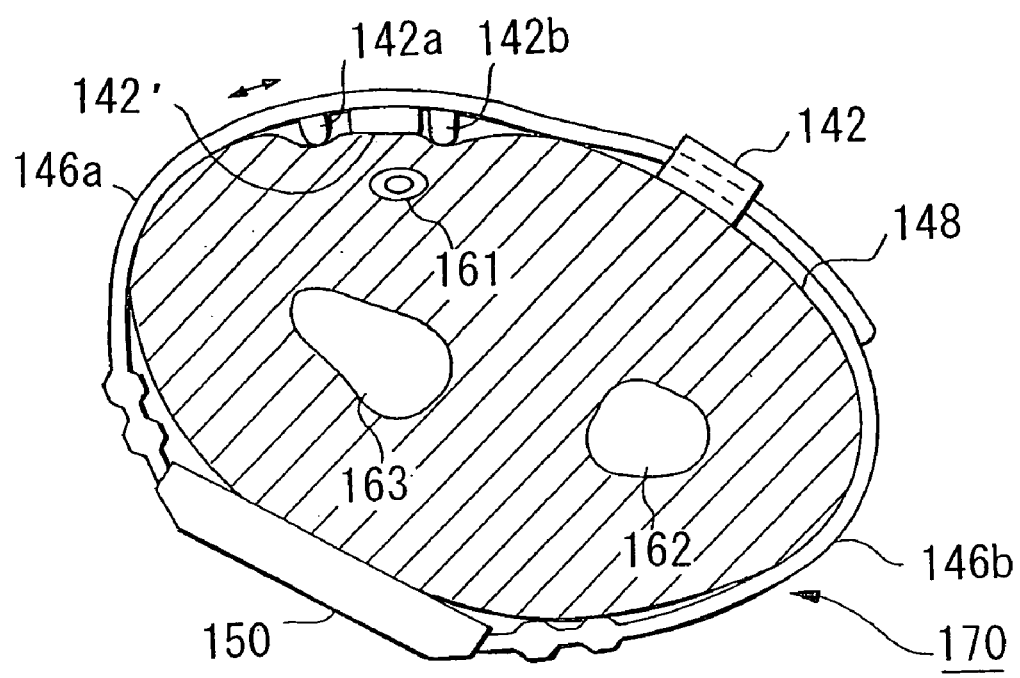
FIG. 30 is a cross-sectional diagram of the state of attachment to the arm of a photoelectric reflecting type pulse wave detecting device.

(7) Pressure legs 142a,142b may be provided to the end of sliding member 147 in the above-described embodiments and modifications. This point will be explained with reference to FIG. 30. FIG. 30 is a cross-sectional view of an arrangement in which a photoelectric reflecting type pulse wave detector is attached to the arm. Wrist bands 146a,146b attached to the ends of main body 150 are wrapped around the subject's wrist, and fastened together using a conventional hook 240. Hook 240 enables adjustment of the circumference of wristwatch 170, i.e., adjustment of the closing force about the wrist.

An optical pulse detecting sensor 142' is fixed to the back (i.e., the surface facing the wrist) of wrist band 146a. A pressure detecting sensor may also be used in place of optical pulse detecting sensor 142'. Optical pulse detecting sensor 142' is designed so that the transmitter and receiver are formed in a unitary manner. Under the closing force of wrist bands 146a,146b, optical pulse detecting sensor 142' presses on the surface of the skin from directly above radial artery 161.

Pressure legs 142a,142b are provided on wrist band 146a, projecting outward therefrom. At least one of pressure legs 142a,142b can be moved along the circumferential direction of wrist band 146a, and stopped at a new position.

In this case, pressure legs 142a,142b are depressed into the highly elastic (soft) surface at the side of radial artery 161, so that the position of optical pulse detecting sensor 142' can be easily positioned above radial artery 161. The end of optical pulse detecting sensor 142' is positioned higher than the ends of pressure legs 142a,142b. As a result, the positioning of radial artery 161, which is less elastic (harder) than other tissues, between pressure legs 142a,142b can be easily determined.

Accordingly, by providing pressure legs 142a,142b of this type to the end of sliding member 147 (see FIG. 18 and FIG. 24), rough positioning can be carried out. Thereafter, by carrying out precise positioning using sliding member 147, accurate positioning can be determined easily. Thus, the SN ratio of the pulse wave signal can be improved.

Radial artery 161 is typically located at a position about 3 mm below the skin. Thus, positioning may be determined using only pressure legs 142a,142b by pressing them against the skin. Although there is a slight deterioration in the SN of the pulse wave signal as compared to the case when sliding member 147 and pressure legs 142a,142b are employed, this is not a problem in terms of practical application.

(8) The radial artery 161 in the wrist or carotid artery 231 in the neck were employed as examples of positions on the body for detecting the pulse wave in the preceding embodiments and modifications. The present invention is not limited thereto, however. Rather, any vessel is acceptable provided that the artery corresponds to a position for detecting the pulse wave. In other words, there are various arterial vessels in the human body as shown in FIG. 31. Provided that the above-described embodiments of the pulse wave detecting device are modified to fit the detection sites, however, the pulse wave can be detected at these various vessels.

K: Embodiment Eight

Next, various embodiments of the present invention's reflected light detector which reduces the impact of external light by using polarized light and a light receiving element employing a optical resonator, and a pulse wave detecting device employing this reflected light detector will now be explained with reference to the figures.

The eighth embodiment of the present invention will be explained first. FIG. 32A shows the rough structure of the reflected light detector 301 according to this eight embodiment of the present invention. As shown in this figure, reflected light detector 301 is formed of a light emitting element 310, light receiving element 320, polarizing plates 331,332 and filter 340 provided on the light receiving surface side of the light receiving element. Reflected light detector 301 is designed to emit light onto the dispersing medium where detection is to be performed, and then receive this reflected light. Polarizing plate 331 is provided on the light emitting surface side of light emitting element 310, and polarizing plate 332 is provided on the light receiving surface side of light receiving element 320. The direction of polarized light from the polarizing plates is the same. For this reason, polarizing plates 331,332 may be formed as one plate rather than being separated into light emitting and light receiving sides.

Although this structure is abbreviated in the figures, light emitting element 310 and light receiving element 320 are separately housed, so that light emitted by light emitting element 310 does not directly fall on light receiving element 320.

Since various situations may be considered with respect to the dispersing medium, including flowing through a tube through which light passes, or floating in a free space, no specific case is shown in these figures.

In a reflected light detector 301 of this design, the light emitted by light emitting element 310 is polarized by polarizing plate 331, and emitted onto the dispersing medium. Of this emitted light, there is light which reaches the dispersing medium and is absorbed, as well as a component that is reflected. Of this reflected light, some undergoes repeated multiple dispersion and some directly approaches light receiving element 320.

This multiply dispersed light, which has undergone repeated multiple dispersion in the dispersing medium, does not maintain its polarization state at the time of emission. Thus, only a portion of this light passes through polarizing plate 332. Light which is not multiply dispersed, i.e., directly reflected light, maintains the polarization state at the time of emission. Thus, a major part of this light passes through polarizing plate 332.

Accordingly, the major portion of light which has passed through polarizing plate 332 and falls on light receiving element 320 is a directly reflected light component which has not undergone multiple dispersion in the dispersing medium.

When the dispersing medium is flowing through a tube, the directly reflected light arises not only from the dispersing medium, but also from the tube itself. However, assuming that the tube is hard, then the directly reflected light component due to this tube is constant and may be easily canceled. On the other hand, if the tube is soft, then it also pulses in response to changes in the volume of the dispersing medium flowing through it. Thus, the directly reflected light component due to the tube also expresses information relating to the dispersing medium.

(1) Receiver

Figure 33A:
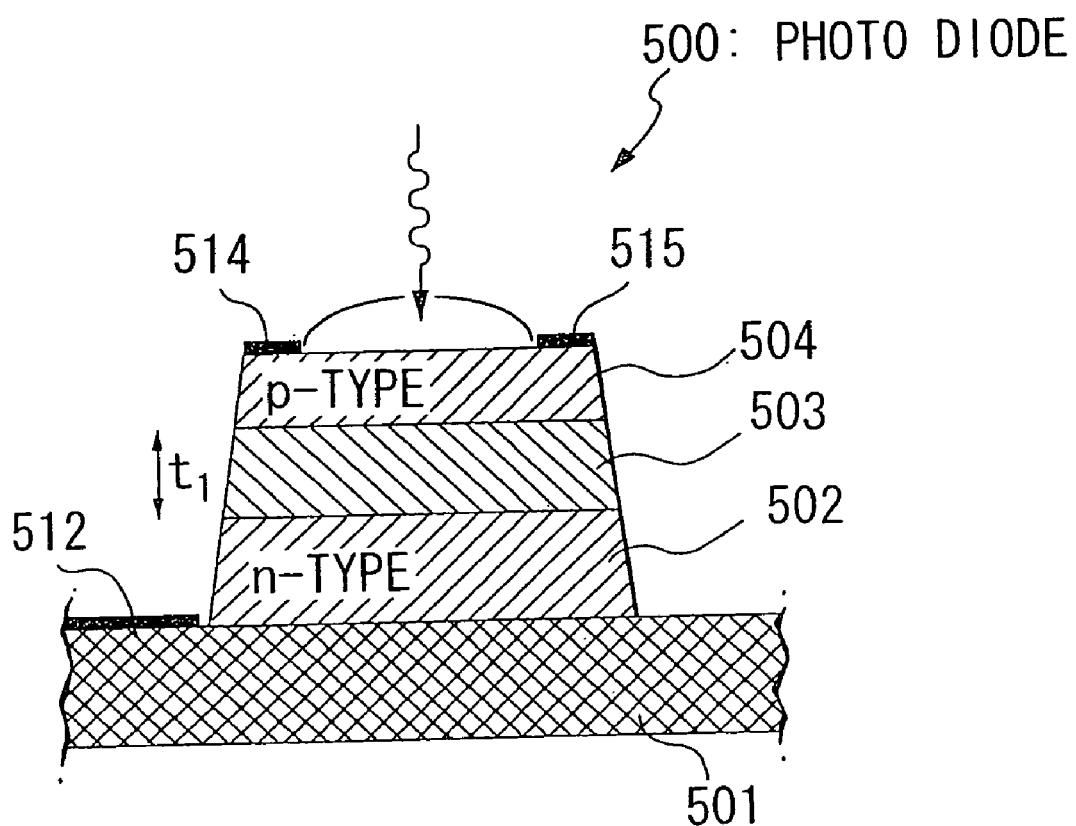
FIG. 33($a$) is a lateral cross-sectional view showing the structure of an optimal photodiode employed as the present invention's light receiving element.

The various parts of this embodiment will now be explained, beginning with receiver 320 for the convenience of discussion. FIG. 33A is a lateral cross-sectional view showing the structure of photo diode 500 which is optimally employed as light receiving element 320 in the eighth embodiment.

As shown in the figure, photo diode 500 is formed by successively laminating an n-type layer lower mirror 502, a depletion layer 503, and a p-type layer upper mirror 504 onto a substrate (wafer) 501, and is designed to have an optical resonator consisting of lower mirror 502 and upper mirror 504. The resonance wavelength $\lambda_r$ of this optical resonator is determined from the following formula based on the interval of space between lower mirror 502 and upper mirror 504, i.e., the thickness $t_1$ of the depletion layer, and the index of refraction n of the depletion layer.

$$\lambda_r = 2n \cdot t_1 / m \tag{1}$$

In this formula, an integer of 1 or greater is employed for m. However, the design typically employs an m value of 1 or 2 so that a large interval between resonance wavelengths can be achieved.

Figure 33B:
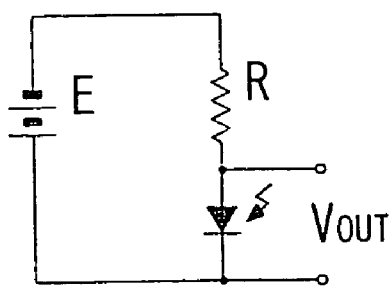

Electrode 512 is formed on the lower layer of lower mirror 502 and electrode 514 is formed on the upper layer of upper mirror 504. As shown in FIG. 33B, a DC electrical source E and a resistor R are connected in series to both electrodes and backward biased. An opening 515 is provided to upper mirror 504. Light reflected by the scattering medium falls on opening 515. The received light is amplified due to the excitation of light traveling within the optical resonator and generates a conduction electron-hole pair in depletion layer 503. Accordingly, a current proportional to the quantity of light reaching depletion layer 503 flows from lower mirror 502 to upper mirror 504. Thus, by extracting the voltage between electrodes 512 and 514 as output signal Vout, the quantity of light received at photo diode 500 can be detected.

It is ideal if lower mirror 502 and upper mirror 504 have high reflection coefficients over the entire wavelength region. However, obtaining such reflection characteristics is difficult as a practical problem. Therefore, these embodiments are designed so that the reflection coefficient is high in a band of a specific width that includes the resonance wavelength of the resonator.

For this reason, upper mirror 504 is formed by alternately laminating a material having a high detraction index and a material having a low detraction index. The wavelength region having a high reflection coefficient is determined by the difference between the detraction indices of the laminating materials. The larger this difference, the wider the band. Thus, it is preferable that the material employed for upper mirror 504 be a combination of materials that have a large difference in detraction indices. For example, when employing a AlGaAs-type semiconductor, the upper mirror may be formed by laminating a material which changes the ratio of Al and Ga. Note that the same structure applies for lower mirror 502.

Note that in the example in the figure, upper mirror 504 is a p-type semiconductor. In this case, even if the ratio of Al and Ga is varied, the wavelength region in which there is a high reflection coefficient cannot be widened that much. For this reason, a conductor is preferably used for the material of the mirror. However, in the case where the upper mirror is formed onto the conductor, the conductor serves as an insulating body. Thus, the structure formed is not that shown in FIG. 33A, but rather a structure in which a lower mirror, depletion layer, p-type layer, electrode with opening, and upper mirror consisting of a conductor are laminated in order from the bottom. In this case, a material having a high refraction index ($TiO_2$, $Ta_2O_5$, etc.) and a material having a low refraction index ($SiO_2$, MgF, etc.) can be used. In particular, when $TiO_2$ and $Ta_2O_5$ are employed, the difference in refraction indices can be increased, so that a wavelength band on the order of 400 nm can be maintained.

Next, the characteristics of a light receiving element 320 having a structure such as described above will be investigated.

Figure 34A:
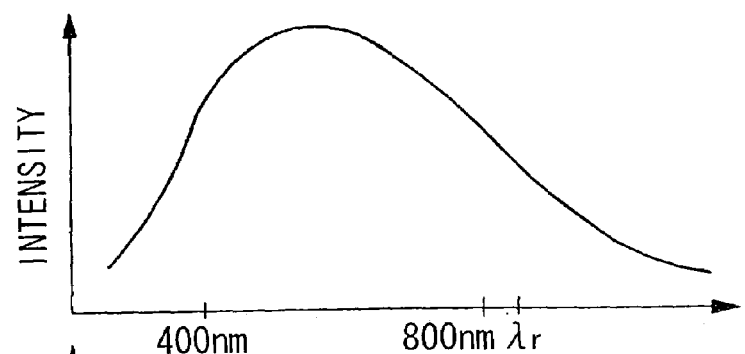
FIGS. 34($a$)–($e$) are respective diagrams for explaining the optical characteristics of the photo diode.

The external light spectrum was assumed to have the characteristics such as shown in FIG. 34A. The reason for setting the wavelength of the light which is ultimately detected by light receiving element 320 in a wavelength region which is not readily effected by external light is as explained above. Thus, an explanation will be made of the case where the wavelength detected by light receiving element 320 is wavelength $\lambda r$, at which the intensity of the external light spectrum is reduced.

Figure 34B:
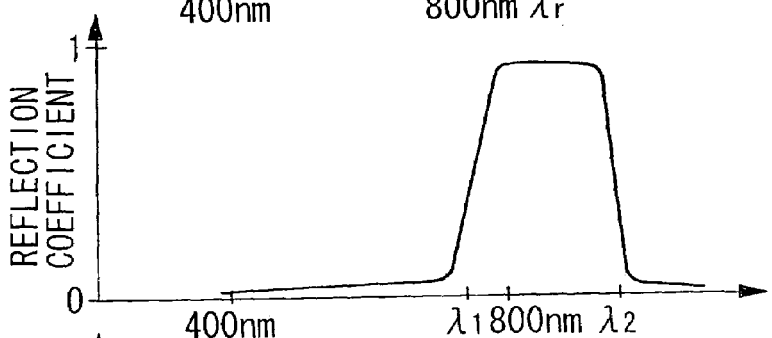

Lower mirror 502 and upper mirror 504 are formed to satisfy the following conditions. First, both mirrors are formed by laminating an appropriate material so that the mirror's reflection coefficient increases in the region including wavelength $\lambda r$ (see FIG. 34B). Second, both mirrors are formed with a distance (thickness) ($t1$) therebetween so that the resonator wavelength of the optical resonator becomes wavelength $\lambda r$. For the sake of convenience in this explanation, the band in which the mirrors' reflection coefficients are high are defined as between wavelength $\lambda 1$ and $\lambda 2$, respectively.

Figure 34C:
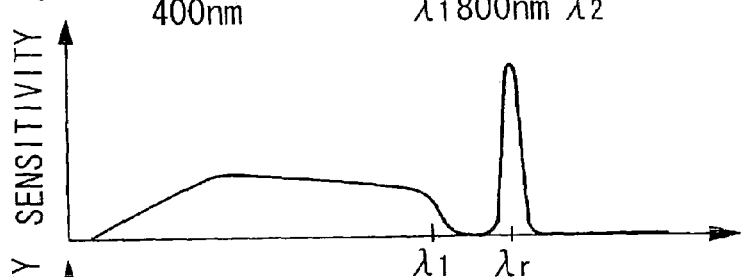

The sensitivity characteristics of a light receiving element 320 formed in this way are shown in FIG. 34C. As shown in this figure, the degree of sensitivity is, (1) acute at wavelength $\lambda r$, and (2) falls below wavelength $\lambda 1$. This is believed to be mainly due to the following reason. Namely, the reason for (1) is that, while the mirror's reflection coefficient increases at wavelength $\lambda r$, the incidented light is absorbed by the depletion layer while being cycled between the mirrors by means of a Fabry-Perot resonator. The reason for (2) above is that the received light passes through the upper mirror 504 since the mirror's reflection coefficient is not high below wavelength $\lambda 1$. However, since the depletion layer is thin, a portion of the light is absorbed by the depletion layer and converted to an electrical current while most of the light passes through the depletion layer. Thus, while the sensitivity below wavelength $\lambda 1$ is not high, it is also not zero. Note that it is believed that the reason that the sensitivity decreases slightly to the right is that the mirror's reflection coefficient increases slightly to the right at wavelengths below wavelength $\lambda 1$. In addition, even if the reflection coefficient is low, the sensitivity in the region where the wavelength is long is essentially low. Thus, there is almost no sensitivity in the region above wavelength $\lambda 2$ or higher.

Figure 34D:
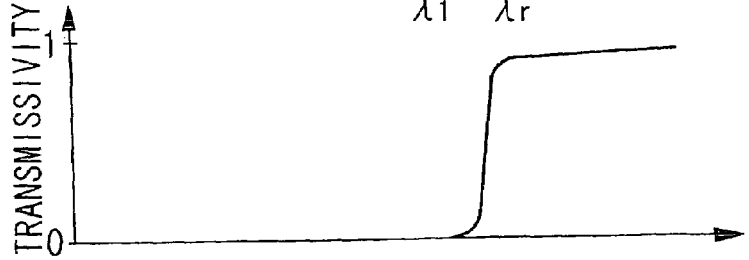

As shown in the figure, the sensitivity of this type of light receiving element 320 increases in the region below wavelength $\lambda 1$, so that, without modification, the effect of the external light component is large. Therefore, a filter 340 having transmission characteristics such as shown in FIG. 34D is provided on the receiving surface side of light receiving element 320. Provided there is a difference between blocked wavelength $\lambda 1$ and transmitted wavelength $\lambda r$, then such sharp transmission characteristics are not demanded of filter 340. Thus, an inexpensive and easily produced absorption-type glass filter or plastic filter may be used for filter 340.

Figure 34E:
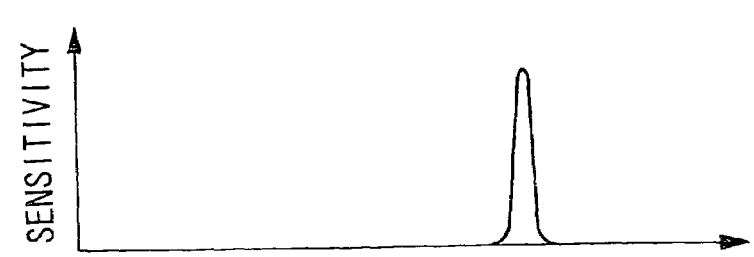

The sensitivity characteristics of light receiving element 320 when combined with a filter 340 are shown in FIG. 34E. As shown in this figure, light below wavelength $\lambda 1$ is cut by filter 340, so that sharp characteristics can be obtained for the sensitivity characteristics at wavelength $\lambda r$ where the influence of external light is small.

(2) Light Emitting Element

Light emitting element 310 will now be explained. The present invention is designed so that the wavelength of the light employed is selected by filter 340 and light receiving element 320. Thus, light emitting element 310 is acceptable provided that it generates light that includes the wavelength $\lambda_r$ which is ultimately detected by light receiving element 320. Accordingly, a regular light emitting diode may be employed for light emitting element 310. More preferable, however, is a planar emission semiconductor laser such as shown in FIGS. 4 through 7.

Figure 35:
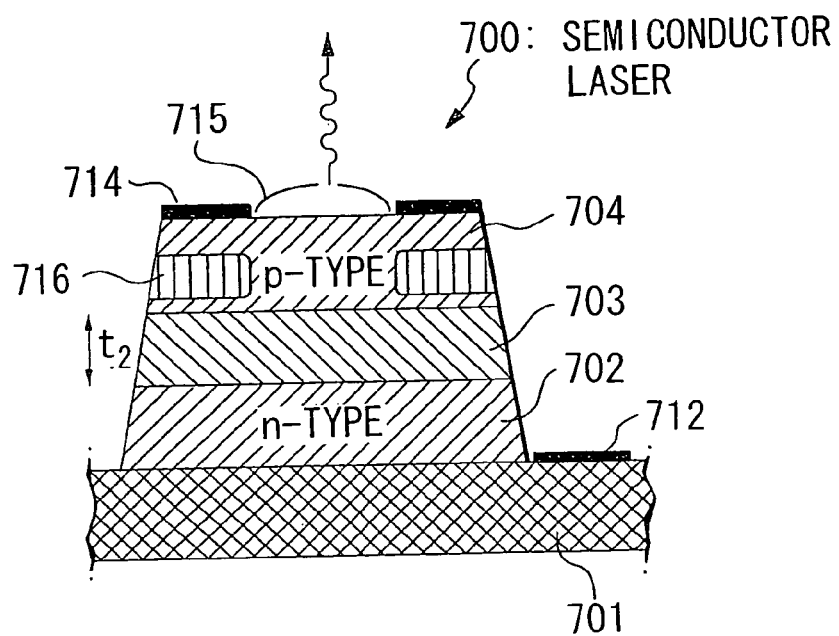
FIG. 35 is a lateral cross-sectional view showing the structure of an optimal semiconductor laser employed as the light emitting element in the present invention.

FIG. 35 is a cross-sectional view from the side showing the structure of an optimal planar emission semiconductor laser 700 employed for light emitting element 310 in the eighth embodiment. It has basically the same structure as the planar emission laser shown in FIG. 4. As shown in this figure, planar emission semiconductor laser 700 is formed by sequentially laminating an n-type layer lower mirror 702, active layer 703, and p-type layer upper mirror 704 onto a substrate (wafer) 701. Planar emission semiconductor laser 700 has one type of optical resonator consisting of lower mirror 702 and upper mirror 704. The resonance wavelength of this optical resonator is determined by the interval of space between lower mirror 702 and upper mirror 704, i.e., the resonator length $t_2$.

Electrode 712 is formed on the lower layer of lower mirror 702, and electrode 714 having an opening 715 is formed in the upper layer of upper mirror 704. Electrodes 712 and 714 are forward biased.

In semiconductor laser 700, when a conduction electron and a hole are injected from electrodes 712 and 714 respectively, the carriers for these continue diffusing, to reach active layer 703. It is preferable to provide a bottlenecking layer 716 here, so that the carrier injected from upper electrode 704 accumulates in active layer 703 which is directly below opening 715. The conduction electron and hole that reach active layer 703 bond again, and are discharged as light. The discharged light travels within the optical resonator, and induces stimulated emission when passing through active layer 703. As a result, light having a large output is closed within the optical resonator, with a portion thereof passing through upper mirror 704 and being released as laser light.

Figure 36:
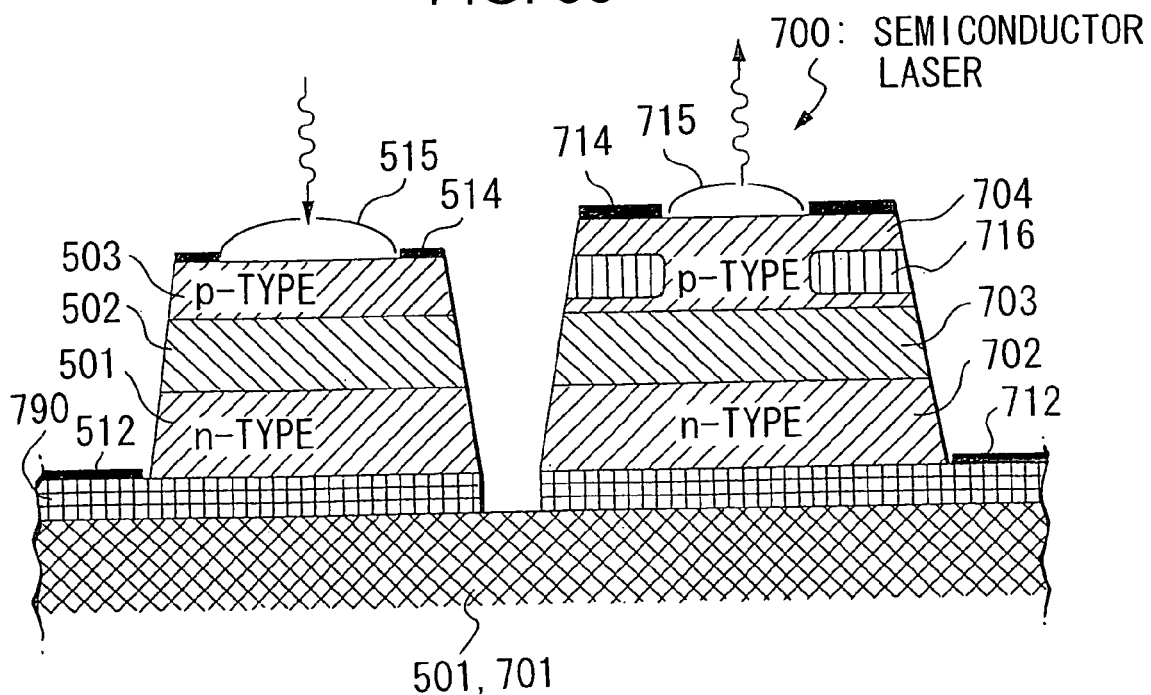
FIG. 36 is a lateral cross-sectional view showing the structure when a photo diode and a semiconductor laser are formed onto the same wafer.

It should be noted that the structure of the semiconductor laser 700 employed here is fundamentally common to the structure of photo diode 500 shown in FIG. 33. The oscillating wavelength and the sensitivity wavelength are both determined by the resonator length $t_2$ and the thickness $t_1$ of the depletion layer. Accordingly, if these elements are formed on the same substrate 501 (701) wafer via insulating layer 790 (FIG. 36) with the active and depletion layers thereof formed by the same layer growth process, then it is not only easy to select a wavelength for the employed light in a band that is not readily effected by external light, but it is also possible to bring together the oscillating wavelength and the sensitivity wavelength.

Note that when forming photo diode 500 and semiconductor laser 700 on the same substrate, the distance between photo diode 500 and semiconductor laser 700 is on the order of 20 to 30 microns. Thus, it is extremely difficult to provide different respective polarizing plates for photo diode 500 and semiconductor laser 700. However, it is not necessary to form photo diode 500 and semiconductor laser 700 in a unitary manner during the step of forming reflected light detector 1. Rather, it is also possible to employ the two as a pair after separating them. Thus, as described in a subsequent modification, if the directions of polarization on the emitting side and the receiving side are made to differ (i.e., the dispersed light component is detected), then photo diode 500 and semiconductor laser 700 can be separated and used as a pair. On the other hand, if the directions of polarization on the emitting side and the receiving side are made to coincide (i.e., the directly reflected light component is detected), then photo diode 500 and semiconductor laser 700 can be employed as a single chip without being separated.

Similarly, it is difficult to provide a filter 340 only on the receiving side. In this case, the wavelength of the light generated on the emitting side coincides with the sensitivity wavelength and passes through filter 340. Thus, a design is acceptable in which a filter is provided on both the receiving side and the emitting side.

In the reflected light detector 301 according to the eighth embodiment of the present invention, the light which passes through light polarizing plate 332 and filter 340 and is ultimately detected by light receiving element 320 is light of wavelength $\lambda_r$, on which the effect of external light is small, and which has a high proportion of directly reflected light components which are not multiply dispersed in the dispersing medium. For this reason, it becomes possible to detect only the directly reflected light components out of the light reflected by the dispersing medium while reducing the influence of external light.

Note that filter 340 is employed with the objective of cutting light having a wavelength of $\lambda_1$ or less from the reflected light falling on the light receiving element. Thus, either polarizing plate 332 or filter 340 may be disposed on the top surface.

K-1: Modifications of the Embodiment 8

An explanation will now be made of various modifications for the structural elements of the eighth embodiment.

(1) Angle of the Polarizing Plate

The preceding eighth embodiment employed a design in which polarizing plates 331,332 having the same polarizing direction were used at the light emitting surface of light emitting element 310 and the light receiving surface of light receiving element 320 in order to detect reflected light components which were not multiply dispersed by the dispersing medium. However, a design may also be considered in which the multiply dispersed reflected light is detected.

In the case of this latter design, the polarizing directions of polarizing plates 331,332 at the light emitting surface of light emitting element 310 and the light receiving surface of light receiving element 320 are designed to be perpendicular to one another.

The light emitted in this design is polarized by polarizing plate 331 and emitted onto the dispersing medium. Of this emitted light, there is light which reaches the dispersing medium and is absorbed, and there is also reflected light. Further, of this reflected light, there is light which is repeatedly multiply dispersed, and there is also light which directly advances toward light receiving element 320.

Because this directly reflected light maintains the polarization state at the time of emission, it does not pass through polarizing plate 332. However, multiply dispersed light does not maintain its polarization state at the time of emission, so that some of it passes through polarizing plate 332. Accordingly, the light which has passed through polarizing plate 332 and falls on light receiving element 320 is the component which shows the multiply dispersed light out of the light reflected by the dispersing medium. For this reason, by using the output signal Vout from light receiving element 320, it is possible to detect the light component which has undergone multiple dispersion in the dispersing medium while reducing the influence from the external light components.

The direction of polarization of polarizing plates 331,332 does not have to be the same or perpendicular to one another. Rather, one of the polarizing plates may be rotated with respect to the other polarizing plate, with the light receiving element 320 designed so as to receive light polarized in some optional direction.

(2) Canceling the External Light Component

In order to reduce the effect of external light in the preceding eighth embodiment, the wavelength of the light finally detected by light receiving element 320 was designated as $\lambda r$. However, as may be inferred from the spectral characteristics for external light as shown in FIG. 34A, it is not possible to reduce the influence from external light to zero.

Figure 37:
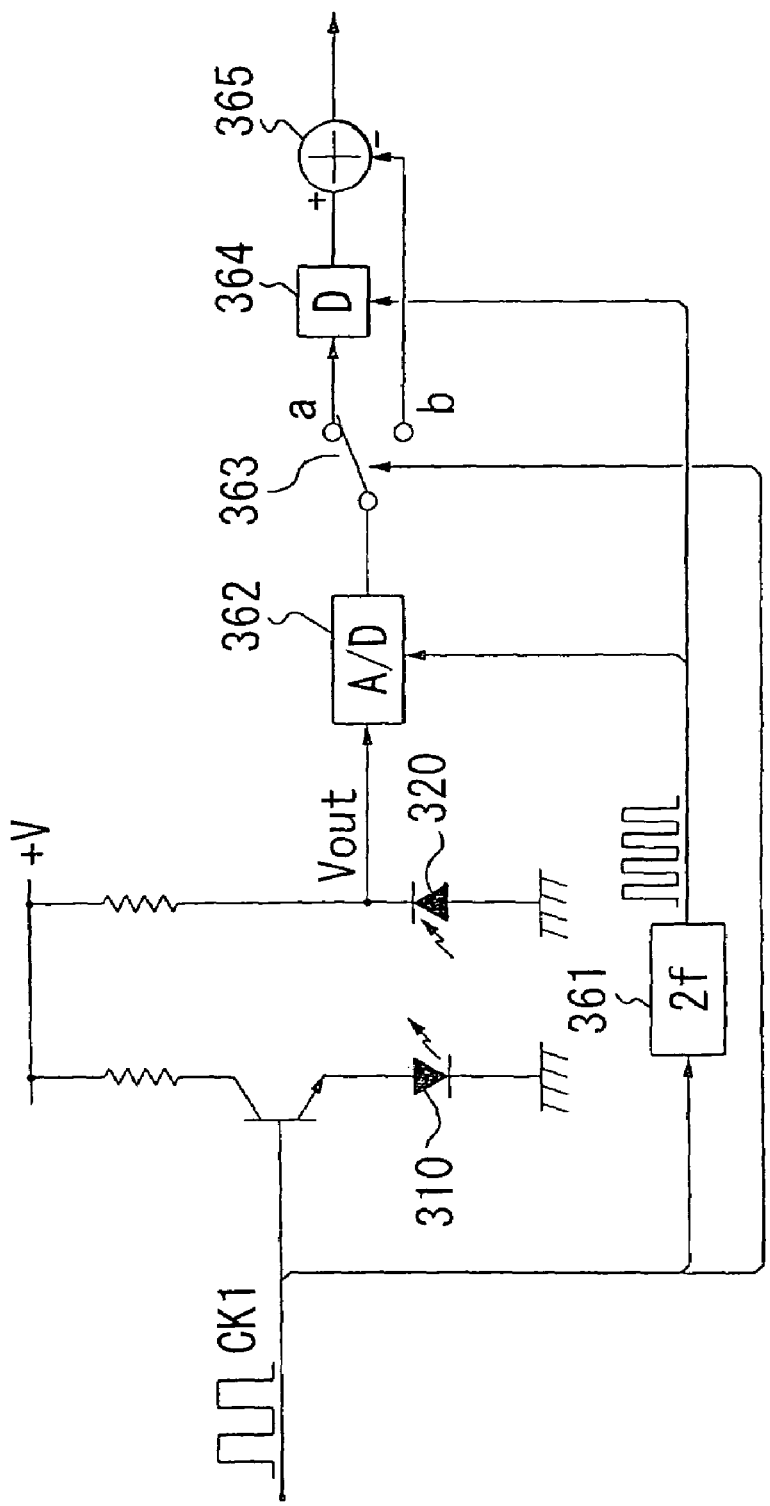
FIG. 37 is a block diagram showing the structure for canceling the external light component in the eighth embodiment.

A design will now be explained for even further reducing the influence of external light. FIG. 37 is a block diagram showing the electrical structure thereof.

In this figure, the numeral 361 indicates a frequency multiplier which doubles the frequency of signal CK1, and outputs the doubled signal CK2. A/D converter 362 samples and holds the signal Vout output from light receiving element 320 when signal CK2 is falling, and converts this value to a digital signal. Switch 363 selects output terminal a when signal CK1 is at level [H]. At all other times, switch 363 selects output terminal b. Numeral 364 is a delay element for delaying the input signal by just the period of signal CK2.

In this design, when signal CK1 is at level [H], light emitting element 310 is turned on (illuminated), while when signal CK1 is at level [L], light emitting element 310 is turned off (extinguished). A/D converter 362 samples and holds the output signal Vout when signal CK2, which has a frequency twice that of signal CK1, is falling. Thus, the digital signal therefore alternately expresses the quantity of received light when light emitting element 310 is on and when it is off. Switch 363 selects output terminal a when signal CK1 is at level [H], and selects output terminal b when signal CK1 is at level [L].

Thus, the digital signal for output signal Vout is separated such that when light emitting element 310 is on, it is supplied to output terminal a, while when light emitting element 310 is off, it is supplied to output terminal b. The timing for each of these is brought together by a delay element 364.

When light emitting element 310 is on, an external light component and a reflected light component due to the dispersing medium are superimposed in the signal output from light receiving element 320. In contrast, when light emitting element 310 is off, only the external light component is included in the signal output.

Thus, after bringing together the timing using delay element 364, subtracter 365 subtracts the digital signal when light emitting element 310 is off from the digital signal when light emitting element 310 is on. The value of this difference serves as a signal expressing only the reflected light component that does not include an external light component. Thus, it is possible to cancel the external light component.

Note that the period during which light emitting element 310 is on and the period during which light emitting element 310 is off are not equal in this design. Thus, strictly speaking, the external light component is not canceled from the reflected light component on which it is superimposed. However, if the frequency of signal CK1 for turning light emitting element 310 on and off is set sufficiently high, then this problem can be ignored, even in the case where the external light component varies over time. Conversely, the frequency of signal CK1 must be two-fold greater than the frequency of the information being obtained about the dispersing medium, or two-fold greater than the varying frequency of the external light component.

In addition to the design shown in FIG. 37, the external light component can also be canceled by means of a structure in which the former signal and the latter signal are smoothed by means of a smoothing circuit (low pass filter), and the latter signal is subtracted from the former signal; or by means of a structure in which the output signal from light receiving element 320 is subjected to a band pass filter, to remove the on/off frequency component of light emitting element 310.

(3) Circularly Polarized Light

A linearly polarized light from polarizing plates 331,332 was employed as the polarization method in the above-described eighth embodiment, however, the present invention is not limited thereto. For example, circularly polarized light may also be employed. In this case, if a linearly polarized light inclined at a 45 degree angle to the main axis of a ¼ wavelength plate falls on the wavelength plate, then circularly polarized light can be obtained and emitted on the dispersing medium. On the other hand, if circularly polarized light falls on the ¼ wavelength plate, then linearly polarized light inclined at a 45 degree angle with respect to the main axis thereof can be obtained.

In other words, the direction of polarized light in the present invention is viewed to include not only linearly polarized light, but also circularly polarized light. Also, in addition to a polarizing plate, the polarizing means includes a broad range of devices, such as a ¼ polarizing plate, the rotary polarization element explained below, optical resonator, inrush current controller and the like.

L: Embodiment 9

In the preceding eighth embodiment, light emitting element 310 and light receiving element 320 were employed as a set to detect either the directly reflected light component or the dispersed light component out of the light reflected by the dispersing medium. However, a design may also be considered in which both are detected simultaneously. Accordingly, the following arrangements may be considered for this purpose.

Namely, three designs may be considered as follows: (1) a design in which two sets of light emitting elements and light receiving elements are employed, with the directly reflected light component and the dispersed light component detected respectively by each of the light receiving elements; (2) a design in which one light emitting element and two light receiving elements are employed, the polarizing direction of each of the light receiving elements are set to be the same and perpendicular (counterclockwise when employing circularly polarized light) to the polarizing direction on the emission side, and the directly reflected light component and the dispersed light component are detected respectively by each of the light receiving elements; and (3) a design which employs a light receiving element and a light emitting element which complementarily emits light that is in same direction or perpendicular to the polarizing direction of the light receiving element, the light receiving element detecting the directly reflected light component when light having a direction identical to the polarizing direction is emitted, and detecting the dispersed light component when light polarized in the perpendicular direction is emitted.

Of these, design (1) is realized by combining the eighth embodiment with a modification thereof. Accordingly, designs (2) and (3) will be explained below as the ninth and tenth embodiments, respectively.

As shown in FIG. 38, reflected light detector 302 according to the ninth embodiment is formed with one light emitting element 310, two light receiving elements 320a, 320b, polarizing plates 331 and 332a,332b, which are provided on the light emitting surface side of light emitting element 310, and the light receiving surface side of light receiving elements 320a,320b, and filters 340a,340b which are provided respectively on the light receiving surface side. The direction of polarization of polarizing plate 332a on the light receiving side is the same as that of polarizing plate 331 on the light emitting side. The direction of polarization of polarizing plate 332b is perpendicular to that of polarizing plate 332. Accordingly, light receiving element 320a detects the light component directly reflected by the dispersing medium, while light receiving element 320b detects the dispersed light component.

Light emitting element 310, and light receiving elements 320a,320b are disposed in the same plane in FIG. 38. The distance between light emitting element 310 and light receiving element 320a, and the distance between light emitting element 310 and light receiving element 320b, are equal. This is because it is preferable that the light emitted by light emitting element 310 be received by light receiving elements 320a,320b under equivalent conditions. In addition, the structure is simplified in the figure. Namely, light emitting element 310 and light receiving elements 320a, 320b are housed separately, so that the light emitted by light emitting element 310 does not directly fall on light receiving elements 320a,320b. Note that a single plate may be employed for polarizing plate 331,332a since their directions of polarization are the same. In addition, since the same characteristics are demanded of filters 340a,340b, they also may be formed out of the same plate rather than being divided.

By using light receiving elements 320a,320b employed in reflected light detector 302 according to the ninth embodiment which are the same as light receiving element 320 employed in the eighth embodiment, and matching the characteristics of filters 340a,340b, it is possible to simultaneously detect both the directly reflected light component and the dispersed light component in the light reflected by the dispersing medium. Thus, even more information can be obtained about the dispersing medium.

M: Embodiment 10

Figure 39A:
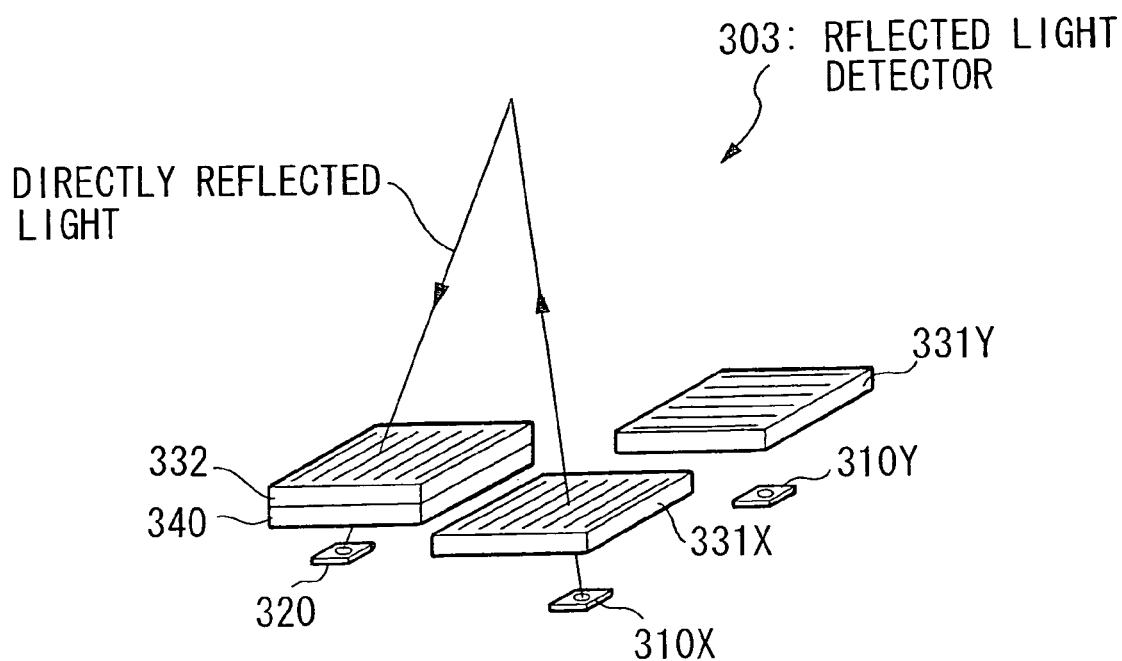
FIGS. 39($a$) and ($b$) are rough structural diagrams showing the structure of the reflected light detector according to a tenth embodiment of the present invention.
Figure 39B:
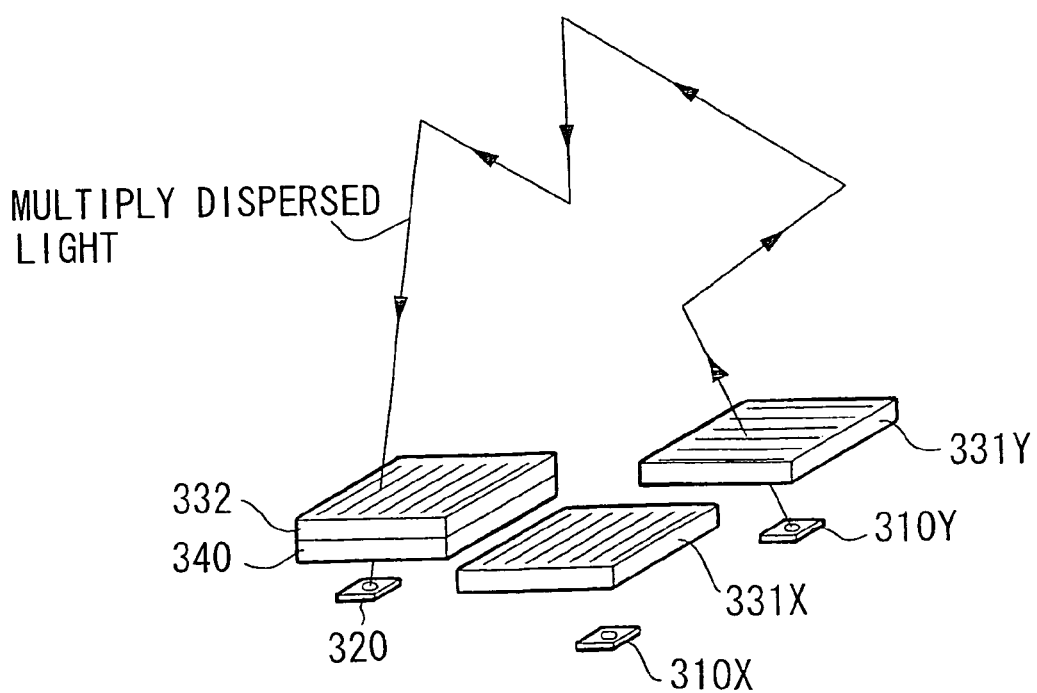

As shown in FIGS. 39A and 39B, reflected light detector 303 according to the tenth embodiment is formed with two light emitting elements 310x,310y, one light receiving element 320, polarizing plates 331x,331y, and 332 provided on the light emitting surface sides of light emitting elements 310x,310y and the light receiving surface side light receiving element 320, and filter 340 provided on the light receiving surface side. The direction of polarization of polarizing plate 331x on the light emitting side is the same as that of the polarizing plate 332 on the light receiving side, while the direction of polarization of polarizing plate 331y is perpendicular to that of polarizing plate 332.

Light emitting elements 310x,310y and light receiving element 320 are disposed in the same plane in FIG. 39. The distance between light emitting element 310x and light receiving element 320, and the distance between light emitting element 310y and light receiving element 320, are equal. This is because it is preferable that the light emitted by light emitting elements 310x,310y be received by light receiving element 320 under equivalent conditions.

Figure 40:
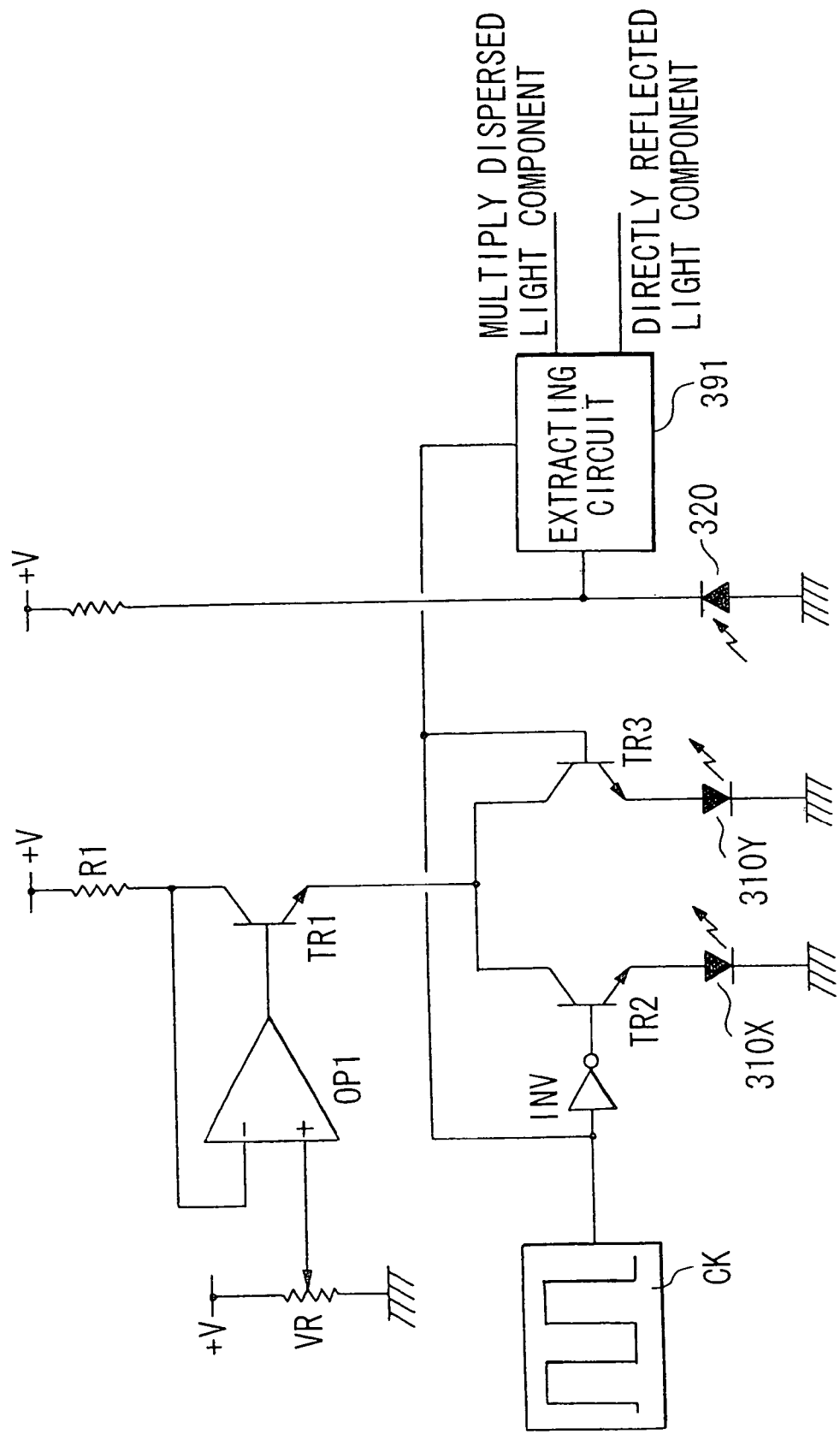
FIG. 40 is a block diagram showing the structure of the processing circuit in the tenth embodiment of the present invention.

Reflected light detector 303 having the design as described above is driven and carries out processing by means of the circuit shown in FIG. 40. As shown in this figure, the fixed current source is formed with an operational amplifier OP1, transistor TR1, and resistor R1. A current Ie (=(V−V1)/R1) corresponding to voltage V1 set by variable resistor VR is supplied in the emitter for transistor TR1. Transistors TR2,TR3 are for switching light emitting elements 310x,310y, with the base of each supplied with signal CK and the inverted signal for signal CK from an inverter. Accordingly, transistors TR2,TR3 are alternately turned on and off When signal CK is at level [H], then light emitting element 310x is turned off and light emitting element 310y is turned on. In contrast, when signal CK is at level [L], then light emitting element 310x is turned on while light emitting element 310y is turned off. As a result, light polarized in the same direction as the polarizing plate at the light receiving surface, and light polarized in a direction perpendicular to the polarizing plate at the light receiving surface, are alternatively switched and emitted.

Extracting circuit 391 extracts the output from light receiving element 320 after separating the result into the case when signal CK is at level [H] and when signal CK is at level [L].

In the tenth embodiment, when signal CK is at level [L], i.e., when light emitting element 310x is on, then, as shown in FIG. 39A, light receiving element 320 receives a directly reflected light component in which the polarization state is maintained. When signal CK is at level [H], i.e., when light emitting element 310y is on (FIG. 39B) then light receiving element 320 receives a dispersed light component in which the polarization state is not maintained. Thus, the output of light receiving element 320 extracted when signal CK is at level [L] directly indicates the reflected light component, while the output of light receiving element 320 extracted when signal CK is at level [H] directly indicates the dispensed light component. Accordingly, by employing the reflected light detector 303 according to the third embodiment, it is possible to alternately detect both the directly reflected light component and the dispersed light component in the light reflected by the dispersing medium. Thus, as in the case of the second embodiment, even more information can be obtained about the dispersing medium.

When the intensity of the polarized light component emitted by light emitting elements 310x,310y is equal, then the quantity of emitted light becomes constant, regardless of the on/off state of the light emitting element.

In general, conventional optical wireless communication devices (a remote control for a television or air conditioner for example) carry out communications by employing modulation of the light intensity. Thus, since the quantity of light emitted in the third embodiment is constant over time, it does not impart a negative effect on such existing optical wireless communication devices.

Note that in the tenth embodiment, the frequency of signal CK must be two-fold greater than the frequency of the information being obtained on the dispersing medium.

Since the directly reflected light component is not detected when signal CK is at level [H] in the tenth embodiment, both the directly reflected light component and the dispersed light component cannot be detected simultaneously, as in the case of the ninth embodiment. However, provided that a high frequency for signal CK is set, then the detection is essentially simultaneous, so that this is not believed to be a problem in terms of practical application.

In addition, the tenth embodiment is designed so that the light intensity is constant by alternately driving light emitting elements 310x,310y. However, it is also acceptable to provide a time interval in which either light emitting element 310x or 310y is off, and the external light component is canceled as in the case of the modification of the first embodiment. Namely, regarding driving the light emitting element, (1) only light emitting element 310x can be turned on, (2) only light emitting element 310y can be turned on, or (3) both light emitting elements can be controlled to be off in sequence. The directly reflected light component from which the external light component has been canceled can then be obtained by subtracting the signal output from light receiving element 320 when (3) all light emitting elements are off, from the signal output from light receiving element 320 when (1) light emitting element 310x is on. The dispersed light component from which the external light component has been canceled can then be obtained by subtracting the signal output from light receiving element 320 when (3) all light emitting elements are off, from the signal output from light receiving element 320 when (2) light emitting element 310y is on (however, the merit of a constant light intensity can no longer be obtained then).

In the tenth embodiment, light emitting elements 310x, 310y were alternately turned on to adjust the polarization state at the emission side. In addition, polarization can be adjusted using a variety of other elements, however. For example, adjustment of the polarization may also be realized by means of (1) a design in which the polarizing direction of light emitted from a usual type of light source is adjusted using a rotary polarization element such as a liquid crystal, or (2) a design employing the polarization adjusting light emitting element which is explained below.

(1) Polarization Adjusting Light Emitting Element

The use of a polarization adjusting light emitting element when adjusting the polarization state at the emission side will now be explained. The polarization adjusting light emitting element mentioned here employs one or a plurality of elements, and is capable of adjusting the direction of polarization of the emitted light. A plurality of the above-described planar emission semiconductor lasers 700 may be used, or an improved version thereof may be employed.

The planar emission semiconductor laser 700 shown in FIG. 35 (equivalent to FIG. 4 or 5) only emits laser light. By manipulating the shape of the optical resonator, however, the direction of polarization of the laser light can be controlled. Therefore, adjustment of polarization can be realized by designing semiconductor laser 700 as follows, for use at the polarization adjusting light emitting element.

(a) Forming Optical Resonator as a Circle

The optical resonator may be given a circular shape such as shown in FIG. 4, for example.

(b) Forming Optical Resonator as a Rectangle

The optical resonator may be given a rectangular shape such as shown in FIG. 7, for example.

By determining the shape of the optical resonator in the planar emission semiconductor laser in this way, it is possible to control the direction of polarization of the emitted light by appropriately driving the optical resonator.

When employing a semiconductor laser to form light emitting element 310, the light emitted by the laser is already polarized when it is emitted from the optical resonator. Accordingly, the polarizing plate may be omitted from the light emitting surface. Provision of a polarizing plate is significant, however, with respect to the goal of increasing the quenching ratio (i.e., the ratio of the light intensity in the main direction of polarization and the direction of polarization perpendicular thereto).

It is of course possible to bring together the light emitting wavelength and the sensitivity wavelength by forming both the polarization adjusting element and the photo diode 500 (see FIG. 33A) on the same wafer. However, in this case, the distance between each of the elements becomes extremely close, so that it becomes difficult to provide a polarizing plate on only the light receiving surface of photo diode 500. For this reason, when forming the polarization adjusting light emitting element and photo diode 500 on the same wafer, it is preferable to provide some separation between the two at the mounting stage.

N: Embodiment 11

Drawing from the eighth through tenth embodiments, an explanation will now be made of the eleventh embodiment in which the dispersing medium is the human body, and the pulse waveform is detected in that body. Detection of the pulse waveform is significant, because of the variety of information, such as pulse rate, which can be obtained related to the body as a result.

Figure 41:
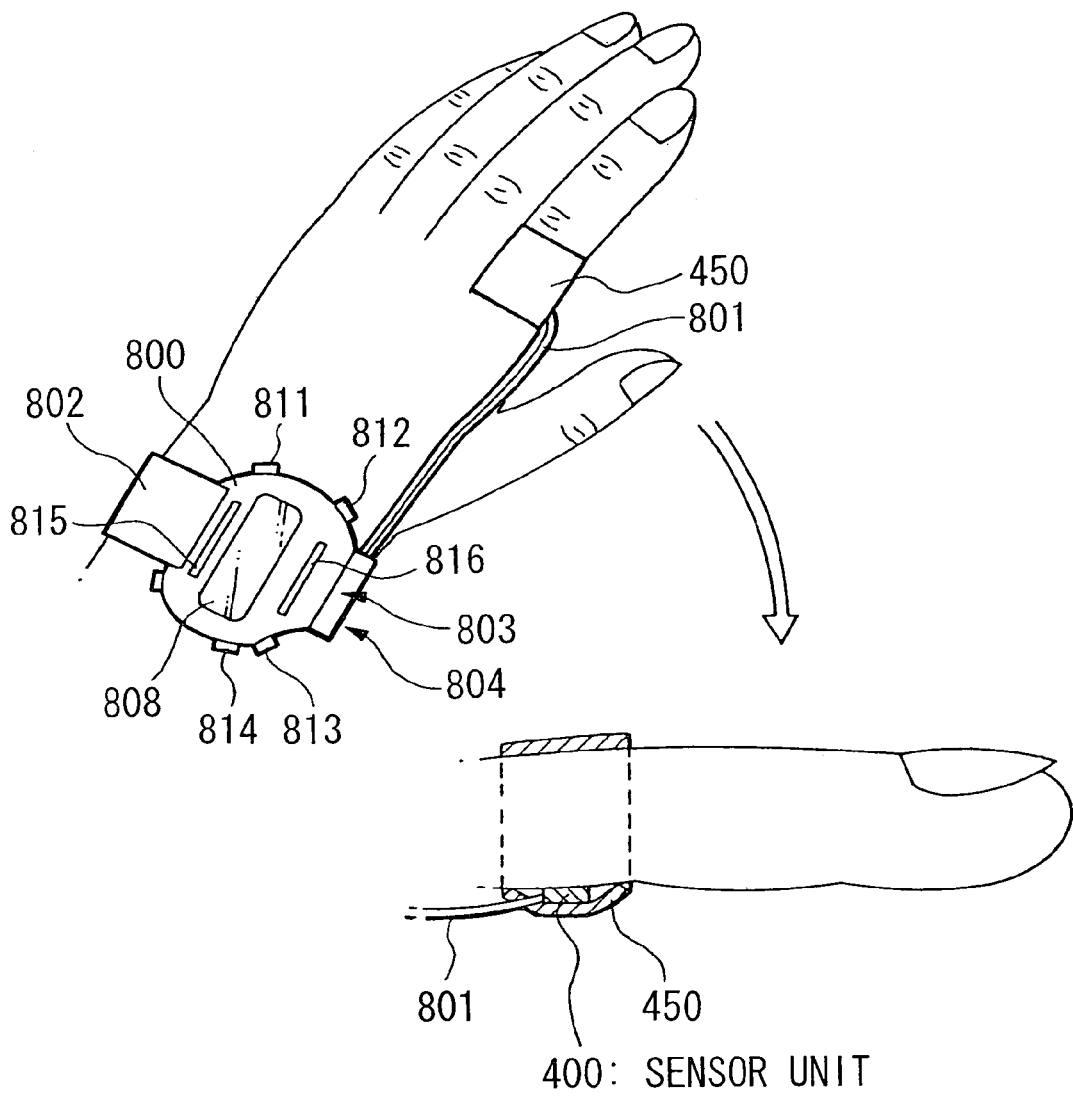
FIG. 41A is a rough structural diagram of the pulse wave detecting device according to the eleventh embodiment of the present invention.
FIG 41B illustrates the positioning of the sensor unit of the detecting device shown in FIG. 41A.

FIG. 41A is an explanatory figure showing the overall structure of pulse wave detecting device 304 according to the eleventh embodiment. As shown in this figure, pulse wave detecting device 304 according to this embodiment is formed of a main body 800 having a wristwatch structure, a cable 801 connected to device main body 800, and a sensor unit 400 provided on the end of cable 801.

A wrist band 802 is attached to device main body 800. One end of wrist band 802 wraps around the user's left arm from the 12 o'clock position of device main body 800, while the other end is fixed at the 6 o'clock position of device main body 800.

A connector 803 is provided on the side surface of device main body 800 at the 6 o'clock position. The connector piece 804 provided on the end of cable 801 attaches in a freely releasable manner to the end of connector 803. By releasing connector piece 804 from connector 803, the main device can be employed as a wristwatch or stop watch.

A display 808 is provided on the surface of watch main body 800, for displaying a variety of information using a dot matrix or segment display. Button switches 811~816 are provided on the surface of device main body 800 for carrying out various settings.

As shown in FIG. 41B sensor unit 400 is blocked from external light by sensor fixing band 450, and is attached between the base and joint of the index finger.

In general, when the temperature distribution is measured from the palm to the fingertip at a cool ambient temperature, it is clear that the temperature at the fingertip falls noticeably while the temperature at the base of the finger does not fall. Accordingly, if the sensor unit 400 is attached to the base of the finger, not only can cable 801 be made short, but accurate measurements may still be obtained of the pulse wave even on a cold day.

(1) Sensor Unit

Figure 42:
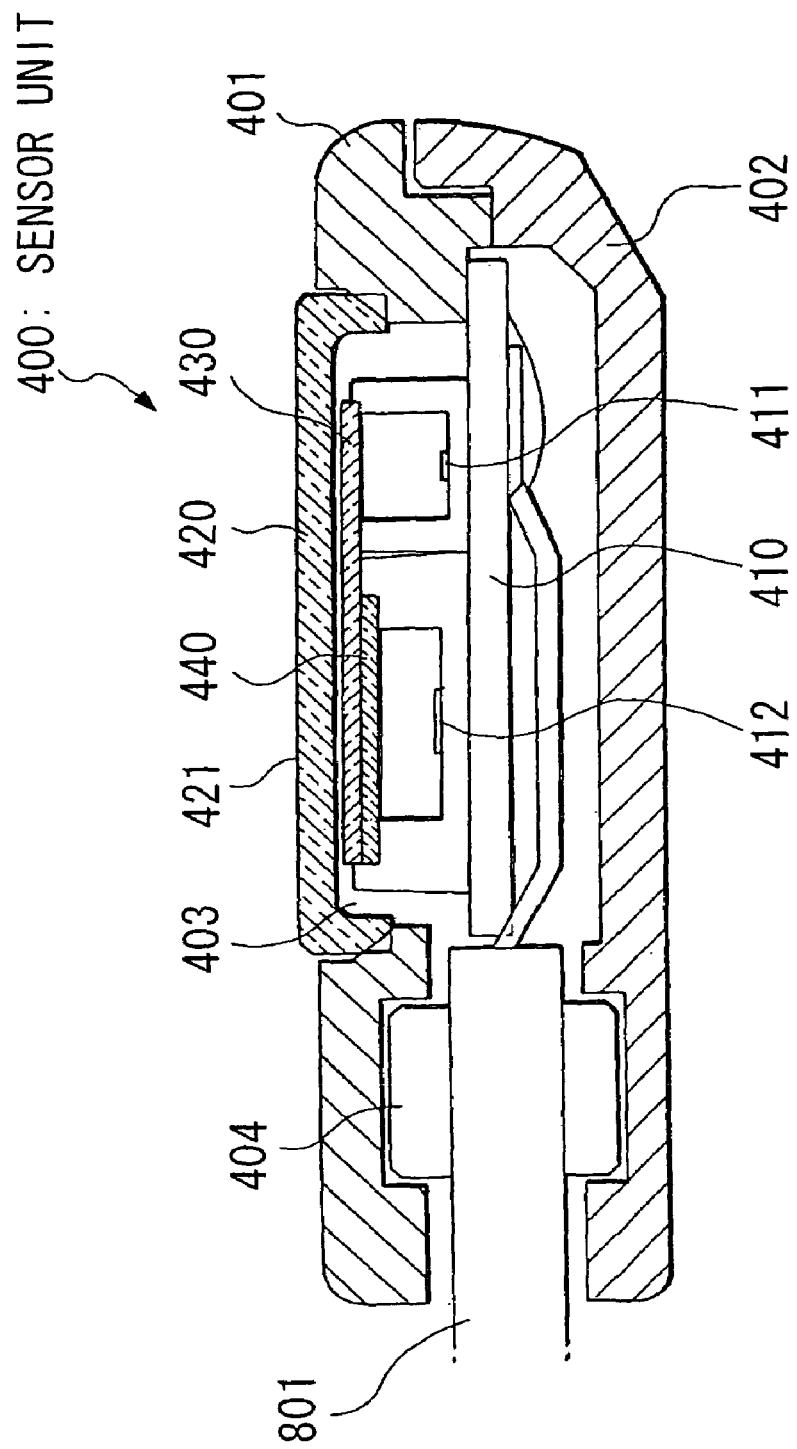
FIG. 42 is a lateral cross-sectional diagram showing the structure of the sensor unit in the eleventh embodiment of the present invention.

Sensor unit 400 will now be explained. FIG. 42 is a cross-sectional diagram showing the structure of sensor unit 400. As shown in the figure, a rear cover 402 covers the sensor frame 401 as a case, so that a component housing space 403 is formed inside sensor unit 400. Electrical components such as semiconductor laser 411, photo diode 412, and the like are mounted on circuit board 410, which is disposed inside component housing space 403. The end of cable 801 is fixed in place to sensor unit 400 by means of a bushing 404, with its circuitry attached to circuit board 410.

Sensor unit 400 is attached to the finger so that cable 801 extends from the base of the finger to the side of device main body 800. Accordingly, semiconductor laser 411 and photo diode 412 are disposed so as to lie along the longitudinal direction of the finger at its tip and base, respectively. As a result, light from the outside environment does not readily reach photo diode 412.

In sensor unit 400, a light transmitting window is formed in the upper portion of sensor frame 401 by means of a light transmitting plate 420 consisting of a glass plate. A polarizing plate 430 is provided beneath light transmitting plate 420, while a filter 440 is provided on the photo diode 412 side. The light emitting surface of light emitting diode 411 and the light receiving surface of photo diode 412 each face light transmitting plate 420.

For this reason, when the surface of the finger contacts the outer surface 421 of light transmitting plate 420, light emitting diode 411 is positioned to emit light polarized by polarizing plate 430 toward the finger surface, while photo diode 412 is positioned to detect light reflected from the finger surface which has passed through filter 440, and which has components polarized in the same direction as the emitted light.

Figure 43:
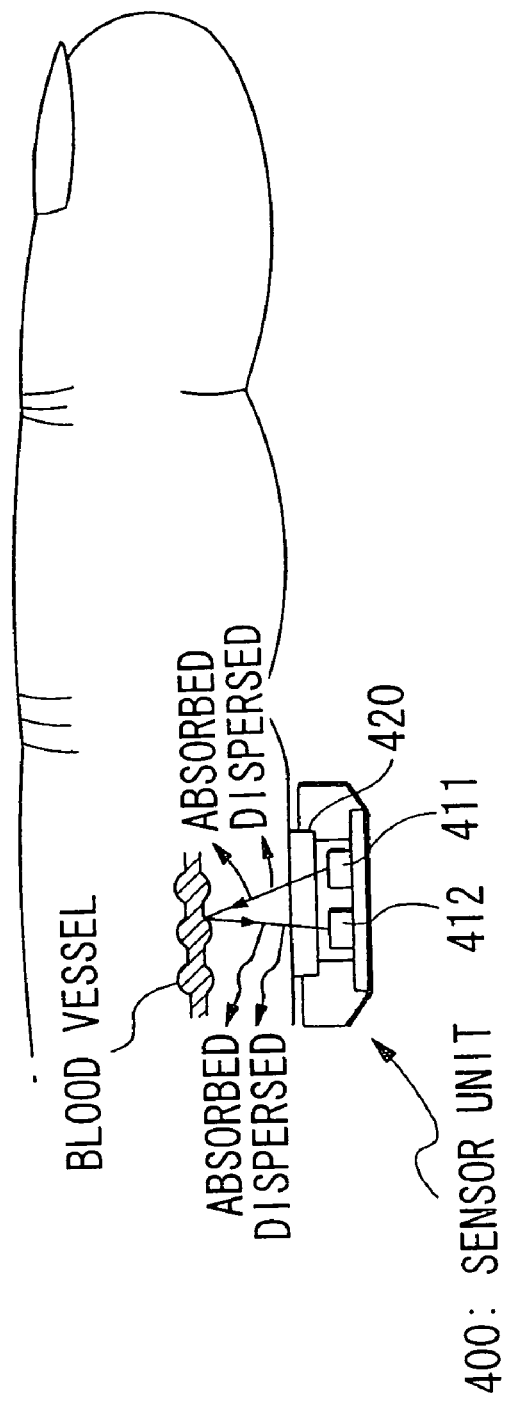
FIG. 43 is a diagram showing the case where the sensor unit is attached to the finger.

A sensor unit 400 of this design is attached to the base of the finger using a sensor affixing pad 450, as shown in FIG. 41B. In this arrangement, semiconductor laser 411 emits light on the finger, with the light reaching the blood vessels, as shown in FIG. 43. While a portion of the light reaching the blood vessels is absorbed by the hemoglobin in the blood, a portion is also reflected. Of the light reflected by the hemoglobin, some approaches other hemoglobin molecules, while some directly approaches photo diode 412.

Namely, the reflected light approaching photo diode 412 includes light which has been multiply reflected by the hemoglobin (multiply dispersed light component), as well as light emitted from semiconductor laser 412 which has been directly reflected (directly reflected light component). While the multiply dispersed light does not maintain its polarization state, the directly reflected light does.

In addition, when the blood volume is great, the amount of hemoglobin increases, while when the blood volume is small, the amount of hemoglobin decreases. Thus, when taking into consideration variations in the blood volume (blood pulse wave), it is clear that the directly reflected light component, and not the multiply dispersed light component, directly reflects the amount of hemoglobin present.

Because the polarizing plates on the emitting and receiving sides are the same in the present invention, only the component polarized in the same direction as the emitting side is detected on the receiving side. Thus, first, as a result of this embodiment's design, in which the finger is irradiated with light and the reflected light is then detected, it is possible to detect the directly reflected light component which reflects the amount of hemoglobin present.

As explained in the eighth embodiment, the semiconductor laser 411 and photo diode 412 in this embodiment both have optical resonators, and are separated in a dicing process after their active and depletion layers have been formed by the same layer forming process on the same wafer. This separation is accomplished by housing semiconductor laser 411 and photo diode 412 separately, so that the light emitted by semiconductor laser 411 does not fall on photo diode 412.

Hemoglobin in blood has a large absorption coefficient with respect to light in the wavelength range of 300 nm to 700 nm. Accordingly, in this embodiment, the active and depletion layers are set so that the light emitting wavelength for semiconductor laser 411 and the sensitivity wavelength for photo diode 412 are around 660 nm.

As a result, second, in this embodiment, in which the finger is irraidated with light and the reflected light is then detected, it is possible to detect changes in blood flow with good sensitivity.

(2) Electrical Structure and Action

The signal detected by photo diode 412 shows the changes in blood flow within the body. As a result, the pulse wave for the body can be obtained, providing various information about the body.

It is assumed here, however, that conditions are limited to when the body is at rest. This is because when the body is moving, a signal component arising from this movement is superimposed on the signal detected by photo diode 412.

Therefore, the device may be designed so that a body motion sensor for detecting the body's motion component is provided, and the signal detected by the body motion sensor is subtracted from the signal detected by photo diode 412. As a result, it is possible to obtain the pulse wave component only, even when the body is moving.

However, in a design such as this, it is possible that when the body is almost at rest, then the signal detected by this body motion sensor may function as noise, so that it is not possible to accurately obtain just the pulse wave component.

On the other hand, a design may be considered in which the processing of the detection signal from photo diode 412 is manually switched for the case where the body is at rest and the case where the body is moving. However, this design is troublesome in that it requires the user to judge the body state, as well as perform manual operations.

Figure 44:
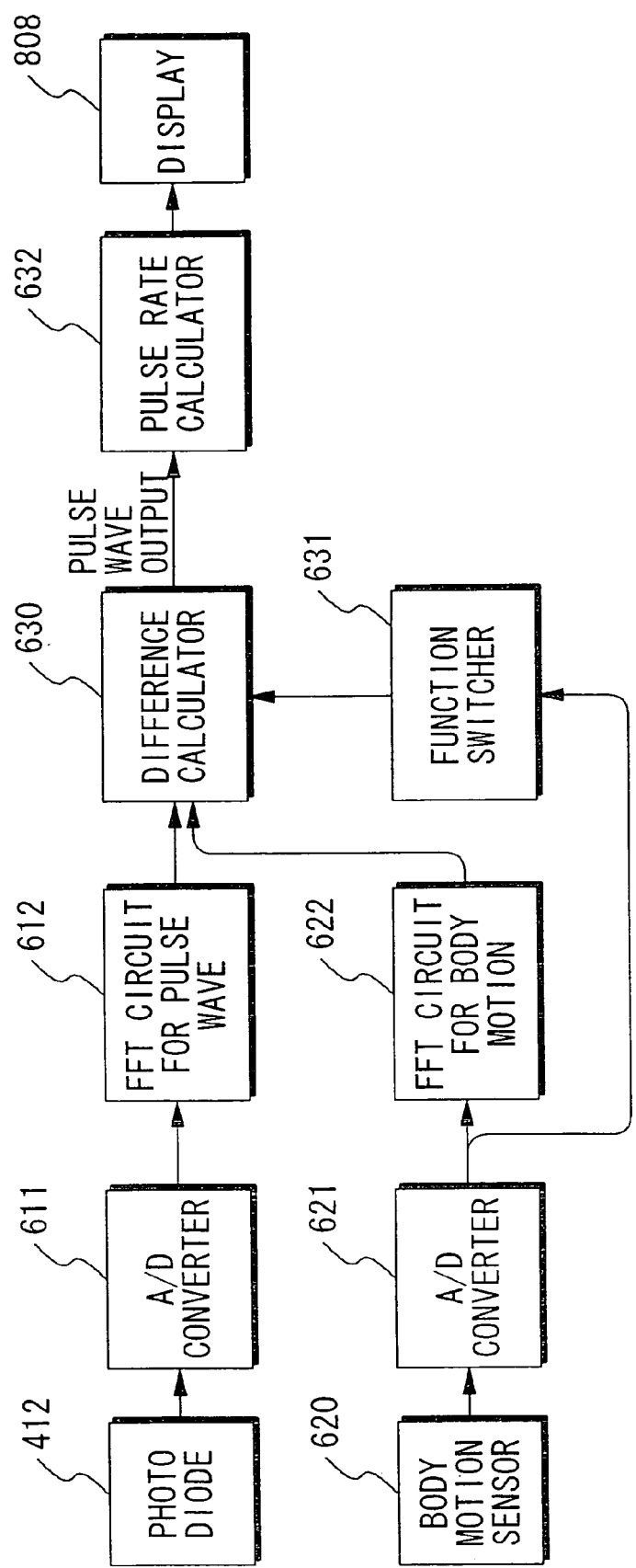
FIG. 44 is a block diagram showing the electrical structure in the eleventh embodiment.
Figure 45:
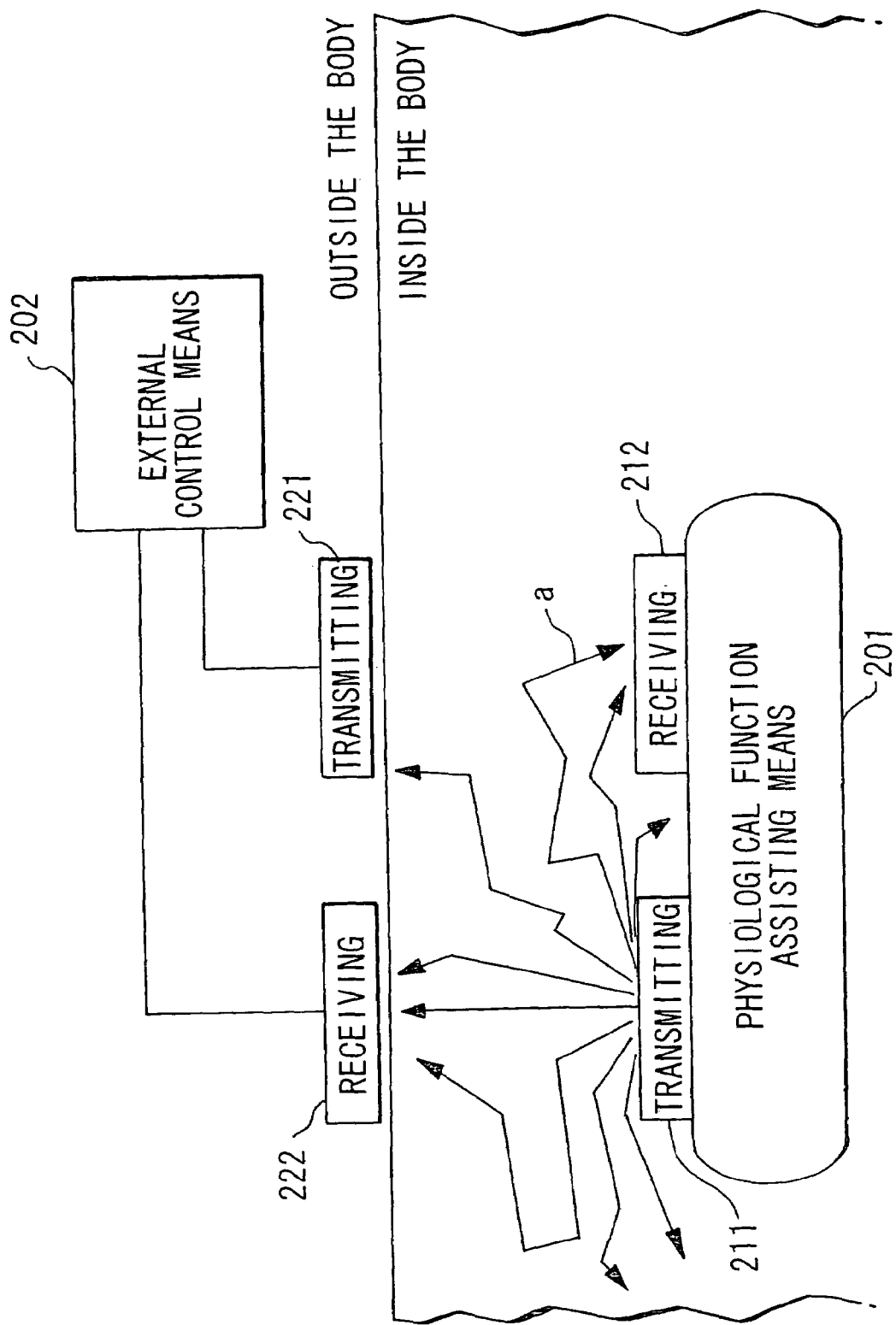
FIG. 45 is a block diagram showing the operation and structure of a conventional communication device.
Figure 46:
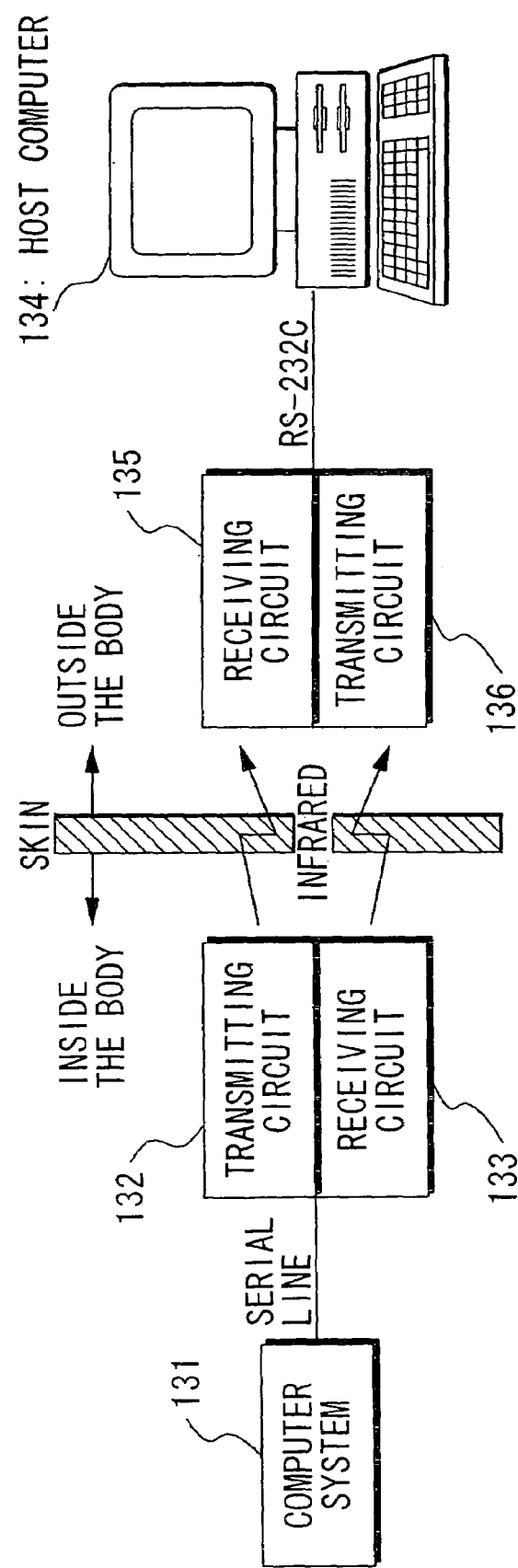
FIG. 46 is a block diagram showing the overall structure of a conventional communication device.

Thus, in order to enable pulse wave detecting device 304 to accurately detect the pulse wave regardless of whether the body is at rest or moving, an electrical structure such as explained next is provided. FIG. 44 is a block diagram showing this electrical structure. In this figure, the pulse wave signal output from photo diode 412 is amplified by amplifying circuit 611, converted to a digital signal by A/D converter 612, and then supplied to pulse wave FFT circuit 613. Pulse wave FFT circuit 613 performs frequency analysis of the digital signal from A/D converter 612, by carrying out FFT processing (fast Fourier transform). The results of this analysis are supplied to difference calculator 630.

At the same time, body motion sensor 620 is formed of a so-called acceleration sensor for detecting movement of the body, and is housed inside device main body 800. The body motion signal which is the output of body motion sensor 620 is amplified by amplifying circuit 621, converted to a digital signal at A/D converter 622, and supplied to body motion FFT circuit 623 and function switcher 631. Body motion FFT circuit 623 carries out frequency analysis by performing FFT processing of the digital signal from A/D converter 622, and supplies the result of this analysis to difference calculator 630.

Difference calculator 630 has the following two functions. Namely, difference calculator 630 is provided with a first function for supplying the frequency component obtained from pulse wave FFT circuit 613 to pulse rate calculator 632 without performing any type of processing thereto, and a second function for comparing the frequency components of the pulse wave spectrum obtained by pulse wave FFT circuit 613 and the frequency components of the body motion spectrum obtained by body motion FFT circuit 623, removing the body motion components from coinciding pulse wave components, and supplying the result to pulse wave calculator 632. The selection of the first or second function in pulse wave component extractor 630 is carried out under the control of function switcher 631.

Function switcher 631 determines whether the body is at rest or moving based on the signal from A/D converter 622. When function switcher 631 determines that the body is at rest, then the first function is selected in pulse wave component extractor 630. In contrast, when function switcher 631 determines that the body is moving, then the second function is selected in pulse wave component extractor 630.

Function switcher 631 determines whether the body is at rest or not based on the level of the body motion signal, frequency components, etc. Specifically, there are methods available such as (1) a method in which determination is made from the amplitude level of the body motion signal, (2) a method in which determination is made from the frequency spectrum of the body motion signal, and the like. The latter method is further divided into a method in which determination is made from the maximum spectrum level, and a method in which determination is made from the spectrum dispersion (i.e., relative comparison in each spectrum level). Here, the function switcher 631 according to this embodiment employs method (1) to determine whether or not the body is at rest.

Function switcher 631 extracts the maximum level spectrum out of the frequency spectrums processed at body motion FFT circuit 623. If this maximum level spectrum is less than threshold value Ath, then a determination is made that the body is at rest. Conversely, if this maximum level spectrum is above threshold value Ath, then a determination is made that the body is moving. Threshold value Ath is a value which serves as the standard for determining whether the body is at rest or moving.

Note that a state of motion as used here is motion of a given constant regularity, such as walking or jogging.

Out of the frequency components from difference calculator 630 pulse rate calculator 632 extracts the maximum level frequency component as the pulse component expressing the pulse, and converts the frequency of the pulse component to a per-minute pulse rate. Display 808 is designed to display the converted result from pulse rate calculator 632.

In this embodiment, difference calculator 630, function switcher 631, and pulse rate calculator 632 consist of microcomputers which execute processes indicated by programs which have been stored in advance.

The ultimate objective of processing in this embodiment is the display of the pulse rate. However, this is just one example of processing on the obtained pulse waveform and is not intended to limit the present invention in any way.

When the body is judged to be at rest in a pulse-wave detecting device 304 of the above-described design, difference calculator 630 outputs the pulse wave spectrum from pulse wave FFT circuit 613 as is, without considering a body motion component. On the other hand, when the body is judged to be moving, difference calculator 630 outputs pulse wave components from which the body motion component has been removed.

Accordingly, it is possible to accurately detect the pulse rate, and the pulse wave output, irrespective of whether the body is at rest or moving.

What is claimed:

1. A light communication system for performing communication between a physiological function assisting device and a controlling device, the system comprising:

in the physiological function assisting device, means for detecting an internal state of a living body and generating a data signal representing the detected state;

a first transmitting means for transmitting light whose intensity is modulated on the basis of the detected data signal;

a first receiving means for receiving and demodulating light transmitted by the controlling device to extract a control signal included in the light;

in the controlling device, means for generating the control signal;

a second transmitting means for transmitting light whose polarization plane is rotated according to the control signal; and a receiving means for receiving and demodulating light transmitted by the physiological function assisting device, to extract the data signal included in the light.

2. A light communication system for performing communication between a physiological function assisting device and a controlling device, the system comprising:

in the physiological function assisting device, means for detecting an internal state of a living body and generating a data signal representing the detected state;

a first transmitting means for transmitting light whose polarization plane is rotated according to the detected data signal;

a first receiving means for receiving and demodulating light transmitted by the controlling device to extract a control signal included in the light;

in the controlling device, means for generating the control signal;

a second transmitting means for transmitting light whose intensity is modulated on the basis of the control signal; and a receiving means for receiving and demodulating light transmitted by the physiological function assisting device, to extract the data signal included in the light.

* * * * *